(12) United States Patent
Qiao et al.

(10) Patent No.: US 9,000,260 B2
(45) Date of Patent: Apr. 7, 2015

(54) ETP1 AND ETP2 REGULATE PLANT ETHYLENE RESPONSE

(75) Inventors: Hong Qiao, San Diego, CA (US); Joseph R. Ecker, Carlsbad, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 612 days.

(21) Appl. No.: 12/729,760

(22) Filed: Mar. 23, 2010

(65) Prior Publication Data

US 2010/0242135 A1    Sep. 23, 2010

Related U.S. Application Data

(60) Provisional application No. 61/162,469, filed on Mar. 23, 2009.

(51) Int. Cl.
| | |
|---|---|
| *A01H 1/00* | (2006.01) |
| *A01H 5/00* | (2006.01) |
| *C12N 5/04* | (2006.01) |
| *C12N 15/82* | (2006.01) |
| *C07K 14/415* | (2006.01) |
| *C12N 15/10* | (2006.01) |

(52) U.S. Cl.
CPC ............... *C12N 15/8271* (2013.01); *A01H 5/00* (2013.01); *C12N 15/8201* (2013.01); *C12N 15/8218* (2013.01); *C12N 15/8249* (2013.01); *C07K 14/415* (2013.01); *C12N 15/1048* (2013.01); *C12N 15/8262* (2013.01)

(58) Field of Classification Search
None
See application file for complete search history.

(56) References Cited

U.S. PATENT DOCUMENTS

2006/0200875 A1    9/2006  Guo et al.
2011/0321191 A1*  12/2011  Rosichan ..................... 800/278

OTHER PUBLICATIONS

Qiao et al, Genes and Development, electronic publication date Feb. 4, 2009, cited in the IDS filed Mar. 15, 2012.*
Gagne et al., "The F-box subunit of the SCF E3 complex is encoded by a diverse superfamily of genes in *Arabidopsis*," *Proc. Natl. Acad. Sci. USA*; 99(17):11519-11524 (2002).
Kim et al., :Trifurcate Feed-Forward Regulation of Age-Dependent Cell Death Involving miR164 in *Arabidopsis*, *Science*; 323:1053-1057 (2009).
Qiao, et al., "Interplay between ethylene, ETP1/ETP2 F-box proteins, and degradation of EIN2 triggers ethylene responses in *Arabidopsis*," *Genes Dev.*; ePub Feb. 4, 2009.
Xu et al.; "Evolution of F-box genes in plants: Different modes of sequence divergence and their relationships with functional diversification," *Proc. Natl. Acad. Sci. USA*; 106(3):835-840 (2009).

* cited by examiner

*Primary Examiner* — Eileen B O Hara
(74) *Attorney, Agent, or Firm* — Kilpatrick Townsend Stockton LLP

(57) ABSTRACT

ETP1 and ETP2 bind to EIN2 and modulate plant ethylene sensitivity.

10 Claims, 16 Drawing Sheets

SEQUENCE LISTING

<160> NUMBER OF SEQ ID NOS: 22

<210> SEQ ID NO 1
<211> LENGTH: 415
<212> TYPE: PRT
<213> ORGANISM: Arabidopsis thaliana
<220> FEATURE:
<223> OTHER INFORMATION: thale cress ecotype Columbia ethylene-
      insensitive 2 (EIN2) targeting protein 1 (ETP1), F-box family
      protein, locus AT3G18980

<400> SEQUENCE: 1

```
Met Thr Ile Pro Asp Leu Cys Asn Asp Leu Val Asp Glu Ile Leu Cys
 1               5                  10                  15

Arg Val Pro Ala Arg Asn Leu Lys Arg Leu Arg Ser Thr Ser Lys Arg
            20                  25                  30

Trp Asn Arg Leu Phe Lys Asp Asp Arg Arg Phe Ala Arg Glu His Met
        35                  40                  45

His Lys Ala Pro Lys Glu Tyr Leu Pro Leu Met Leu Thr Ser Glu Tyr
    50                  55                  60

Arg Ile Cys Pro Val Ser Ile Asn Leu Gln Gly Asp Val Pro Ser Val
65                  70                  75                  80

Val Leu Lys Arg Glu Leu Ser Leu Pro Asp Pro Asp Tyr Ser His Gln
                85                  90                  95

Phe Asp Ile Gly Arg Val Phe His Cys Asp Gly Leu Leu Val Cys Asn
            100                 105                 110

His Val Gly Lys Asn Pro Arg Tyr Gly Ser Lys Ile Val Val Trp Asn
        115                 120                 125

Pro Leu Thr Gly Gln Thr Arg Trp Ile Glu Ala Gly Tyr Arg Trp Lys
    130                 135                 140

Glu Tyr Glu Val Arg Phe Val Leu Gly Tyr Cys Tyr Gln Gln Asp Glu
145                 150                 155                 160

Asn Asn Ser Cys Ser Lys Lys Ile Tyr Lys Ile Leu Cys Phe Tyr Pro
                165                 170                 175

Asn Gly Gln Asp Thr Glu Ile Tyr Glu Leu Asn Tyr Ser Asp Arg Trp
            180                 185                 190

Thr Arg Thr Ile Pro Asp Gly Asp Leu Thr Pro Gly Trp Thr Leu Ile
        195                 200                 205

Tyr Ser Glu Gln Thr Val Ser Met Asn Gly Asn Leu Tyr Leu Phe Ala
    210                 215                 220

Ser Glu Lys Ser Lys Pro His Leu Gly Val Ser Leu Leu Arg Phe Asp
225                 230                 235                 240

Phe Ser Thr Glu Lys Ser Ser Leu Cys Val Thr Leu Pro Tyr Gln Arg
                245                 250                 255

Pro Arg Tyr Glu Ile Leu Ser Ile Ser Ala Val Arg Gly Gly Glu Asn
            260                 265                 270

Leu Ser Leu Leu Leu Gln Leu Asp Phe Glu Ser Lys Thr Glu Ile Trp
        275                 280                 285

Val Thr Asn Lys Ile Asp Asp Thr Thr Lys Gly Ala Ala Val Ser
    290                 295                 300

Trp Thr Lys Val Leu Ala Phe Asp Leu Ser Pro Asp Leu Gln Leu Phe
305                 310                 315                 320

Ser Glu Glu Val Asn Phe Leu Leu Asp Glu Asp Lys Lys Val Ala Val
                325                 330                 335

Cys Cys Glu Arg Trp Leu Glu Pro Gln Glu His Arg Tyr Gln Cys
            340                 345                 350
```

```
Arg Arg Glu Tyr Lys Ile Thr Asp Lys Ile Tyr Ile Leu Gly Glu Asp
        355                 360                 365

Asn Lys Val Asp Glu Val Gly Ser Gly Glu Gly Ala Thr Asp Ser
    370                 375                 380

Leu Glu Gly Ile Ser Gln Val Ile Leu Asn Tyr Ala Pro Ser Leu Val
385                 390                 395                 400

Gln Ile Glu Gln Ala Gly Gly Gly Lys Thr Lys Arg Gly Asp Asp
                405                 410                 415

<210> SEQ ID NO 2
<211> LENGTH: 388
<212> TYPE: PRT
<213> ORGANISM: Arabidopsis thaliana
<220> FEATURE:
<223> OTHER INFORMATION: thale cress ecotype Columbia ethylene-
      insensitive 2 (EIN2) targeting protein 2 (ETP2), F-box family
      protein, locus AT3G18910

<400> SEQUENCE: 2

Met Lys Thr Ile Gln Glu Gln Leu Pro Asn Asp Leu Val Glu Glu Ile
1               5                   10                  15

Leu Cys Arg Val Pro Ala Thr Ser Leu Arg Arg Leu Arg Ser Thr Cys
            20                  25                  30

Lys Ala Trp Asn Arg Leu Phe Lys Gly Asp Arg Ile Leu Ala Ser Lys
        35                  40                  45

His Phe Glu Lys Ser Ala Lys Gln Phe Arg Ser Leu Ser Leu Arg Asn
    50                  55                  60

Asp Tyr Arg Ile Phe Pro Ile Ser Phe Asn Leu His Gly Asn Ser Pro
65                  70                  75                  80

Ser Leu Glu Leu Lys Ser Glu Leu Ile Asp Pro His Ser Lys Asn Ser
                85                  90                  95

Ala Ala Pro Phe Glu Ile Ser Arg Val Ile His Cys Glu Gly Leu Leu
            100                 105                 110

Leu Cys Ser Ser Gln Leu Asp Glu Ser Arg Val Val Trp Asn Pro
        115                 120                 125

Leu Thr Gly Glu Thr Arg Trp Ile Arg Thr Gly Asp Phe Arg Gln Lys
    130                 135                 140

Gly Arg Ser Phe Asp Val Gly Tyr Tyr Tyr Gln Lys Asp Lys Arg Ser
145                 150                 155                 160

Trp Ile Lys Ser Tyr Lys Leu Leu Cys Tyr Tyr Arg Gly Thr Lys Tyr
                165                 170                 175

Phe Glu Ile Tyr Asp Phe Asp Ser Asp Ser Trp Arg Ile Leu Asp Asp
            180                 185                 190

Ile Ile Ala Pro Arg Gly Ser Ile Gly Tyr Ser Glu Leu Ser Val Ser
        195                 200                 205

Leu Lys Gly Asn Thr Tyr Trp Phe Ala Lys Gly Val Thr Glu Glu Arg
    210                 215                 220

Pro Arg Thr Ile Ser Leu Leu Lys Phe Asp Phe Tyr Thr Glu Lys Ser
225                 230                 235                 240

Val Pro Val Leu Leu Pro Tyr Gln Ser Arg Arg Leu Phe Gln Ala Ser
                245                 250                 255

Ser Leu Ser Val Val Arg Glu Asp Lys Leu Ser Val Leu Leu Gln Leu
            260                 265                 270

Asp Gln Ser Ser Lys Thr Glu Ile Trp Val Thr Asn Val Ile Asp Glu
        275                 280                 285
```

```
Thr Thr Lys Gly Ala Val Ser Trp Thr Lys Val Leu Ala Leu Asp Leu
    290                 295                 300

Ser Pro His Leu Gln Ile Gly Asn Asp Gly Ser Phe Phe Leu Gly Glu
305                 310                 315                 320

Asp Lys Lys Val Val Met Phe Cys Glu Lys Leu Ile Asp Glu Asn Lys
                325                 330                 335

Val Lys Asp Met Val Tyr Ile Val Gly Glu Asp Asn Val Val Thr Glu
            340                 345                 350

Val Gly Phe Gly Val Asp Glu Met Asp Gly Cys Arg Ala Val Ile Leu
        355                 360                 365

Asn Tyr Val Pro Ser Leu Val Gln Ile Glu Arg Ala Gly Gly Asn Arg
    370                 375                 380

Lys Arg Gly His
385

<210> SEQ ID NO 3
<211> LENGTH: 388
<212> TYPE: PRT
<213> ORGANISM: Arabidopsis thaliana
<220> FEATURE:
<223> OTHER INFORMATION: thale cress ecotype Columbia F-box family
      protein, locus AT3G18910

<400> SEQUENCE: 3

Met Lys Thr Ile Gln Glu Gln Leu Pro Asn Asp Leu Val Glu Glu Ile
1               5                   10                  15

Leu Cys Arg Val Pro Ala Thr Ser Leu Arg Arg Leu Arg Ser Thr Cys
            20                  25                  30

Lys Ala Trp Asn Arg Leu Phe Lys Gly Asp Arg Ile Leu Ala Ser Lys
        35                  40                  45

His Phe Glu Lys Ser Ala Lys Gln Phe Arg Ser Leu Ser Leu Arg Asn
    50                  55                  60

Asp Tyr Arg Ile Phe Pro Ile Ser Phe Asn Leu His Gly Asn Ser Pro
65                  70                  75                  80

Ser Leu Glu Leu Lys Ser Glu Leu Ile Asp Pro His Ser Lys Asn Ser
                85                  90                  95

Ala Ala Pro Phe Glu Ile Ser Arg Val Ile His Cys Glu Gly Leu Leu
            100                 105                 110

Leu Cys Ser Ser Gln Leu Asp Glu Ser Arg Val Val Trp Asn Pro
        115                 120                 125

Leu Thr Gly Glu Thr Arg Trp Ile Arg Thr Gly Asp Phe Arg Gln Lys
    130                 135                 140

Gly Arg Ser Phe Asp Val Gly Tyr Tyr Tyr Gln Lys Asp Lys Arg Ser
145                 150                 155                 160

Trp Ile Lys Ser Tyr Lys Leu Leu Cys Tyr Tyr Arg Gly Thr Lys Tyr
                165                 170                 175

Phe Glu Ile Tyr Asp Phe Asp Ser Asp Ser Trp Arg Ile Leu Asp Asp
            180                 185                 190

Ile Ile Ala Pro Arg Gly Ser Ile Gly Tyr Ser Glu Leu Ser Val Ser
        195                 200                 205

Leu Lys Gly Asn Thr Tyr Trp Phe Ala Lys Gly Val Thr Glu Glu Arg
    210                 215                 220

Pro Arg Thr Ile Ser Leu Leu Lys Phe Asp Phe Tyr Thr Glu Lys Ser
225                 230                 235                 240

Val Pro Val Leu Leu Pro Tyr Gln Ser Arg Arg Leu Phe Gln Ala Ser
                245                 250                 255
```

```
Ser Leu Ser Val Val Arg Glu Asp Lys Leu Ser Val Leu Leu Gln Leu
            260                 265                 270

Asp Gln Ser Ser Lys Thr Glu Ile Trp Val Thr Asn Val Ile Asp Glu
        275                 280                 285

Thr Thr Lys Gly Ala Val Ser Trp Thr Lys Val Leu Ala Leu Asp Leu
    290                 295                 300

Ser Pro His Leu Gln Ile Gly Asn Asp Gly Ser Phe Phe Leu Gly Glu
305                 310                 315                 320

Asp Lys Lys Val Val Met Phe Cys Glu Lys Leu Ile Asp Glu Asn Lys
                325                 330                 335

Val Lys Asp Met Val Tyr Ile Val Gly Glu Asp Asn Val Thr Glu
            340                 345                 350

Val Gly Phe Gly Val Asp Glu Met Asp Gly Cys Arg Ala Val Ile Leu
            355                 360                 365

Asn Tyr Val Pro Ser Leu Val Gln Ile Glu Arg Ala Gly Gly Asn Arg
    370                 375                 380

Lys Arg Gly His
385

<210> SEQ ID NO 4
<211> LENGTH: 373
<212> TYPE: PRT
<213> ORGANISM: Arabidopsis thaliana
<220> FEATURE:
<223> OTHER INFORMATION: thale cress ecotype Columbia F-box family
      protein, locus AT3G19410

<400> SEQUENCE: 4

Met Thr Ile Pro Glu Leu Pro Lys Asp Leu Ile Glu Glu Ile Leu Cys
  1               5                  10                  15

Tyr Val Pro Ala Thr Tyr Leu Lys Arg Leu Arg Ser Thr Cys Lys Gly
             20                  25                  30

Trp Asn Arg Leu Phe Lys Asp Asp Arg Phe Ala Lys Lys His Tyr
         35                  40                  45

Asp Lys Ala Ala Lys Gln Phe Leu Pro Leu Met Ser Thr Asn Glu Glu
     50                  55                  60

Leu Cys Ala Met Ser Val Asn Leu His Gly Thr Ile Pro Ser Leu Glu
 65                  70                  75                  80

Val Lys Asp Lys Pro Trp Leu Phe Val Ser Asp Ser Lys His Cys Asp
                 85                  90                  95

Ile Glu Ile Ser Arg Ile Phe His Ser Gly Gly Leu Leu Leu Cys Phe
            100                 105                 110

Ser Arg Asp Gly Glu Ile Ser Ile Ile Val Trp Asn Pro Leu Thr Ser
        115                 120                 125

Glu Thr Arg Leu Ile Arg Thr Arg Asn Arg Arg Asp Lys Gly Arg Asn
    130                 135                 140

Phe Val Leu Gly Tyr Tyr Gln Glu Asp Lys Lys Thr Tyr Tyr Lys Ile
145                 150                 155                 160

Leu Ser Phe Tyr Leu Asp Ser Lys Asp Phe Glu Ile Phe Glu Phe Asn
                165                 170                 175

Ser Asp Ser Trp Arg Phe Ile Asp Asp Ile Cys Pro Gly Leu Ser Leu
            180                 185                 190

Leu Tyr Ser Asp Gln Cys Val Ser Leu Lys Gly Asn Thr Tyr Met Phe
        195                 200                 205

Ala Ile Asp Asp Leu Ser Val Ser Leu Leu Lys Tyr Asp Phe Ser Thr
```

```
             210                 215                 220
Glu Thr Ser Val Pro Val Pro Leu Pro Tyr Lys Ser Arg Ser Phe Glu
225                 230                 235                 240

Ala Ile Ser Leu Ser Val Val Arg Glu Glu Lys Leu Ser Val Leu Leu
                245                 250                 255

Gln Arg Asp Lys Ser Ser Lys Thr Glu Ile Trp Val Thr Asn Val Ile
            260                 265                 270

Asp Glu Thr Thr Thr Lys Val Met Val Val Ser Trp Ser Lys Val Leu
        275                 280                 285

Ser Leu Asp Leu Ser Pro Asp Leu Lys Ile Arg Tyr Gly Glu Ser Phe
    290                 295                 300

Leu Leu Asp Glu Glu Lys Lys Val Ile Met Ile Phe Asn Asn Arg Met
305                 310                 315                 320

Glu Glu Glu Asn Lys Ser Glu Asp Lys Leu Tyr Ile Ile Gly Asp Asp
                325                 330                 335

Asp Asn Lys Ala Thr Gln Val Tyr Thr Ile His Gly Tyr Gly Pro Ala
            340                 345                 350

Val Phe Asn Tyr Phe Pro Ser Leu Val Gln Ile Glu Gln Ser Ser Arg
        355                 360                 365

Gln Glu Glu Lys Ser
    370

<210> SEQ ID NO 5
<211> LENGTH: 384
<212> TYPE: PRT
<213> ORGANISM: Arabidopsis thaliana
<220> FEATURE:
<223> OTHER INFORMATION: thale cress ecotype Columbia F-box family
      protein, locus AT3G44120

<400> SEQUENCE: 5

Met Thr Leu Pro Glu Leu Pro Lys Asp Leu Val Glu Glu Ile Leu Cys
1               5                   10                  15

Phe Val Pro Ala Thr Ser Leu Lys Arg Leu Arg Ser Ser Cys Lys Glu
            20                  25                  30

Trp Asn Arg Leu Phe Lys Asp Asp Lys Arg Phe Ala Arg Lys His Ile
        35                  40                  45

Glu Lys Ala Ala Lys Gln Phe Gln Pro Leu Thr Leu Thr Lys Asn Tyr
    50                  55                  60

Arg Ile Cys Pro Ile Asn Val Asn Leu His Gly Thr Thr Pro Ser Leu
65                  70                  75                  80

Glu Val Lys Asn Glu Val Ser Leu Val Asp Pro His Ser Lys Asn Ser
                85                  90                  95

Ala Ala Gln Phe Asn Ile Asp Arg Val Phe His Cys Asp Gly Leu Leu
            100                 105                 110

Leu Cys Thr Ser Gln Lys Asp Ser Arg Phe Val Val Trp Asn Pro Leu
        115                 120                 125

Thr Gly Val Thr Lys Trp Ile Glu Leu Gly Asp Arg Tyr Asn Glu Gly
    130                 135                 140

Met Ala Phe Ile Leu Gly Tyr Asp Asn Lys Ser Cys Asn Lys Ser Tyr
145                 150                 155                 160

Lys Ala Met Ser Phe Asn Tyr Leu Asp Lys Asp Ser Glu Ile Tyr Glu
                165                 170                 175

Phe Ser Ser Asp Ser Trp Arg Val Ile Asp Asp Ile Ile Lys Pro Pro
            180                 185                 190
```

```
His Tyr Met Asp Tyr Phe Arg Glu Cys Phe Ser Leu Lys Gly Asn Thr
            195                 200                 205

Tyr Trp Leu Gly Ile Asp Arg Arg Arg Pro Pro Asp Leu Arg Ile
210                 215                 220

Thr Leu Ile Lys Phe Asp Phe Gly Thr Glu Arg Phe Gly Tyr Val Ser
225                 230                 235                 240

Leu Pro Pro Pro Cys Gln Val His Gly Phe Glu Ala Ser Asn Leu Ser
                245                 250                 255

Val Val Gly Asp Glu Lys Leu Ser Leu Val Gln Gly Gly Ser Thr
            260                 265                 270

Ser Lys Thr Glu Val Trp Val Thr Ser Lys Ile Gly Glu Ala Asn Val
            275                 280                 285

Val Ser Trp Ser Lys Val Leu Ser Leu Tyr Pro Lys Pro Asp Val Gly
290                 295                 300

Phe Trp His Gly Leu Ser Phe Leu Leu Asp Glu Lys Lys Val Val
305                 310                 315                 320

Leu Cys Cys Lys Ser Lys Gly Trp Met Glu Glu Asp Glu Glu Asn
            325                 330                 335

Val Tyr Ser Val Gly Glu Asp Thr Lys Phe Ile Leu Leu Asn Phe Gly
            340                 345                 350

Val Gln Thr Ile Gly Gly Tyr Ser Pro Ile Ile Val Asn Tyr Val Pro
            355                 360                 365

Ser Leu Gly Gln Ile Glu Leu Ala Gly Ser Lys Arg Lys Arg Asp Tyr
            370                 375                 380

<210> SEQ ID NO 6
<211> LENGTH: 384
<212> TYPE: PRT
<213> ORGANISM: Arabidopsis thaliana
<220> FEATURE:
<223> OTHER INFORMATION: thale cress ecotype Columbia hypothetical
      protein, F-box family protein, locus AT2G017140, T25N22.10

<400> SEQUENCE: 6

Met Thr Leu Pro Glu Leu Pro Lys Asp Leu Val Glu Glu Ile Leu Ser
1               5                   10                  15

Phe Val Pro Ala Thr Ser Leu Lys Arg Leu Arg Ser Thr Cys Lys Gly
            20                  25                  30

Trp Asn Arg Leu Phe Lys Asp Asp Lys Arg Phe Thr Arg Ile His Thr
        35                  40                  45

Glu Lys Ala Ala Lys Gln Phe Gln Pro Leu Thr Leu Thr Lys Asn Tyr
50                  55                  60

Arg Ile Cys Pro Ile Asn Val Asn Leu His Gly Thr Thr Pro Ser Leu
65                  70                  75                  80

Glu Val Lys Asn Glu Val Ser Leu Leu Asp Pro His Ser Lys Asn Ser
                85                  90                  95

Ala Ala Gln Phe Asn Ile Asp Arg Val Phe His Cys Asp Gly Leu Leu
            100                 105                 110

Leu Cys Thr Ser Gln Lys Asp Ser Arg Phe Val Val Trp Asn Pro Leu
        115                 120                 125

Thr Gly Val Thr Lys Trp Ile Glu Leu Gly Asp Arg Tyr Asn Glu Gly
130                 135                 140

Met Ala Phe Ile Leu Gly Tyr Asp Asn Lys Ser Cys Asn Lys Ser Tyr
145                 150                 155                 160

Lys Ala Met Ser Phe Asn Tyr Leu Asp Lys Asp Ser Glu Ile Tyr Glu
                165                 170                 175
```

```
Phe Ser Ser Asp Ser Trp Arg Val Ile Asp Asp Ile Ile Lys Pro Pro
            180                 185                 190

His Tyr Met Asp Tyr Phe Arg Glu Cys Phe Ser Leu Lys Gly Asn Thr
        195                 200                 205

Tyr Trp Leu Gly Ile Asp Arg Arg Arg Pro Pro Asp Leu Arg Ile
    210                 215                 220

Thr Leu Ile Lys Phe Asp Phe Gly Thr Glu Lys Phe Gly Tyr Val Ser
225                 230                 235                 240

Leu Pro Pro Pro Cys Gln Val His Gly Phe Glu Ala Ser Asn Leu Ser
                245                 250                 255

Val Val Gly Asp Glu Lys Leu Ser Val Leu Val Gln Ala Gly Ser Thr
            260                 265                 270

Ser Lys Thr Glu Val Trp Val Thr Ser Lys Ile Gly Glu Ala Asn Val
        275                 280                 285

Val Ser Trp Ser Lys Val Leu Ser Leu Tyr Pro Lys Pro Asp Val Gly
    290                 295                 300

Phe Trp His Gly Leu Ser Phe Leu Leu Asp Glu Lys Lys Val Phe
305                 310                 315                 320

Leu Cys Cys Lys Ser Lys Gly Trp Met Glu Glu Glu Asp Glu Asp Asn
                325                 330                 335

Val Tyr Ile Val Gly Glu Asp Asn Lys Phe Ile Leu Leu Asn Phe Gly
            340                 345                 350

Val Glu Thr Ile Gly Gly Glu Ser Pro Ile Ile Thr Thr Tyr Val Pro
        355                 360                 365

Ser Leu Val Gln Ile Glu Leu Ala Gly Ser Lys Arg Lys Thr Asp Tyr
    370                 375                 380

<210> SEQ ID NO 7
<211> LENGTH: 376
<212> TYPE: PRT
<213> ORGANISM: Arabidopsis thaliana
<220> FEATURE:
<223> OTHER INFORMATION: thale cress ecotype Columbia F-box family
      protein, locus AT3G18330

<400> SEQUENCE: 7

Met Pro Met Pro Asn Leu Pro Lys Glu Leu Glu Glu Ile Leu Ser
1               5                   10                  15

Phe Val Pro Ala Thr Tyr Leu Lys Arg Leu Ser Ala Thr Cys Lys Pro
            20                  25                  30

Trp Asn Arg Leu Ile His Asn Asp Lys Arg Phe Ala Arg Lys His Tyr
        35                  40                  45

Asp Asn Ala Ala Lys Glu Phe Leu Val Phe Met Met Arg Lys Asn Phe
    50                  55                  60

Arg Ile Ile Arg Arg Gly Val Asn Leu His Gly Ala Asp Pro Ser Ala
65                  70                  75                  80

Glu Val Lys Gly Glu Leu Thr Leu Pro Asp Pro Tyr Phe Lys Asn Ser
                85                  90                  95

Ala Asp Glu Phe His Ile Asp Arg Val Phe His Cys Asp Gly Leu Leu
            100                 105                 110

Leu Cys Thr Ser Lys Leu Glu Arg Arg Met Val Val Trp Asn Pro Leu
        115                 120                 125

Thr Gly Glu Thr Lys Trp Ile Gln Thr His Glu Glu Gly Asp Asn Phe
    130                 135                 140

Phe Leu Gly Tyr Ser Gln Glu Asp Lys Asn Ile Ser Cys Lys Lys Ser
```

```
                    145                 150                 155                 160

Tyr Lys Ile Met Gly Phe Tyr Arg Ser Gly Ser Lys Val Trp Glu Tyr
                165                 170                 175

Asp Phe Asn Ser Asp Ser Trp Arg Val Leu Asn Gly Ile Leu Pro Asn
                180                 185                 190

Trp Tyr Phe Asp Lys Ser Tyr Lys Cys Val Ser Leu Lys Gly Asn Thr
                195                 200                 205

Tyr Met Leu Ala Gly Ala Val Thr Asp Met Gly Phe Asp Leu Ser Leu
            210                 215                 220

Gln Ser Tyr Asp Phe Ser Thr Glu Lys Phe Ala Pro Val Ser Leu Pro
225                 230                 235                 240

Val Pro Ser Gln Ala Arg Ser Leu Asn Gly Ala Asn Arg Leu Ser Val
                245                 250                 255

Val Arg Gly Glu Lys Leu Ala Leu Leu Tyr Arg Arg Asp Lys Arg Ser
                260                 265                 270

Lys Ala Glu Ile Trp Val Thr Asn Lys Ile Asp Asp Thr Thr Glu Gly
                275                 280                 285

Ala Val Ser Trp Thr Lys Val Leu Glu Leu Asp Leu Ser Arg Glu Leu
            290                 295                 300

His Ala Leu Phe Thr Ser Asn Phe Leu Val Asp Glu Glu Lys Lys Val
305                 310                 315                 320

Phe Ile Cys Cys Val Ser Trp Lys Glu Asp Glu Asp Gly Asn Lys Ser
                325                 330                 335

Asn Lys Val Tyr Ile Val Gly Glu Asp Asn Ile Val Lys Glu Ile Asp
                340                 345                 350

Ser Gly Glu Asp Ala Thr Ser Gly Cys Glu Pro Thr Ile Leu Ser Leu
                355                 360                 365

Tyr Val Pro Ser Leu Val Tyr Met
                370                 375

<210> SEQ ID NO 8
<211> LENGTH: 815
<212> TYPE: PRT
<213> ORGANISM: Arabidopsis thaliana
<220> FEATURE:
<223> OTHER INFORMATION: thale cress ecotype Columbia hypothetical
      protein, F-box family protein, locus AT3G18900

<400> SEQUENCE: 8

Met Thr Thr Arg Thr Ser Asn His Lys Arg Ser Arg Ser Asp Pro Val
1               5                   10                  15

Pro Arg Lys Ser Leu Lys Asn Lys Lys Ser Ser Glu Ala Leu Tyr Asn
                20                  25                  30

Ile His Met Asp Glu Leu Leu Gln Arg Glu Ile Glu Gln Leu Lys Ser
            35                  40                  45

Leu Leu Lys Ser Arg Lys Leu His Pro Gly Gly Arg Arg Val Ser Ser
        50                  55                  60

Asp Glu Ile Asp Leu Leu Leu Gln Glu Asp Glu Val Leu Val Arg Arg
65                  70                  75                  80

Glu Met Lys Thr Val Leu Gly Arg Lys Leu Phe Leu Glu Asp Ser Lys
                85                  90                  95

Asn Glu Asp Ser Ser Ile Pro Lys Glu Ala Lys Lys Leu Val Glu Glu
                100                 105                 110

Ile Ala Gly Leu Glu Leu Gln Val Met Tyr Leu Glu Thr Tyr Leu Leu
            115                 120                 125
```

```
Leu Leu Tyr Arg Arg Phe Phe Asn Asn Lys Ile Thr Ser Lys Leu Glu
130                 135                 140

Ser Glu Glu Lys Glu Arg Ser Glu Asp Leu Leu Glu Cys Thr Lys Leu
145                 150                 155                 160

Ile Asp Ser Pro Lys Lys Gly Val Cys Ser Pro Gln Lys Leu Val Glu
                165                 170                 175

Asp Ser Gly Ile Phe Arg Ser His Ser Leu Ser His Cys Ser Gly
                180                 185                 190

Tyr Ser Phe Arg Met Ser Pro His Ala Met Asp Ser Ser Tyr His Arg
                195                 200                 205

Ser Leu Pro Phe Ser Met Leu Glu Gln Ser Asp Ile Asp Glu Leu Ile
210                 215                 220

Gly Thr Tyr Val Ser Glu Asn Val His Lys Ser Pro Asn Ser Leu Ser
225                 230                 235                 240

Glu Glu Met Val Lys Cys Ile Ser Glu Leu Cys Arg Gln Leu Val Asp
                245                 250                 255

Pro Gly Ser Leu Asp Asn Asp Leu Glu Ser Ser Pro Phe Arg Gly
                260                 265                 270

Lys Glu Pro Leu Lys Ile Ile Ser Arg Pro Tyr Asp Lys Leu Leu Met
                275                 280                 285

Val Lys Ser Ile Ser Arg Asp Ser Glu Lys Leu Asn Ala Val Glu Pro
290                 295                 300

Ala Leu Lys His Phe Arg Ser Leu Val Asn Lys Leu Glu Gly Val Asn
305                 310                 315                 320

Pro Arg Lys Leu Asn His Glu Glu Lys Leu Ala Phe Trp Ile Asn Ile
                325                 330                 335

His Asn Ser Leu Val Met His Ser Ile Leu Val Tyr Gly Asn Pro Lys
                340                 345                 350

Asn Ser Met Lys Arg Val Ser Gly Leu Leu Lys Ala Ala Tyr Asn Val
                355                 360                 365

Gly Gly Arg Ser Leu Asn Leu Asp Thr Ile Gln Thr Ser Ile Leu Gly
370                 375                 380

Cys Arg Val Phe Arg Phe Leu Phe Ala Ser Arg Ser Lys Gly Arg Ala
385                 390                 395                 400

Gly Asp Leu Gly Arg Asp Tyr Ala Ile Thr His Arg Glu Ser Leu Leu
                405                 410                 415

His Phe Ala Leu Cys Ser Gly Ser Leu Ser Asp Pro Ser Asn Val Met
                420                 425                 430

Met Glu Leu Glu Cys Gly Arg Glu Glu Tyr Val Arg Ser Asn Leu Gly
                435                 440                 445

Ile Ser Lys Asp Asn Lys Ile Leu Leu Pro Lys Leu Val Glu Ile Tyr
450                 455                 460

Ala Lys Asp Thr Glu Leu Cys Asn Val Gly Val Leu Asp Met Ile Gly
465                 470                 475                 480

Lys Cys Leu Pro Cys Glu Ala Arg Asp Arg Ile Gln Lys Cys Arg Asn
                485                 490                 495

Lys Lys His Gly Arg Phe Ser Ile Asp Trp Ile Ala His Asp Phe Arg
                500                 505                 510

Phe Gly Asn Asp Tyr Arg Ile Phe Pro Ser Ser Phe Asn Leu His Gly
                515                 520                 525

Thr Ser Pro Ser Val Glu Phe Lys Ser Glu Leu Ile Asp Pro His Ser
530                 535                 540

Lys Asn Ser Ala Ala Pro Phe Glu Ile Ser Arg Val Phe His Cys Asp
```

```
                545                 550                 555                 560
Gly Leu Leu Leu Cys Thr Ser His Phe Asp Ala Ser Arg Val Leu Val
                565                 570                 575

Trp Asn Pro Leu Thr Gly Glu Pro Asp Asn Asn Cys Cys Asn Lys Ser
                580                 585                 590

Tyr Lys Ile Leu Ser Ser His Gln Arg Ser Glu Tyr Phe Asp Ile Tyr
                595                 600                 605

Asp Phe Asn Ser Asp Ser Trp Arg Phe Val Glu Asp Met Ile Pro Pro
                610                 615                 620

Gly Val Ser Phe Gly Tyr Ser Glu Leu Ser Val Ser Leu Lys Gly Asn
625                 630                 635                 640

Thr Tyr Trp Leu Ala Ile Val Val Thr Glu Thr Pro Arg Thr Ile Ser
                645                 650                 655

Leu Leu Lys Phe Asp Phe Ser Ile Glu Lys Ser Val Leu Val Pro Leu
                660                 665                 670

Pro Tyr His Ser Leu Gln Ser Arg Arg Phe Glu Ala Ser Ser Leu Ser
                675                 680                 685

Val Val Arg Glu Glu Lys Leu Ser Val Leu Gln Arg Asp Ile Ser
690                 695                 700

Ser Lys Thr Glu Ile Trp Val Thr Ser Lys Ile Asp Asp Thr Thr Lys
705                 710                 715                 720

Val Val Ser Trp Ser Lys Ile Leu Ala Leu Asp Leu Ser Pro His Leu
                725                 730                 735

Gln Ile Trp Asn Asp Ala Ser Phe Leu Ile Gly Glu Glu Lys Lys Val
                740                 745                 750

Ile Met Cys Glu Arg Leu Val Asp Val His Thr Ser Lys Val Met Val
                755                 760                 765

Tyr Ile Val Gly Glu Asn Asn Val Val Thr Gln Val Glu Phe Gly Val
                770                 775                 780

Val Glu Met Asp Gly Cys Trp Ala Val Ile Phe Asn Tyr Val Pro Ser
785                 790                 795                 800

Leu Ile Gln Ile Glu Gln Ala Gly Gly Asn Arg Asn Ile Gly Lys
                805                 810                 815

<210> SEQ ID NO 9
<211> LENGTH: 1316
<212> TYPE: PRT
<213> ORGANISM: Solanum lycopersicum
<220> FEATURE:
<223> OTHER INFORMATION: tomato (Lycopersicon esculentum) cultivar Ailsa
      Craig ethylene signaling protein (EIN2, LeEIN2)

<400> SEQUENCE: 9

Met Glu Ser Glu Thr Leu Thr Arg Glu Tyr Arg Arg Pro Ser Met Leu
1               5                   10                  15

Gln Arg Val Leu Ser Ala Ser Val Pro Met Leu Leu Ile Ala Val Gly
                20                  25                  30

Tyr Val Asp Pro Gly Lys Trp Ala Ala Met Val Asp Gly Gly Ala Arg
                35                  40                  45

Phe Gly Phe Asp Leu Val Met Leu Val Leu Phe Asn Phe Ala Ala
            50                  55                  60

Ile Leu Cys Gln Tyr Leu Ser Ala Cys Ile Ala Leu Val Thr Asp Arg
65                  70                  75                  80

Asp Leu Ala Gln Ile Cys Ser Glu Glu Tyr Asp Lys Val Thr Cys Ile
                85                  90                  95
```

```
Phe Leu Gly Ile Gln Ala Glu Val Ser Met Ile Ala Leu Asp Leu Thr
            100                 105                 110

Met Val Leu Gly Thr Ala His Gly Leu Asn Val Phe Gly Val Asp
        115                 120                 125

Leu Phe Ser Cys Val Phe Leu Thr Ala Thr Gly Ala Ile Leu Phe Pro
        130                 135                 140

Leu Leu Ala Ser Leu Leu Asp Asn Gly Ser Ala Lys Phe Leu Cys Ile
145                 150                 155                 160

Gly Trp Ala Ser Ser Val Leu Leu Ser Tyr Val Phe Gly Val Val Ile
                165                 170                 175

Thr Leu Pro Glu Thr Pro Phe Ser Ile Gly Gly Val Leu Asn Lys Phe
                180                 185                 190

Ser Gly Glu Ser Ala Phe Ala Leu Met Ser Pro Leu Gly Ala Ser Ile
        195                 200                 205

Met Pro His Asn Phe Tyr Leu His Ser Ser Ile Val Gln Gln Gly Lys
        210                 215                 220

Glu Ser Thr Glu Leu Ser Arg Gly Ala Leu Cys Gln Asp His Phe Phe
225                 230                 235                 240

Ala Ile Val Phe Ile Phe Ser Gly Ile Phe Leu Val Asn Tyr Ala Ala
                245                 250                 255

Met Asn Ser Ala Ala Asn Val Ser Tyr Ser Thr Gly Leu Leu Leu Leu
        260                 265                 270

Thr Phe Gln Asp Thr Leu Ser Leu Leu Asp Gln Val Phe Arg Ser Ser
        275                 280                 285

Val Ala Pro Phe Thr Ile Met Leu Val Thr Phe Ile Ser Asn Gln Val
        290                 295                 300

Thr Pro Leu Thr Trp Asp Leu Gly Arg Gln Ala Val His Asp Leu
305                 310                 315                 320

Phe Gly Met Asp Ile Pro Gly Trp Leu His His Val Thr Ile Arg Val
                325                 330                 335

Ile Ser Ile Val Pro Ala Leu Tyr Cys Val Trp Ser Ser Gly Ala Glu
                340                 345                 350

Gly Leu Tyr Gln Leu Leu Ile Leu Thr Gln Val Val Val Ala Leu Val
        355                 360                 365

Leu Pro Ser Ser Val Ile Pro Leu Phe Arg Val Ala Ser Ser Arg Ser
        370                 375                 380

Ile Met Gly Ile His Lys Ile Ser Gln Leu Met Glu Phe Leu Ser Leu
385                 390                 395                 400

Gly Thr Phe Ile Gly Leu Leu Gly Leu Lys Ile Ile Phe Val Ile Glu
                405                 410                 415

Met Ile Phe Gly Asn Ser Asp Trp Val Asn Asn Leu Lys Trp Asn Ile
        420                 425                 430

Gly Ser Ser Val Ser Thr Pro Tyr Phe Phe Leu Leu Ile Ala Ala Ser
        435                 440                 445

Leu Cys Leu Cys Leu Met Leu Trp Leu Ala Val Thr Pro Leu Lys Ser
450                 455                 460

Ala Ser Ser Arg Phe Asp Ala Gln Ala Phe Leu Gln Thr His Val Pro
465                 470                 475                 480

Glu Pro Tyr Ser Glu Cys Asn Gln Leu Gly Ala Ser Asn Ala Met Phe
                485                 490                 495

Gly Leu Val Glu Gly Ser Ser Gln Lys Gln Glu Gly Ala Phe His Val
        500                 505                 510

Glu Lys Ser Leu Val Ser His Pro Asp Leu Ser Thr Lys Asp Pro Asp
```

```
            515                 520                 525
Gln Leu Leu Pro Glu Ser Leu Leu Asp Phe Glu Lys Val His Gln Leu
    530                 535                 540
Ala Thr Ile Asp Glu Ser Lys Ser Glu Thr Thr Phe Ser Ala Pro Ala
545                 550                 555                 560
Val Val His Pro Glu Val Pro Val Ser Ala Gly Ser Pro Ser Val
                565                 570                 575
Lys Ser Val Cys Asn Glu Val Ser Gly Val Val Ser Val Asp Thr Ser
            580                 585                 590
Val Phe Asn Thr Glu Thr Val Asp Val Ala Glu Lys Thr Leu Arg Ile
        595                 600                 605
Glu Gly Asp Met Ala Asn Asp Arg Asp Asp Gly Asp Ser Trp Glu Glu
    610                 615                 620
Pro Glu Glu Ala Ile Lys Gly Val Ser Glu Asn Ala Gln Ser Phe Ile
625                 630                 635                 640
Ser Asp Gly Pro Gly Ser Tyr Lys Ser Leu Ser Gly Lys Leu Glu Asp
                645                 650                 655
Thr Gly Ser Gly Thr Gly Ser Leu Ser Arg Leu Ala Gly Leu Gly Arg
            660                 665                 670
Ala Ala Arg Arg Gln Leu Thr Glu Ala Leu Asn Glu Phe Trp Gly Gln
        675                 680                 685
Leu Phe Asp Tyr His Gly Val Ala Thr Ala Glu Ala Lys Ser Lys Lys
    690                 695                 700
Leu Asp Ile Ile Leu Gly Leu Asp Ser Lys Met Asn Pro Lys Pro Ala
705                 710                 715                 720
Pro Ala Ser Leu Lys Val Glu Ser Ser Ala Tyr Ile Pro Ser Gly Ser
                725                 730                 735
Ala Arg Ile Pro Glu Pro Leu Ile Asn Ser His Val Tyr Ser Pro Lys
            740                 745                 750
Gln Gln Phe Ala Ser Asn Ile Val Asp Ser Ala Tyr Arg Val Pro Lys
        755                 760                 765
Glu Pro Ser Ser Thr Ser Ser Met Trp Ser Asn His Met Lys Leu Val
    770                 775                 780
Gly Ala Tyr Val Gln Ser Ser Asn Ser Asn Met Leu Asp Ser Gly Glu
785                 790                 795                 800
Arg Arg Tyr Ser Ser Met Arg Ile Pro Ala Thr Ser Ala Gly Tyr Asp
                805                 810                 815
Gln Gln Pro Ala Thr Val His Gly Tyr Gln Ile Thr Ala Tyr Leu Asn
            820                 825                 830
Gln Leu Ala Lys Glu Arg Gly Ser Asp Tyr Leu Asn Gly Gln Leu Glu
        835                 840                 845
Ser Pro Ser Pro Arg Ser Val Ser Ser Leu Thr Ser Asn Tyr Ala Glu
    850                 855                 860
Pro Leu Ala Arg Val Ser Gly Gln Lys Pro Gln Ser Gly Val Ser Ser
865                 870                 875                 880
Arg Ala Pro Pro Gly Phe Gly Asn Val Pro Val Gly Arg Asn Asn Ser
                885                 890                 895
Met Gln Pro Thr Asn Thr Thr Ser Val Asp His Ser Ser Thr Glu Thr
            900                 905                 910
Ala Glu Ser Val Ala Gly Ser Ala Asn Ser Lys Lys Tyr Tyr Ser Leu
        915                 920                 925
Pro Asp Ile Ser Gly Arg Tyr Val Pro Arg Gln Asp Ser Ile Val Ser
    930                 935                 940
```

Asp Ala Arg Ala Gln Trp Tyr Asn Ser Met Gly Phe Gly Gln Ser Gly
945                 950                 955                 960

Gly Arg Ser Thr Tyr Glu Gln Ala Tyr Met Ser Gly Ser Leu Arg Ala
            965                 970                 975

Gly Gly Pro Gln Arg Tyr Glu His Ser Pro Lys Val Cys Arg Asp Ala
            980                 985                 990

Phe Ser Leu Gln Tyr Ser Ser Asn Ser Gly Thr Gly Ser Leu Trp Ser
            995                 1000                1005

Arg Gln Pro Phe Glu Gln Phe Gly Val Ala Gly Lys Pro Asp Val Gly
    1010                1015                1020

Ser Gly Asp His Gly Thr Val Leu Ser Ser Ala Gln Glu Ser Thr
1025                1030                1035                1040

Ser Thr Val Asp Leu Glu Ala Lys Leu Leu Gln Ser Phe Arg Ser Cys
            1045                1050                1055

Ile Val Lys Leu Leu Lys Leu Glu Gly Ser Glu Trp Leu Phe Arg Gln
            1060                1065                1070

Asp Asp Gly Ala Asp Glu Asp Leu Ile Gly Arg Ile Ala Ala Arg Glu
            1075                1080                1085

Lys Phe Leu Tyr Glu Ala Glu Thr Arg Glu Ile Ser Arg Leu Thr Asn
    1090                1095                1100

Ile Gly Glu Ser His Phe Ser Ser Asn Arg Lys Pro Gly Ser Ala Pro
1105                1110                1115                1120

Lys Pro Glu Glu Met Asp Tyr Thr Lys Phe Leu Val Met Ser Val Pro
            1125                1130                1135

His Cys Gly Glu Gly Cys Val Trp Lys Val Asp Leu Ile Ile Ser Phe
            1140                1145                1150

Gly Val Trp Cys Ile His Arg Ile Leu Glu Leu Ser Leu Met Glu Ser
            1155                1160                1165

Arg Pro Glu Leu Trp Gly Lys Tyr Thr Tyr Val Leu Asn Arg Leu Gln
    1170                1175                1180

Gly Ile Val Asp Leu Ala Phe Ser Lys Pro His Ser Pro Thr Ser His
1185                1190                1195                1200

Cys Phe Cys Leu Gln Ile Pro Ala Gly Arg Gln Gln Lys Ala Ser Pro
            1205                1210                1215

Pro Pro Ile Ser Asn Gly Asn Leu Pro Pro Gln Ala Lys Gln Gly Arg
            1220                1225                1230

Gly Lys Cys Thr Thr Ala Ala Met Leu Leu Glu Met Ile Lys Asp Val
            1235                1240                1245

Glu Thr Ala Ile Ser Cys Arg Lys Gly Arg Thr Gly Thr Ala Ala Gly
    1250                1255                1260

Asp Val Ala Phe Pro Lys Gly Lys Glu Asn Leu Ala Ser Val Leu Lys
1265                1270                1275                1280

Arg Tyr Lys Arg Arg Leu Ser Asn Lys Pro Val Gly Asn Gln Glu Val
            1285                1290                1295

Ala Gly Val Ala Gly Pro Arg Lys Val Thr Leu Ser Ala Ser Ser Pro
            1300                1305                1310

Pro Phe Val Leu
        1315

<210> SEQ ID NO 10
<211> LENGTH: 881
<212> TYPE: PRT
<213> ORGANISM: Solanum lycopersicum
<220> FEATURE:

<223> OTHER INFORMATION: tomato (Lycopersicon esculentum)
       ethylene-insensitive 2 (EIN2, LeEIN2)

<400> SEQUENCE: 10

```
Val Ser Thr Pro Tyr Val Phe Leu Leu Ile Ala Ala Ser Leu Cys Leu
 1               5                  10                  15

Cys Leu Met Leu Trp Leu Ala Val Thr Pro Leu Lys Ser Ala Ser Ser
            20                  25                  30

Arg Phe Asp Ala Gln Ala Phe Leu Gln Thr His Val Pro Glu Pro Tyr
        35                  40                  45

Ser Glu Cys Asn Gln Leu Gly Ala Ser Asn Ala Met Phe Gly Leu Val
    50                  55                  60

Gly Gly Ser Ser Gln Lys Gln Glu Gly Ala Phe His Val Glu Lys Ser
65                  70                  75                  80

Leu Val Ser His Pro Asp Leu Ser Thr Lys Asp Pro Asp Gln Leu Leu
                85                  90                  95

Pro Glu Ser Leu Leu Asp Phe Glu Lys Val His Gln Leu Ala Thr Ile
            100                 105                 110

Asp Glu Ser Lys Ser Glu Thr Thr Phe Ser Ala Pro Ala Val Val His
        115                 120                 125

Pro Glu Val Pro Val Ser Ala Gly Ala Ser Pro Ser Val Lys Ser Val
    130                 135                 140

Cys Asn Glu Val Ser Gly Val Val Ser Val Asp Thr Ser Val Phe Asn
145                 150                 155                 160

Thr Glu Thr Val Asp Val Ala Glu Lys Thr Leu Arg Ile Glu Gly Asp
                165                 170                 175

Met Ala Asn Asp Arg Asp Asp Gly Asp Ser Trp Glu Glu Pro Glu Glu
            180                 185                 190

Ala Ile Lys Gly Val Ser Glu Asn Ala Gln Ser Phe Ile Ser Asp Gly
        195                 200                 205

Pro Gly Ser Tyr Lys Ser Leu Ser Gly Lys Leu Glu Asp Thr Gly Ser
    210                 215                 220

Gly Thr Gly Ser Leu Ser Arg Leu Ala Gly Leu Gly Arg Ala Ala Arg
225                 230                 235                 240

Arg Gln Leu Thr Glu Ala Leu Asn Glu Phe Trp Gly Gln Leu Phe Asp
                245                 250                 255

Tyr His Gly Val Ala Thr Ala Glu Ala Lys Ser Lys Lys Leu Asp Ile
            260                 265                 270

Ile Leu Gly Leu Asp Ser Lys Met Asn Pro Lys Pro Ala Pro Ala Ser
        275                 280                 285

Leu Lys Val Glu Ser Ser Ala Tyr Ile Pro Ser Gly Ser Ala Arg Ile
    290                 295                 300

Pro Glu Pro Leu Ile Asn Ser His Val Tyr Ser Pro Lys Gln Gln Phe
305                 310                 315                 320

Ala Ser Asn Ile Val Asp Ser Ala Tyr Arg Val Pro Lys Glu Pro Ser
                325                 330                 335

Ser Thr Ser Ser Met Trp Ser Asn His Met Lys Leu Val Gly Ala Tyr
            340                 345                 350

Val Gln Ser Ser Asn Ser Asn Met Leu Asp Ser Gly Glu Arg Arg Tyr
        355                 360                 365

Ser Ser Met Arg Ile Pro Ala Thr Ser Ala Gly Tyr Asp Gln Gln Pro
    370                 375                 380

Ala Thr Val His Gly Tyr Gln Ile Thr Ala Tyr Leu Asn Gln Leu Ala
385                 390                 395                 400
```

```
Lys Glu Arg Gly Ser Asp Tyr Leu Asn Gly Gln Leu Glu Ser Pro Ser
                405                 410                 415

Pro Arg Ser Val Ser Ser Leu Thr Ser Asn Tyr Ala Glu Pro Leu Ala
                420                 425                 430

Arg Val Ser Gly Gln Lys Pro Gln Ser Gly Val Ser Ser Arg Ala Pro
                435                 440                 445

Pro Gly Phe Gly Asn Val Pro Val Gly Arg Asn Asn Ser Met Gln Pro
            450                 455                 460

Thr Asn Thr Thr Ser Val Asp His Ser Ser Thr Glu Thr Ala Glu Ser
465                 470                 475                 480

Val Ala Gly Ser Ala Asn Ser Lys Lys Tyr Tyr Ser Leu Pro Asp Ile
                485                 490                 495

Ser Gly Arg Tyr Val Pro Arg Gln Asp Ser Ile Val Ser Asp Ala Arg
                500                 505                 510

Ala Gln Trp Tyr Asn Ser Met Gly Phe Gly Gln Ser Gly Gly Arg Ser
                515                 520                 525

Thr Tyr Glu Gln Ala Tyr Met Ser Gly Ser Leu Arg Ala Gly Gly Pro
                530                 535                 540

Gln Arg Tyr Glu His Ser Pro Lys Val Cys Arg Asp Ala Phe Ser Leu
545                 550                 555                 560

Gln Tyr Ser Ser Asn Ser Gly Thr Gly Ser Leu Trp Ser Arg Gln Pro
                565                 570                 575

Phe Glu Gln Phe Gly Val Ala Gly Lys Pro Asp Val Gly Ser Gly Asp
                580                 585                 590

His Gly Thr Val Leu Ser Ser Ala Gln Glu Ser Thr Ser Thr Val
                595                 600                 605

Asp Leu Glu Ala Lys Leu Leu Gln Ser Phe Arg Ser Cys Ile Val Lys
610                 615                 620

Leu Leu Lys Leu Glu Gly Ser Glu Trp Leu Phe Arg Gln Asp Asp Gly
625                 630                 635                 640

Ala Asp Glu Asp Leu Ile Gly Arg Ile Ala Ala Arg Glu Lys Phe Leu
                645                 650                 655

Tyr Glu Ala Glu Thr Arg Glu Ile Ser Arg Leu Thr Asn Ile Gly Glu
                660                 665                 670

Ser His Phe Ser Ser Asn Arg Lys Pro Gly Ser Ala Pro Lys Pro Glu
                675                 680                 685

Glu Met Asp Tyr Thr Lys Phe Leu Val Met Ser Val Pro His Cys Gly
            690                 695                 700

Glu Gly Cys Val Trp Lys Val Asp Leu Ile Ile Ser Phe Gly Val Trp
705                 710                 715                 720

Cys Ile His Arg Ile Leu Glu Leu Ser Leu Met Glu Ser Arg Pro Glu
                725                 730                 735

Leu Trp Gly Lys Tyr Thr Tyr Val Leu Asn Arg Leu Gln Gly Ile Val
                740                 745                 750

Asp Leu Ala Phe Ser Lys Pro His Ser Pro Thr Ser His Cys Phe Cys
                755                 760                 765

Leu Gln Ile Pro Ala Gly Arg Gln Gln Lys Ala Ser Pro Pro Ile
            770                 775                 780

Ser Asn Gly Asn Leu Pro Pro Gln Ala Lys Gln Gly Arg Gly Lys Cys
785                 790                 795                 800

Thr Thr Ala Ala Met Leu Leu Glu Met Ile Lys Asp Val Glu Thr Ala
                805                 810                 815
```

-continued

Ile Ser Cys Arg Lys Gly Arg Thr Thr Ala Ala Gly Asp Val Ala
            820             825             830

Phe Pro Lys Gly Lys Glu Asn Leu Ala Ser Val Leu Lys Arg Tyr Lys
835             840             845

Arg Arg Leu Ser Asn Lys Pro Val Gly Asn Gln Glu Val Ala Gly Val
850             855             860

Ala Gly Pro Arg Lys Val Thr Leu Ser Ala Ser Ser Pro Phe Val
865             870             875             880

Leu

<210> SEQ ID NO 11
<211> LENGTH: 1310
<212> TYPE: PRT
<213> ORGANISM: Petunia x hybrida
<220> FEATURE:
<223> OTHER INFORMATION: petunia ethylene signaling protein (EIN2, PhEIN2)

<400> SEQUENCE: 11

Met Glu Ser Glu Thr Gln Thr Ile Ala Tyr Arg Gln Pro Ser Met Leu
1               5                   10                  15

Gln Arg Ile Leu Ser Ala Ser Met Pro Met Leu Leu Ile Ala Ile Gly
            20                  25                  30

Tyr Val Asp Pro Gly Lys Trp Ala Ala Met Val Asp Gly Gly Ala Arg
        35                  40                  45

Phe Gly Phe Asp Leu Ile Met Leu Ala Leu Phe Asn Phe Ala Ala
    50                  55                  60

Ile Leu Cys Gln Tyr Leu Ser Ala Cys Ile Ala Leu Val Thr Asp Gln
65              70                  75                  80

Asp Leu Ala Gln Ile Cys Ser Glu Glu Tyr Gly Lys Val Thr Cys Ile
                85                  90                  95

Phe Leu Gly Ile Gln Ala Glu Val Ser Met Ile Ala Leu Asp Leu Thr
            100                 105                 110

Met Val Leu Gly Thr Ala His Gly Leu Asn Val Val Phe Gly Val Asp
        115                 120                 125

Leu Phe Ser Cys Val Phe Leu Ala Ala Thr Gly Ala Ile Leu Phe Pro
    130                 135                 140

Leu Leu Ala Ser Leu Leu Asp Asn Gly Ser Ala Lys Phe Ile Cys Ile
145             150                 155                 160

Gly Trp Ala Ser Ser Ile Leu Leu Ser Tyr Val Phe Gly Val Val Ile
                165                 170                 175

Ser Gln Pro Glu Ser Pro Phe Ser Ile Gly Gly Met Leu Asn Lys Phe
            180                 185                 190

Ser Gly Glu Ser Ala Phe Ala Leu Met Ser Leu Leu Gly Ala Ser Ile
        195                 200                 205

Met Pro His Asn Phe Tyr Leu His Ser Ser Ile Val Gln Gln Gly Lys
    210                 215                 220

Glu Ser Thr Asn Leu Ser Arg Gly Ala Leu Cys Gln Asp His Phe Phe
225             230                 235                 240

Ala Ile Val Phe Val Phe Ser Gly Ile Phe Leu Val Asn Tyr Ala Ile
                245                 250                 255

Met Asn Ser Ala Ala Asn Val Ser Phe Ser Thr Gly Leu Leu Leu Leu
            260                 265                 270

Thr Phe Gln Asp Ser Leu Ser Leu Leu Asp Gln Val Phe Arg Ser Ser
        275                 280                 285

```
Val Ala Pro Phe Ser Ile Met Leu Val Thr Phe Ile Ser Asn Gln Ile
    290                 295                 300

Thr Pro Leu Thr Trp Asp Leu Gly Arg Gln Ala Val His Asp Leu
305                 310                 315                 320

Phe Gly Met Asp Ile Pro Gly Trp Leu His His Val Thr Ile Arg Val
                325                 330                 335

Ile Ser Val Val Pro Ala Leu Tyr Cys Val Trp Asn Ser Gly Ala Glu
        340                 345                 350

Gly Leu Tyr Gln Leu Leu Ile Val Thr Gln Val Val Ala Leu Val
        355                 360                 365

Leu Pro Ser Ser Val Ile Pro Leu Phe Arg Val Ala Ser Ser Arg Ser
370                 375                 380

Ile Met Gly Ile His Lys Ile Ser Gln Leu Met Glu Phe Leu Ser Leu
385                 390                 395                 400

Gly Thr Phe Ile Gly Leu Leu Gly Leu Lys Ile Ile Phe Val Ile Glu
                405                 410                 415

Met Ile Phe Gly Asn Ser Asp Trp Val Asn Asn Leu Lys Trp Ser Ile
            420                 425                 430

Gly Ser Gly Val Ser Thr Pro Tyr Val Phe Leu Leu Ile Ala Ala Ser
        435                 440                 445

Leu Ser Leu Cys Leu Met Leu Trp Leu Ala Val Thr Pro Leu Lys Ser
450                 455                 460

Ala Ser Ser Arg Phe Asp Ala Gln Ala Phe Leu Gln Thr Pro Met Pro
465                 470                 475                 480

Glu Ser Tyr Arg Glu His Asn Gln Val Asp Val Ser Asp Thr Thr Phe
                485                 490                 495

Gly Leu Glu Arg Ser Thr Gln Lys Gln Glu Pro Ala Phe His Val Glu
            500                 505                 510

Lys Ser Leu Gly Ser His Pro Asp Leu Ser Thr Ser Asp Pro Asp Glu
        515                 520                 525

Ile Leu Pro Glu Ser Leu Leu Asp Phe Glu Lys Val His His Leu Thr
530                 535                 540

Thr Ile Asp Glu Ser Lys Ser Glu Thr Thr Phe Ser Thr Pro Ser Phe
545                 550                 555                 560

Ser Cys Pro Glu Val Ser Ala Ser Ala Gly Glu Thr Ala Lys Ser Val
                565                 570                 575

Leu Asn Glu Val Ser Gly Gly Glu Ser Val Asp Thr Arg Asp Phe Asn
            580                 585                 590

Ala Ala Ser Val Asp Val Glu Lys Thr Leu Arg Ile Glu Gly Asp
        595                 600                 605

Thr Pro Thr Asp Lys Asp Asp Gly Asp Ser Trp Glu Pro Asp Asp
610                 615                 620

Val Pro Lys Asp Val Ser Glu Asn Thr Gln Ser Tyr Thr Ser Asp Gly
625                 630                 635                 640

Pro Glu Ser Phe Lys Ser Leu Ser Val Arg Ser Glu Asp Thr Gly Ser
                645                 650                 655

Gly Thr Gly Ser Leu Ser Arg Leu Ala Gly Leu Gly Arg Ala Ala Arg
            660                 665                 670

Arg Gln Leu Thr Val Val Leu Asp Glu Phe Trp Gly Gln Leu Phe Asp
        675                 680                 685

Tyr His Gly Met Pro Thr Ser Gln Ala Lys Phe Lys Lys Leu Asp Val
        690                 695                 700

Ile Leu Gly Leu Asp Thr Lys Val Asp Pro Lys Pro Ala Pro Val Ser
```

```
                705                 710                 715                 720
Leu Lys Leu Glu Asn Ser Arg Gly Asp Ser Asn Ala Tyr Ile Pro Ser
                    725                 730                 735

Gly Ser Ala Arg Val Pro Glu Ser Trp Ile Asn Ser Asn Ile Tyr Ser
                740                 745                 750

Pro Lys Gln Gln Cys Ala Ser Gly Ala Leu Asp Ser Gly Tyr Arg Val
                755                 760                 765

Pro Lys Glu Pro Ala Ser Trp Ser Ser His Met Lys Leu Leu Asp Ala
            770                 775                 780

Tyr Val Gln Ser Ser Gly Asn Thr Leu Asp Ser Gly Glu Arg Arg
785                 790                 795                 800

Tyr Ser Ser Met Arg Ile Pro Ala Ser Ala Gly Tyr Asp Gln Gln
                805                 810                 815

Pro Ala Thr Val His Gly Tyr Gln Ile Ser Ala Tyr Leu Ser Gln Ile
                820                 825                 830

Ala Lys Gly Arg Gly Ser Asp Tyr Leu Asn Gly Gln Leu Glu Ser Ala
            835                 840                 845

Ser Pro Arg Ser Val Ser Ser Leu Thr Ser Asn His Ala Glu Pro Leu
        850                 855                 860

Ala Arg Ala Leu Gly Gln Lys Pro Gln Ser Gly Val Ser Ser Arg Ala
865                 870                 875                 880

Pro Pro Gly Phe Gly Ser Val Pro Ala Arg Asn Asn Ser Met Gln Pro
                885                 890                 895

Val Asn Thr Ser Thr Asp Leu Ser Ser Thr Glu Asn Ala Glu Ser Val
                900                 905                 910

Ala Gly Ser Ala Asn Ser Lys Lys Tyr Tyr Ser Leu Pro Asp Ile Ser
            915                 920                 925

Gly Arg Tyr Val Pro Arg Gln Asp Ser Ser Leu Pro Asp Gly Arg Ala
        930                 935                 940

Gln Trp Tyr Asn Ser Met Gly Tyr Gly Gln Ser Ile Gly Arg Ser Ala
945                 950                 955                 960

Tyr Glu Gln Pro Tyr Met Thr Gly Pro Met Arg Ala Gly Gly Pro Pro
                965                 970                 975

Arg Phe Glu His Ser Pro Ser Lys Val Cys Arg Asp Ala Phe Thr Leu
            980                 985                 990

Gln Tyr Ser Ser Asn Ser Gly Thr Gly Ser Leu Trp Ser Arg Gln Pro
        995                 1000                1005

Phe Glu Gln Phe Gly Val Ala Gly Lys Ala Asp Val Ser Ser Asp His
    1010                1015                1020

Gly Thr Val Gln Ser Ser Ser Thr Gln Glu Ser Thr Ser Leu Val Asp
1025                1030                1035                1040

Leu Glu Ala Lys Leu Leu Gln Ser Phe Arg Ser Cys Ile Val Lys Leu
                1045                1050                1055

Leu Lys Leu Glu Gly Ser Glu Trp Leu Phe Arg Gln Asp Asp Gly Ala
                1060                1065                1070

Asp Glu Asp Leu Ile Asp Arg Ile Ala Ala Arg Glu Lys Phe Leu Tyr
            1075                1080                1085

Glu Ala Glu Thr Arg Glu Ile Ser Arg Leu Thr Asn Ile Gly Glu Ser
        1090                1095                1100

Gln Phe Ser Ser Asn Arg Lys Pro Gly Ser Ala Gln Lys Pro Glu Glu
1105                1110                1115                1120

Met Asp Tyr Thr Lys Phe Leu Val Met Ser Val Pro His Cys Gly Glu
                1125                1130                1135
```

-continued

```
Gly Cys Val Trp Lys Val Asp Leu Val Val Ser Phe Gly Val Trp Cys
            1140                1145                1150

Ile His Arg Ile Leu Glu Leu Ser Leu Met Glu Ser Arg Pro Glu Leu
        1155                1160                1165

Trp Gly Lys Tyr Thr Tyr Cys Leu Asn Arg Leu Gln Gly Ile Val Asp
    1170                1175                1180

Leu Ala Phe Ser Lys Pro Arg Ser Pro Thr Ser His Cys Phe Cys Leu
1185                1190                1195                1200

Gln Ile Pro Ile Gly Arg Gln Gln Lys Ser Ser Pro Thr Pro Ile Ser
            1205                1210                1215

Asn Gly Ser Leu Pro Pro Gln Ala Lys Gln Gly Arg Gly Lys Cys Thr
        1220                1225                1230

Thr Ala Pro Met Leu Leu Asp Met Ile Lys Asp Val Glu Met Ala Ile
    1235                1240                1245

Ser Cys Arg Lys Gly Arg Thr Gly Thr Ala Ala Gly Asp Val Ala Phe
1250                1255                1260

Pro Lys Gly Lys Glu Asn Leu Ala Ser Val Leu Lys Arg Tyr Lys Arg
1265                1270                1275                1280

Arg Leu Ser Asn Lys Pro Val Gly Asn Gln Glu Ala Gly Gly Pro
            1285                1290                1295

Gln Arg Lys Val Thr Ser Pro Ser Ser Thr Ser Phe Gly Leu
        1300                1305                1310

<210> SEQ ID NO 12
<211> LENGTH: 620
<212> TYPE: PRT
<213> ORGANISM: Prunus persica
<220> FEATURE:
<223> OTHER INFORMATION: peach ethylene signaling protein (EIN2, PpEIN2)

<400> SEQUENCE: 12

Leu Asp Glu Phe Trp Gly Gln Leu Tyr Asp Phe His Gly Asn Val Ile
 1               5                  10                  15

Gln Glu Ala Lys Ala Lys Lys Leu Asp Leu Leu Leu Gly Leu Asp Ser
            20                  25                  30

Lys Ala Ala Ser Ser Ser Leu Lys Val Asp Thr Ser Ala Lys Glu Leu
        35                  40                  45

Ser Gly Tyr Phe Pro Ser Ala Gly Gly Arg Gly Ser Asp Pro Ile Met
    50                  55                  60

Asn Ser Ser Leu Tyr Asp Ser Pro Lys Gln Gln Arg Val Gln Ser Ser
65                  70                  75                  80

Leu Glu Ser Tyr Gly Val Gln Arg Gly Ser Ser Ala Leu Leu Pro Ser
                85                  90                  95

Arg Val Gln Leu Leu Asp Ala Tyr Val Gln Asn Ser Ser Arg Ser Val
            100                 105                 110

Ile Asp Ser Gly Glu Arg Arg Tyr Ser Ser Val Arg Ser Leu Pro Ser
        115                 120                 125

Ser Glu Ser Trp Asp Tyr Gln Pro Ala Thr Ile His Ser Tyr His Pro
    130                 135                 140

Ser Tyr Leu Asn Arg Ile Ala Lys Asp Arg Gly Phe Asp Asn Leu Asn
145                 150                 155                 160

Gly Gln Met Glu Ser Ala Ala Leu Gln Ser Ala Ser Ser Leu Gly Ala
                165                 170                 175

Ala Asn Tyr Arg Asp Ser Leu Ala Phe Thr Met Gly Gln Lys Leu Gln
            180                 185                 190
```

```
Asn Gly Leu Gly Ser Gly Gln Ala Ser Ile Phe Gln Asn His Thr Val
        195                 200                 205

Ser Arg Asn Ser Pro Leu Gln Ser Glu Arg Pro Tyr Tyr Asp Leu His
    210                 215                 220

Pro Ser Gly Ile Ala Glu Asn Val Val Ser Ser Ala Asn Ala Lys Lys
225                 230                 235                 240

Tyr His Ser Leu Pro Asp Ile His Arg Asp Leu Tyr Met Pro Glu Lys
                245                 250                 255

Ser Ala Asn Trp Glu Ser Pro Val Gly Tyr Gly Ser Ser Thr Gly Ile
                260                 265                 270

Thr Asn Tyr Glu Ser Ser Leu Tyr Ser Asn Ser Gly Ala Arg Thr Gly
            275                 280                 285

Ala Pro Leu Ala Phe Asp Gln Leu Ser Pro Ser Gln Val Tyr Arg Asp
290                 295                 300

Ala Phe Ser Ser Gln Gln Asn Ser Ser Phe Asn Thr Gly Ser Leu Trp
305                 310                 315                 320

Ser Arg Gln Pro Phe Glu Gln Phe Gly Val Ala Asp Asn Asn Arg Thr
                325                 330                 335

Ile Gly Ser Gly Gly Phe Gly Tyr Arg Ala Gly Ser Val Ser Gln Glu
                340                 345                 350

Ala Thr Ser Val Ala Asp Ser Glu Ala Lys Leu Leu Gln Ser Leu Arg
            355                 360                 365

His Cys Ile Val Lys Leu Leu Lys Leu Glu Gly Ser Asp Trp Leu Phe
        370                 375                 380

Thr Gln Asn Gly Gly Val Asp Glu Asp Leu Ile Asp Arg Val Ala Ala
385                 390                 395                 400

Arg Glu Lys Phe Leu Tyr Glu Ala Glu Thr Arg Glu Met Asn Arg Thr
                405                 410                 415

Val His Met Gly Glu Pro Gln Tyr His Pro Ser Asp Arg Lys Ser Val
                420                 425                 430

Ser Ala Leu Lys Asn Asn Asp Ala Asn Cys Thr Ser Phe Met Val Pro
            435                 440                 445

Thr Cys Gly Glu Gly Cys Ile Trp Arg Ser Asp Leu Ile Val Ser Phe
        450                 455                 460

Gly Val Trp Cys Ile His Arg Ile Leu Asp Leu Ser Leu Met Glu Ser
465                 470                 475                 480

Arg Pro Glu Leu Trp Gly Lys Tyr Thr Tyr Val Leu Asn Arg Leu Gln
                485                 490                 495

Gly Ile Ile Asp Ser Ala Phe Ser Lys Pro Arg Thr Pro Met Ser Pro
                500                 505                 510

Cys Phe Cys Leu Gln Ile Ser Ala Val His Gln Leu Lys Ser Ser Pro
            515                 520                 525

Ser Phe Ser Ser Gly Ile Pro Pro Ala Ala Lys Pro Ala Arg Gly Lys
        530                 535                 540

Cys Thr Thr Ala Val Thr Leu Leu Asp Ile Ile Lys Asp Val Glu Ile
545                 550                 555                 560

Ala Ile Ser Cys Arg Lys Gly Arg Thr Gly Thr Ala Ala Gly Asp Val
                565                 570                 575

Ala Phe Pro Lys Gly Lys Glu Asn Leu Ala Ser Val Leu Lys Arg Tyr
                580                 585                 590

Lys Arg Arg Leu Thr Asn Lys Thr Ala Gly Ala His Glu Gly Pro Gly
            595                 600                 605
```

Ser Arg Val Gln Thr Ser Ala Pro Tyr Gly Ser
        610                 615                 620

<210> SEQ ID NO 13
<211> LENGTH: 1294
<212> TYPE: PRT
<213> ORGANISM: Arabidopsis thaliana
<220> FEATURE:
<223> OTHER INFORMATION: thale cress ecotype Columbia ETHYLENE
      INSENSITIVE 2 (EIN2), transporter, CYTOKININ RESISTANT 1 (CKR1),
      ENHANCED RESPONSE TO ABA3 (ERA3), F12E4.10, ORE2,
      ORE3, ORESARA 2, ORESARA 3, PIR2, locus AT5G03280

<400> SEQUENCE: 13

Met Glu Ala Glu Ile Val Asn Val Arg Pro Gln Leu Gly Phe Ile Gln
 1               5                  10                  15

Arg Met Val Pro Ala Leu Leu Pro Val Leu Leu Val Ser Val Gly Tyr
            20                  25                  30

Ile Asp Pro Gly Lys Trp Val Ala Asn Ile Glu Gly Gly Ala Arg Phe
        35                  40                  45

Gly Tyr Asp Leu Val Ala Ile Thr Leu Leu Phe Asn Phe Ala Ala Ile
    50                  55                  60

Leu Cys Gln Tyr Val Ala Ala Arg Ile Ser Val Val Thr Gly Lys His
65                  70                  75                  80

Leu Ala Gln Ile Cys Asn Glu Glu Tyr Asp Lys Trp Thr Cys Met Phe
                85                  90                  95

Leu Gly Ile Gln Ala Glu Phe Ser Ala Ile Leu Leu Asp Leu Thr Met
            100                 105                 110

Val Val Gly Val Ala His Ala Leu Asn Leu Leu Phe Gly Val Glu Leu
        115                 120                 125

Ser Thr Gly Val Phe Leu Ala Ala Met Asp Ala Phe Leu Phe Pro Val
    130                 135                 140

Phe Ala Ser Phe Leu Glu Asn Gly Met Ala Asn Thr Val Ser Ile Tyr
145                 150                 155                 160

Ser Ala Gly Leu Val Leu Leu Tyr Val Ser Gly Val Leu Leu Ser
                165                 170                 175

Gln Ser Glu Ile Pro Leu Ser Met Asn Gly Val Leu Thr Arg Leu Asn
            180                 185                 190

Gly Glu Ser Ala Phe Ala Leu Met Gly Leu Leu Gly Ala Ser Ile Val
        195                 200                 205

Pro His Asn Phe Tyr Ile His Ser Tyr Phe Ala Gly Glu Ser Thr Ser
    210                 215                 220

Ser Ser Asp Val Asp Lys Ser Ser Leu Cys Gln Asp His Leu Phe Ala
225                 230                 235                 240

Ile Phe Gly Val Phe Ser Gly Leu Ser Leu Val Asn Tyr Val Leu Met
                245                 250                 255

Asn Ala Ala Ala Asn Val Phe His Ser Thr Gly Leu Val Val Leu Thr
            260                 265                 270

Phe His Asp Ala Leu Ser Leu Met Glu Gln Val Phe Met Ser Pro Leu
        275                 280                 285

Ile Pro Val Val Phe Leu Met Leu Leu Phe Ser Ser Gln Ile Thr
    290                 295                 300

Ala Leu Ala Trp Ala Phe Gly Gly Glu Val Val Leu His Asp Phe Leu
305                 310                 315                 320

Lys Ile Glu Ile Pro Ala Trp Leu His Arg Ala Thr Ile Arg Ile Leu
                325                 330                 335

Ala Val Ala Pro Ala Leu Tyr Cys Val Trp Thr Ser Gly Ala Asp Gly
                340                 345                 350

Ile Tyr Gln Leu Leu Ile Phe Thr Gln Val Leu Val Ala Met Met Leu
            355                 360                 365

Pro Cys Ser Val Ile Pro Leu Phe Arg Ile Ala Ser Ser Arg Gln Ile
        370                 375                 380

Met Gly Val His Lys Ile Pro Gln Val Gly Glu Phe Leu Ala Leu Thr
385                 390                 395                 400

Thr Phe Leu Gly Phe Leu Gly Leu Asn Val Phe Val Val Glu Met
                405                 410                 415

Val Phe Gly Ser Ser Asp Trp Ala Gly Gly Leu Arg Trp Asn Thr Val
                420                 425                 430

Met Gly Thr Ser Ile Gln Tyr Thr Thr Leu Leu Val Ser Ser Cys Ala
            435                 440                 445

Ser Leu Cys Leu Ile Leu Trp Leu Ala Ala Thr Pro Leu Lys Ser Ala
        450                 455                 460

Ser Asn Arg Ala Glu Ala Gln Ile Trp Asn Met Asp Ala Gln Asn Ala
465                 470                 475                 480

Leu Ser Tyr Pro Ser Val Gln Glu Glu Ile Glu Arg Thr Glu Thr
                485                 490                 495

Arg Arg Asn Glu Asp Glu Ser Ile Val Arg Leu Glu Ser Arg Val Lys
                500                 505                 510

Asp Gln Leu Asp Thr Thr Ser Val Thr Ser Ser Val Tyr Asp Leu Pro
            515                 520                 525

Glu Asn Ile Leu Met Thr Asp Gln Glu Ile Arg Ser Ser Pro Pro Glu
        530                 535                 540

Glu Arg Glu Leu Asp Val Lys Tyr Ser Thr Ser Gln Val Ser Ser Leu
545                 550                 555                 560

Lys Glu Asp Ser Asp Val Lys Glu Gln Ser Val Leu Gln Ser Thr Val
                565                 570                 575

Val Asn Glu Val Ser Asp Lys Asp Leu Ile Val Glu Thr Lys Met Ala
            580                 585                 590

Lys Ile Glu Pro Met Ser Pro Val Lys Ile Val Ser Met Glu Asn
        595                 600                 605

Asn Ser Lys Phe Ile Glu Lys Asp Val Glu Gly Val Ser Trp Glu Thr
610                 615                 620

Glu Glu Ala Thr Lys Ala Ala Pro Thr Ser Asn Phe Thr Val Gly Ser
625                 630                 635                 640

Asp Gly Pro Pro Ser Phe Arg Ser Leu Ser Gly Glu Gly Gly Ser Gly
                645                 650                 655

Thr Gly Ser Leu Ser Arg Leu Gln Gly Leu Gly Arg Ala Ala Arg Arg
            660                 665                 670

His Leu Ser Ala Ile Leu Asp Glu Phe Trp Gly His Leu Tyr Asp Phe
        675                 680                 685

His Gly Gln Leu Val Ala Glu Ala Arg Ala Lys Lys Leu Asp Gln Leu
            690                 695                 700

Phe Gly Thr Asp Gln Lys Ser Ala Ser Ser Met Lys Ala Asp Ser Phe
705                 710                 715                 720

Gly Lys Asp Ile Ser Ser Gly Tyr Cys Met Ser Pro Thr Ala Lys Gly
                725                 730                 735

Met Asp Ser Gln Met Thr Ser Ser Leu Tyr Asp Ser Leu Lys Gln Gln
            740                 745                 750

Arg Thr Pro Gly Ser Ile Asp Ser Leu Tyr Gly Leu Gln Arg Gly Ser

```
                755             760             765
Ser Pro Ser Pro Leu Val Asn Arg Met Gln Met Leu Gly Ala Tyr Gly
770             775             780

Asn Thr Thr Asn Asn Asn Ala Tyr Glu Leu Ser Glu Arg Arg Tyr
785             790             795             800

Ser Ser Leu Arg Ala Pro Ser Ser Ser Glu Gly Trp Glu His Gln Gln
            805             810             815

Pro Ala Thr Val His Gly Tyr Gln Met Lys Ser Tyr Val Asp Asn Leu
            820             825             830

Ala Lys Glu Arg Leu Glu Ala Leu Gln Ser Arg Gly Glu Ile Pro Thr
            835             840             845

Ser Arg Ser Met Ala Leu Gly Thr Leu Ser Tyr Thr Gln Gln Leu Ala
850             855             860

Leu Ala Leu Lys Gln Lys Ser Gln Asn Gly Leu Thr Pro Gly Pro Ala
865             870             875             880

Pro Gly Phe Glu Asn Phe Ala Gly Ser Arg Ser Ile Ser Arg Gln Ser
            885             890             895

Glu Arg Ser Tyr Tyr Gly Val Pro Ser Ser Gly Asn Thr Asp Thr Val
            900             905             910

Gly Ala Ala Val Ala Asn Glu Lys Lys Tyr Ser Ser Met Pro Asp Ile
            915             920             925

Ser Gly Leu Ser Met Ser Ala Arg Asn Met His Leu Pro Asn Asn Lys
930             935             940

Ser Gly Tyr Trp Asp Pro Ser Gly Gly Gly Tyr Gly Ala Ser
945             950             955             960

Tyr Gly Arg Leu Ser Asn Glu Ser Ser Leu Tyr Ser Asn Leu Gly Ser
            965             970             975

Arg Val Gly Val Pro Ser Thr Tyr Asp Asp Ile Ser Gln Ser Arg Gly
            980             985             990

Gly Tyr Arg Asp Ala Tyr Ser Leu Pro Gln Ser Ala Thr Thr Gly Thr
            995             1000            1005

Gly Ser Leu Trp Ser Arg Gln Pro Phe Glu Gln Phe Gly Val Ala Glu
1010            1015            1020

Arg Asn Gly Ala Val Gly Glu Glu Leu Arg Asn Arg Ser Asn Pro Ile
1025            1030            1035            1040

Asn Ile Asp Asn Asn Ala Ser Ser Asn Val Asp Ala Glu Ala Lys Leu
            1045            1050            1055

Leu Gln Ser Phe Arg His Cys Ile Leu Lys Leu Ile Lys Leu Glu Gly
            1060            1065            1070

Ser Glu Trp Leu Phe Gly Gln Ser Asp Gly Val Asp Glu Glu Leu Ile
            1075            1080            1085

Asp Arg Val Ala Ala Arg Glu Lys Phe Ile Tyr Glu Ala Glu Ala Arg
            1090            1095            1100

Glu Ile Asn Gln Val Gly His Met Gly Glu Pro Leu Ile Ser Ser Val
1105            1110            1115            1120

Pro Asn Cys Gly Asp Gly Cys Val Trp Arg Ala Asp Leu Ile Val Ser
            1125            1130            1135

Phe Gly Val Trp Cys Ile His Arg Val Leu Asp Leu Ser Leu Met Glu
            1140            1145            1150

Ser Arg Pro Glu Leu Trp Gly Lys Tyr Thr Tyr Val Leu Asn Arg Leu
            1155            1160            1165

Gln Gly Val Ile Asp Pro Ala Phe Ser Lys Leu Arg Thr Pro Met Thr
            1170            1175            1180
```

-continued

```
Pro Cys Phe Cys Leu Gln Ile Pro Ala Ser His Gln Arg Ala Ser Pro
1185                1190                1195                1200

Thr Ser Ala Asn Gly Met Leu Pro Pro Ala Ala Lys Pro Ala Lys Gly
            1205                1210                1215

Lys Cys Thr Thr Ala Val Thr Leu Leu Asp Leu Ile Lys Asp Val Glu
        1220                1225                1230

Met Ala Ile Ser Cys Arg Lys Gly Arg Thr Gly Thr Ala Ala Gly Asp
    1235                1240                1245

Val Ala Phe Pro Lys Gly Lys Glu Asn Leu Ala Ser Val Leu Lys Arg
1250                1255                1260

Tyr Lys Arg Arg Leu Ser Asn Lys Pro Val Gly Met Asn Gln Asp Gly
1265                1270                1275                1280

Pro Gly Ser Arg Lys Asn Val Thr Ala Tyr Gly Ser Leu Gly
            1285                1290

<210> SEQ ID NO 14
<211> LENGTH: 1281
<212> TYPE: PRT
<213> ORGANISM: Oryza sativa
<220> FEATURE:
<223> OTHER INFORMATION: rice Japonica Group cultivar Nipponbare
      hypothetical protein Os07g0155600 (EIN2)

<400> SEQUENCE: 14

Met Asp Gly Gln Gln Leu Arg Ser Ser Glu Ser Pro Ala Ser Gly Gly
1               5                   10                  15

Gly Gly Val Thr Gly Gly Gly Ala Pro His Leu Phe His Ala Leu Gly
            20                  25                  30

Pro Ala Leu Leu Ile Ser Ile Gly Tyr Ile Asp Leu Gly Lys Trp Val
        35                  40                  45

Ala Ala Val Glu Ala Gly Ser Arg Phe Gly Leu Asp Leu Val Leu Leu
    50                  55                  60

Ala Leu Leu Phe Asn Phe Met Ala Ile Leu Cys Gln Tyr Leu Ala Ala
65                  70                  75                  80

Cys Ile Gly Thr Val Thr Gly Arg Ser Leu Ala Glu Ile Cys His Gln
                85                  90                  95

Glu Tyr Ser Arg Pro Thr Cys Ile Phe Leu Gly Val Gln Ala Gly Leu
            100                 105                 110

Ser Leu Leu Thr Ser Glu Leu Thr Met Ile Phe Gly Ile Ala Leu Gly
        115                 120                 125

Phe Asn Leu Leu Phe Glu Tyr Asp Asp Leu Ile Thr Gly Ile Cys Phe
    130                 135                 140

Ala Thr Val Val Pro Asn Leu Leu Pro Tyr Ala Ile Ser His Leu Gly
145                 150                 155                 160

Lys Lys Met Val Gly Thr Leu Asn Ala Cys Ile Ala Gly Phe Ala Leu
                165                 170                 175

Leu Cys Tyr Val Leu Gly Leu Leu Val Ser Gln Pro Gln Ile Pro Leu
            180                 185                 190

Thr Thr Asn Val Ile Phe Pro Lys Leu Ser Gly Glu Ser Ala Tyr Ser
        195                 200                 205

Leu Met Ala Leu Leu Gly Ala Asn Val Met Ala His Asn Phe Tyr Ile
    210                 215                 220

His Ser Ser Val Val Gln Gly Gln Lys Arg Ser Ala Phe Ala Val Gly
225                 230                 235                 240

Ala Leu Phe His Asp His Leu Phe Ser Val Leu Phe Ile Phe Thr Gly
```

```
                    245                 250                 255
Ile Phe Leu Val Asn His Val Leu Met Asn Ser Ala Ala Asp Ser
                260                 265                 270

Thr Asn Thr Leu Leu Leu Thr Phe Gln Asp Val Val Glu Leu Met Asn
                275                 280                 285

Gln Ile Phe Val Asn Pro Met Ala Pro Thr Ile Phe Leu Val Val Leu
    290                 295                 300

Leu Phe Ser Ser His Ile Ile Ser Leu Thr Ser Ala Ile Gly Ser Gln
305                 310                 315                 320

Val Ile Ser Gln His Leu Phe Gly Ile Asn Leu Pro Leu Ser Gly His
                325                 330                 335

His Leu Ile Leu Lys Ala Phe Ala Ile Val Pro Ala Leu Tyr Cys Ala
                340                 345                 350

Lys Val Ala Gly Ala Glu Gly Ile Tyr Gln Leu Leu Ile Ile Cys Gln
                355                 360                 365

Ile Ile Gln Ala Met Leu Leu Pro Ser Ser Val Val Pro Leu Phe Arg
    370                 375                 380

Val Ala Ser Ser Arg Leu Ile Met Gly Ala His Arg Val Ser Leu His
385                 390                 395                 400

Leu Glu Ile Leu Thr Phe Leu Ala Phe Leu Leu Met Leu Phe Ser Asn
                405                 410                 415

Ile Ile Phe Met Ala Glu Met Leu Phe Gly Asp Ser Gly Trp Leu Asn
                420                 425                 430

Thr Leu Lys Gly Asn Thr Gly Ser Pro Val Val Phe Pro Ser Thr Val
                435                 440                 445

Leu Ile Thr Val Ala Cys Val Ser Val Ala Phe Ser Leu Tyr Met Ala
    450                 455                 460

Val Thr Pro Leu Lys Ser Gly Ser His Glu Ala Glu Leu Gln Gln Glu
465                 470                 475                 480

Trp Ser Val Pro Ser Gln Lys Glu Leu Leu Asn Thr Thr Gln Asp Arg
                485                 490                 495

Glu Glu Thr Cys Ala Gly Asn Val Thr Tyr Glu Glu Asp Gln Arg Ser
                500                 505                 510

Asp Val Val Pro Ser Pro Arg Ile Gln Pro Val Asp Cys Leu Lys Ser
    515                 520                 525

Ala Leu Asp Tyr Ile Asp Ser Ser Asp Thr Ala Ile Glu Ser Asp His
                530                 535                 540

Asp Ser Gln His Ser Thr Ala His Thr Ser Thr Ala Pro Glu Ser Cys
545                 550                 555                 560

His Ser Pro Ser Phe Ile Pro Glu Gly Ser Lys Ser Val Val Ala Val
                565                 570                 575

Asp Trp Pro Glu Pro Leu Glu Pro Ile Ser Asn Ala Ile Val Ala Glu
                580                 585                 590

Glu Ser Thr Val Glu Ser Val Asp Ser Lys Ser Thr Gly Glu Arg Asp
                595                 600                 605

Ile Glu Val Glu Pro Ala Leu Leu Met Asp Asn Asp Lys Glu Ala Pro
    610                 615                 620

Asn Ile Leu Glu Ser Asp Asn Lys Pro Leu Gly Gly Asn Asn Pro Ser
625                 630                 635                 640

Cys Ala Ser Asp Asp Gly Pro Pro Ser Leu Thr Phe Ser Arg Gly Lys
                645                 650                 655

Gly Ser Asp Ala Gly Asn Gly Ser Gly Ser Leu Ser Arg Leu Ser Gly
                660                 665                 670
```

-continued

Leu Gly Arg Ala Ala Arg Gln Leu Ala Ala Ile Leu Asp Glu Phe
        675                 680                 685

Trp Gly His Leu Phe Asp Tyr His Gly Lys Leu Thr Gln Glu Ala Ser
690                 695                 700

Ser Lys Arg Phe Asp Ile Leu Leu Gly Leu Asp Val Arg Thr Pro Ser
705                 710                 715                 720

Ser Thr Val Arg Ala Asp Ser Gln Ala Asn Glu Ile Pro Lys Ser Pro
                725                 730                 735

Met Val Arg Asp Asn Leu Gln Gly Ser Ala Phe Leu Gly Ser Ser Arg
                740                 745                 750

Asp Leu Met Ser Thr Lys Asn Glu Met Ser Asn Leu Asp Leu Thr Tyr
                755                 760                 765

Gly Leu Gln Met Gly Asn Asn Ile Gly Ser Ser Ala Trp Ser Gln Gly
            770                 775                 780

Met Gln Leu Pro Ser Thr Gln Leu Gln Ser Ser Asn Ser Leu Leu
785                 790                 795                 800

Asp Gln Gly Ala Arg Leu Asn Ser Asn Phe Ser Thr Pro Ser Tyr Ala
                805                 810                 815

Asp Asn Asn Gln Phe Tyr Gln Pro Ala Thr Ile His Gly Tyr Gln Leu
                820                 825                 830

Ala Ser Tyr Leu Lys Gln Met Asn Ala Asn Arg Asn Pro Tyr Ser Ser
            835                 840                 845

Met Pro Leu Asp Pro Gln Arg Leu Pro Lys Ser Ser Ala Ser Ala Val
850                 855                 860

Pro Thr Tyr Val Asp Ser Val Met His Ala Arg Asn Gln Asn Leu Leu
865                 870                 875                 880

Ala Ser Leu Gly Ala Thr Pro Ser Gln Ile Ala Ala Thr Ser Arg Ile
                885                 890                 895

Gly Thr Met Met Ala Glu Arg Ser Tyr Tyr Val Pro Ser Thr Leu Asp
            900                 905                 910

Gly Asn Glu Asn Ala Gly Ser Ser Ala Tyr Ser Lys Lys Tyr His Ser
            915                 920                 925

Ser Pro Asp Ile Ser Ala Leu Ile Ala Ala Ser Arg Ser Ala Leu Leu
        930                 935                 940

Asn Glu Ser Lys Leu Gly Gly Gly Thr Ile Gly Ser Gln Ser Tyr Leu
945                 950                 955                 960

Ser Arg Leu Ala Ser Glu Arg Ser Gln Tyr Thr Asn Ser Val Ala Arg
                965                 970                 975

Pro Ala Ala Pro Leu Ala Phe Asp Glu Leu Ser Pro Lys Leu Pro
                980                 985                 990

Gly Asp Ile Phe Ser Met Gln Gln Ser Pro Asn Pro Ser Ala Arg Ser
            995                 1000                1005

Leu Trp Ala Lys Gln Pro Phe Glu Gln Leu Phe Gly Val Ser Ser Ala
    1010                1015                1020

Glu Leu Thr Lys Ser Glu Phe Asn Pro Ala Gly Arg Ser Gly Gly Met
1025                1030                1035                1040

Thr Lys Asp Asp Phe Ser Tyr Lys Glu Ser Glu Ala Lys Leu Leu Gln
                1045                1050                1055

Ser Leu Arg Phe Cys Ile Ser Lys Leu Leu Lys Leu Glu Gly Ser Gly
                1060                1065                1070

Trp Leu Phe Lys Gln Asn Gly Gly Ser Asp Glu Asp Leu Ile Asp Gln
    1075                1080                1085

```
Val Ala Val Glu Lys Leu Leu Gln Gln Gly Thr Ser Asp Asn Gln
    1090            1095                1100

Leu Leu Leu Gly Asp Thr Gln Gln Pro Pro Cys Asp Lys Ala Asp Ile
1105                1110                1115                1120

Gln Tyr Met Arg Val Leu Pro Asn Cys Gly Asp Cys Ile Trp Arg
            1125                1130                1135

Ala Ser Leu Val Val Ser Phe Gly Val Trp Cys Ile Arg Arg Val Leu
                1140                1145                1150

Asp Leu Ser Leu Val Glu Ser Arg Pro Glu Leu Trp Gly Lys Tyr Thr
            1155                1160                1165

Tyr Val Leu Asn Arg Leu Gln Gly Ile Leu Asp Pro Ala Phe Ser Lys
    1170                1175                1180

Pro Arg Ser Ala Leu Ser Ala Cys Ala Cys Leu His Arg Asp Ile Arg
1185                1190                1195                1200

Val Leu Asn Ser Leu Arg His Ser Ser Leu Val Ala Thr Asn Ser Ile
                1205                1210                1215

Pro Arg Gln Ile Arg Gly Ser Phe Thr Thr Ala Ser Val Val Leu Glu
            1220                1225                1230

Met Ile Lys Asp Val Glu Thr Ala Val Ser Gly Arg Lys Gly Arg Ser
            1235                1240                1245

Gly Thr Ala Ala Gly Asp Val Ala Phe Pro Lys Gly Lys Glu Asn Leu
1250                1255                1260

Ala Ser Val Leu Lys Arg Tyr Lys Arg Arg Leu Ser Ser Lys Gly Gln
1265                1270                1275                1280

Gln

<210> SEQ ID NO 15
<211> LENGTH: 1258
<212> TYPE: PRT
<213> ORGANISM: Zea mays
<220> FEATURE:
<223> OTHER INFORMATION: maize cultivar B73 ethylene insensitive 2
      (Ein2-25, ZmEin2-25)

<400> SEQUENCE: 15

Met Asp Ala Pro Asp Val Gln Gln Ser Met Gly Tyr Lys Glu Ser Arg
  1               5                  10                  15

Gly Gly Met Pro Lys Phe Phe His Ala Leu Gly Pro Ala Leu Leu Ile
                20                  25                  30

Ser Met Gly Tyr Ile Asp Leu Gly Lys Trp Val Ala Ala Val Glu Ala
            35                  40                  45

Gly Ser Cys Phe Gly Phe Asp Leu Val Leu Leu Ala Leu Leu Phe Asn
        50                  55                  60

Phe Thr Ala Ile Val Cys Gln Tyr Leu Ala Ala Cys Ile Gly Thr Val
 65                  70                  75                  80

Thr Gly Lys Asn Leu Ala Glu Ile Cys His Gln Glu Tyr Asn Gln Pro
                85                  90                  95

Thr Cys Ile Phe Leu Gly Val Gln Ala Gly Leu Ser Leu Leu Thr Ser
            100                 105                 110

Glu Leu Ser Met Ile Phe Gly Ile Ala Leu Gly Phe Asn Leu Leu Phe
        115                 120                 125

Glu Tyr Asp Asp Leu Ile Thr Gly Ile Cys Phe Ala Thr Val Met Glu
    130                 135                 140

Gly Thr Ile Asn Ala Cys Ile Ala Gly Phe Ala Leu Leu Ser Tyr Val
145                 150                 155                 160
```

-continued

```
Leu Gly Leu Leu Val Ser Gln Pro Gln Ile Pro Leu Thr Met Asn Val
                165                 170                 175
Ile Phe Pro Lys Ile Ser Gly Glu Ser Ala Tyr Ser Leu Met Ala Leu
            180                 185                 190
Leu Gly Ala Asn Ile Met Ala His Asn Phe Tyr Ile His Ser Ser Tyr
        195                 200                 205
Leu Gln Gly Gln Lys Lys Ser Ser Ala Val Gly Leu Gly Ala Leu Phe
    210                 215                 220
His Asp His Leu Phe Ser Ile Leu Phe Ile Phe Thr Gly Ile Phe Met
225                 230                 235                 240
Val Asn Tyr Val Leu Met Asn Ser Ala Ala Glu Ser Thr Asn Thr
                245                 250                 255
Leu Leu Ile Thr Phe Gln Asp Val Val Glu Leu Met Asn Gln Ile Phe
            260                 265                 270
Val Asn Pro Leu Ala Pro Thr Ile Phe Leu Val Val Leu Leu Phe Ser
        275                 280                 285
Ser His Ile Ile Ser Leu Thr Ser Ala Ile Gly Ser Gln Val Ile Ser
    290                 295                 300
His His Leu Phe Gly Ile Asn Leu Pro Leu Ser Gly His Arg Leu Leu
305                 310                 315                 320
Leu Lys Val Phe Ala Ile Val Pro Thr Leu Tyr Trp Ala Lys Val Ala
                325                 330                 335
Gly Ala Glu Gly Ile Tyr Gln Leu Leu Ile Ile Cys Gln Ile Ile Gln
            340                 345                 350
Ala Met Leu Leu Pro Ser Ser Val Val Pro Leu Phe Arg Val Ala Ser
        355                 360                 365
Ser Arg Ser Ile Met Gly Ala His Arg Val Ser Leu His Leu Glu Ile
    370                 375                 380
Leu Val Phe Leu Ala Phe Leu Leu Met Leu Phe Ser Asn Ile Ile Phe
385                 390                 395                 400
Val Ala Glu Met Leu Phe Gly Asp Ser Gly Trp Met Asn Asn Leu Lys
                405                 410                 415
Gly Tyr Thr Gly Ser Pro Val Val Leu Pro Tyr Thr Val Leu Val Leu
            420                 425                 430
Val Ala Leu Ile Ser Val Ala Phe Ser Leu Tyr Leu Ala Val Thr Pro
        435                 440                 445
Leu Arg Ser Gly Ser His Glu Ala Glu Ser His Glu Trp Ser Val His
    450                 455                 460
Ser Gln Arg Glu Leu Leu Asn Thr Ser Gln Glu Arg Glu Asp Val Lys
465                 470                 475                 480
Val Asp Asn Val Thr Tyr Glu Glu Asp Gln Arg Ser Asp Val Val Pro
                485                 490                 495
Ser Pro Arg Asp Val Pro Asp Ser His Pro Glu Leu Ala Leu Asp Tyr
            500                 505                 510
Ile Asp Thr Ser Asp Thr Ala Val Glu Ser Asp His Ser Gln Gln
        515                 520                 525
Ser Thr Ala Tyr Ala Ser Thr Ala Pro Glu Thr Cys Ser Ser Pro Ser
    530                 535                 540
Phe Thr Arg Glu Glu Ser Lys Ser Val Val Ala Val Asn Trp Pro Glu
545                 550                 555                 560
Pro Leu Glu Lys Val Pro Thr Ser Thr Val Met Glu Glu Ser Thr Val
                565                 570                 575
Glu Asn Val Val Ser Arg Ile Thr Thr Glu Arg Asp Val Leu Val Glu
```

-continued

```
                580                 585                 590
Thr Asp Val Ser Gly Lys Asp Lys Glu Asp Ile Arg Thr Leu Glu
            595                 600                 605
Ser Glu Lys Ser Ile Val Asp Ser Thr Pro Tyr Val Ser Asp Gly
            610                 615                 620
Pro Pro Ser Leu Thr Phe Ser Arg Gly Lys Gly Ser Asp Ala Gly Asn
625                 630                 635                 640
Gly Ser Gly Ser Leu Ser Arg Leu Ser Gly Leu Gly Arg Ala Ala Arg
                645                 650                 655
Arg Gln Leu Ala Ala Thr Leu Asp Glu Phe Trp Gly His Leu Phe Asp
                660                 665                 670
Tyr His Gly Lys Leu Thr Gln Glu Ala Ser Thr Lys Lys Phe Gly Ile
                675                 680                 685
Leu Leu Gly Ile Asp Leu Arg Thr Pro Ser Thr Val Arg Thr Asp
                690                 695                 700
Lys Gln Ala Ala Glu Ile Leu Lys Ser Pro Leu Val Arg Asp Ser Met
705                 710                 715                 720
Arg Gly Ala Ala Phe Leu Ser Ser Val Asp Met Met Ser Pro Lys
                725                 730                 735
Asn Glu Thr Ser Asn Leu Glu Leu Ala Tyr Gly Leu Gln Arg Gly Pro
                740                 745                 750
Gly Met Gly Leu Ser Ser Trp Ser Gln Gly Met Gln Leu Pro Asn Thr
                755                 760                 765
Gln Leu Gln Ser Ser Ser Asn Ser Leu Leu Glu Gln Ser Ala Arg Leu
                770                 775                 780
Asn Ser Asn Phe Ser Ser Ser Tyr Ser Asp Asn Asn Gln Phe Tyr Gln
785                 790                 795                 800
Pro Ala Thr Ile His Gly Tyr Gln Leu Thr Ser Tyr Leu Lys Gln Met
                805                 810                 815
Asn Ala Ser Pro Ser Leu Tyr Ser Ser Met Pro Leu Asp Pro Gln Arg
                820                 825                 830
Leu Pro Lys Ser Ser Val Ser Ala Val Pro Asn Tyr Ala Asp Ser Met
                835                 840                 845
Met His Ala Arg Asn His Asn Leu Leu Ala Ser Leu Gly Gly Thr Thr
                850                 855                 860
Thr Gln Leu Pro Ala Thr Ser Arg Val Gly Ser Met Met Pro Glu Arg
865                 870                 875                 880
Ser Tyr Tyr Asp Pro Ser Ser Val Asp Gly Asn Glu Asn Ala Gly Ser
                885                 890                 895
Pro Ala Tyr Ser Lys Lys Tyr His Ser Ser Pro Asp Met Ser Gly Ile
                900                 905                 910
Ile Ala Ala Ser Arg Ala Ala Leu Asn Glu Ala Lys Leu Gly Ala
                915                 920                 925
Ala Ile Gly Pro Gln Ser Tyr Leu Ser Arg Leu Ala Ala Glu Arg Ser
                930                 935                 940
Gln Tyr Ala Ser Ser Thr Ala Arg Pro Ala Ala Pro Leu Ala Phe Asp
945                 950                 955                 960
Glu Leu Ser Pro Pro Lys Leu Gln Ser Asp Ile Phe Ser Ala Gln Ser
                965                 970                 975
Ser Met Arg Pro Ser Ala Arg Ser Leu Trp Ala Lys Gln Pro Phe Glu
                980                 985                 990
Gln Leu Phe Gly Met Ser Ser Ala Glu Leu Ser Lys Gly Asp Phe Asn
                995                 1000                1005
```

-continued

Leu Pro Gly Arg Ser Gly Gly Val Ala Lys Asp Asp Phe Ser Tyr Lys
        1010                1015                1020

Glu Ser Glu Thr Lys Leu Leu Gln Ser Leu Arg Leu Cys Ile Met Lys
1025                1030                1035                1040

Leu Leu Lys Leu Glu Gly Ser Gly Trp Leu Phe Lys Gln Asn Gly Gly
                1045                1050                1055

Cys Asp Glu Asp Leu Ile Asp Arg Val Ala Ala Ala Glu Lys Leu Leu
            1060                1065                1070

Met Gln Gly Thr Ala Glu Asn Gln Leu Leu Leu His Gly Gly Asp Leu
        1075                1080                1085

Gln Gln His Ser Ser Asp Gln Ala Gly Ile Gln Tyr Met Arg Thr Leu
    1090                1095                1100

Pro Asn Cys Gly Glu Asp Cys Val Trp Arg Ala Ser Leu Val Val Ser
1105                1110                1115                1120

Phe Gly Val Trp Cys Val Arg Arg Val Leu Asp Met Ser Leu Val Glu
                1125                1130                1135

Ser Arg Pro Glu Leu Trp Gly Lys Tyr Thr Tyr Val Leu Asn Arg Leu
            1140                1145                1150

Gln Gly Ile Leu Asp Pro Ala Phe Ser Lys Pro Arg Gly Ala Leu Thr
        1155                1160                1165

Ile Cys Thr Cys Leu Gln Lys Asp Thr Arg Val Arg Asn Ser Pro Pro
    1170                1175                1180

His Ser Gly Leu Thr Ala Met Gly Pro Val Pro Thr Pro Ile Arg Gly
1185                1190                1195                1200

Ala Phe Thr Thr Ala Gly Val Val Leu Glu Met Ile Lys Asp Val Glu
                1205                1210                1215

Ala Ala Val Ser Gly Arg Lys Gly Arg Ser Gly Thr Ala Ala Gly Asp
            1220                1225                1230

Val Ala Phe Pro Lys Gly Lys Glu Asn Leu Ala Ser Val Leu Lys Arg
        1235                1240                1245

Tyr Lys Arg Arg Leu Ala Ser Lys Gly Gln
    1250                1255

<210> SEQ ID NO 16
<211> LENGTH: 21
<212> TYPE: DNA
<213> ORGANISM: Artificial Sequence
<220> FEATURE:
<223> OTHER INFORMATION: synthetic oligonucleotide for artificial
      microRNA (amiRNA) construction

<400> SEQUENCE: 16
tctttgaata aacggtccca t                                           21

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide for artificial
      microRNA (amiRNA) construction

<400> SEQUENCE: 17
tctttgaata aacggtgcca t                                           21

<210> SEQ ID NO 18
<211> LENGTH: 408
<212> TYPE: PRT

```
<213> ORGANISM: Zea mays
<220> FEATURE:
<223> OTHER INFORMATION: maize strain B73, clone ZM_BFc0026B02
      GRMZM2G156490 unkown protein

<400> SEQUENCE: 18

Met Ala Ser Ser Phe Lys Pro His Ala Ala Pro Lys Arg Arg Ala Leu
 1               5                  10                  15

Ala Thr Phe Asn Ile Gly Ala Leu Pro Leu Asp Leu Leu Val Tyr Glu
                20                  25                  30

Ile Leu Leu Arg Leu Pro Ala Lys Leu Leu Cys Arg Leu Arg Thr Val
            35                  40                  45

Cys Arg Leu Trp Arg Ser Ile Leu Ser Asp Pro His Phe Ala Ala Ala
        50                  55                  60

His Ala Met Arg His Pro Gly Pro Leu Ile Ile Ala Ala Ile Asp Glu
65                  70                  75                  80

Arg Pro Asp Val His Val Asn Ile Met Asp Leu Ser Gly Gln Ile Leu
                85                  90                  95

Lys Gln Val Arg Gly Val Pro Gly Gln Arg Val Val Ser Thr Ala Leu
            100                 105                 110

Asp Leu Val Phe Val Lys Lys Thr Asp Ser Ser Ser Ser Ser Tyr Arg
        115                 120                 125

Phe Cys Asn Pro Phe Ser Gly Asp Val His Tyr Leu Pro Asp Gln Leu
    130                 135                 140

Leu Asn Pro Ala Thr Gly Ala Val Tyr Gln Ile Pro Asn Ser Phe Ala
145                 150                 155                 160

Glu Glu His Ile Asp Phe Thr Ser Ser Phe Ile Ser Gln Ser Arg Tyr
                165                 170                 175

Leu Phe Gly Gln Val Ser Ser Thr Gly Glu Tyr Lys Val Phe Arg Lys
            180                 185                 190

Leu Tyr His Leu Ser Val Gln Phe Gly Gly Arg Gln Leu Leu Glu Ile
        195                 200                 205

Cys Thr Val Asn Gly Ser Asn His Thr Gly Trp Arg Ala Val Thr Pro
    210                 215                 220

Leu Glu Lys Asn Ile Gln Phe Gly Val Phe Thr Ser Val Ile Asn
225                 230                 235                 240

Gly Ile Ile Tyr Ser Gln Cys Phe Asp Pro His His Ser Ile Thr Tyr
                245                 250                 255

Asp Cys Arg Ala Thr Glu Glu Asp Leu Ile Ile Thr Phe Asp Ile Glu
            260                 265                 270

Thr Glu Lys Trp Gly Pro Phe Met Arg Gly Pro Pro Ile Ser Phe Ser
        275                 280                 285

Asp Ala Ala Ala Gln Val Phe Asn Asp Leu Arg Leu Pro Pro Ile Lys
    290                 295                 300

Gln Leu Thr Leu Ala Asn Leu Asn Gly Ser Leu Ala Val Val His Gly
305                 310                 315                 320

Pro Ala Pro Ser Met Asp Ile Trp Ile Leu Met Asp Ser Gly Lys Gly
                325                 330                 335

Leu Trp Val Lys Gln Tyr Ile Ile Gln Phe Lys Glu Tyr Ala Ser Phe
            340                 345                 350

Gln Tyr Val His Pro Leu Val Val Leu Arg Asp Gly Arg Val Val Leu
        355                 360                 365

Tyr Lys Glu Asp Met Gln Leu Leu Gln Ile Tyr Asp Pro Arg Thr Asn
    370                 375                 380
```

```
Thr Leu Thr Asp Ser Val Glu Val Cys His Phe Ser Ala Val Ala Leu
385                 390                 395                 400

Phe Gly Gly Asn Leu Leu Ser Leu
                405
```

<210> SEQ ID NO 19
<211> LENGTH: 396
<212> TYPE: PRT
<213> ORGANISM: Populus trichocarpa
<220> FEATURE:
<223> OTHER INFORMATION: black cottonwood F-box family protein
      POPTR_0006s01360

<400> SEQUENCE: 19

```
Met Ser Gly Leu Pro Leu Glu Met Ile Ala Glu Ile Leu Cys Arg Leu
1               5                   10                  15

Pro Ala Lys Glu Leu Leu Cys Cys Arg Ser Val Ser Lys Pro Trp Cys
                20                  25                  30

Ala Leu Ile Asp Gly Pro Asn Phe Val Lys Leu His Leu Lys His Ser
            35                  40                  45

Met Asp Thr Ser Ser Asn Leu Tyr Ile Ile Leu Arg Thr Thr Ser His
    50                  55                  60

Val His Tyr Met Asp Phe Glu Gln Asn Leu Val Leu Asn Asp Cys Val
65                  70                  75                  80

Thr Leu Lys Glu Leu Asn His Pro Leu Met Cys Tyr Asn His Gly Ile
                85                  90                  95

Lys Val Leu Gly Ser Val Asn Gly Leu Leu Cys Ile Ser Asn Val Val
            100                 105                 110

Asp Asp Ile Ala Val Trp Asn Pro Ser Thr Arg Lys His Arg Val Val
        115                 120                 125

Pro Phe Leu Pro Ile Glu Leu Lys Arg Tyr Phe Gly Thr Lys Ser Cys
    130                 135                 140

Ser Val Tyr Val Phe Gly Phe Gly Tyr Asp Ser Val Arg Asp Asp Tyr
145                 150                 155                 160

Lys Leu Val Arg Ile Ala Gln Phe Gly Gly Gly Lys Arg Ser Phe
                165                 170                 175

Glu Ser Glu Val Lys Val Tyr Ser Leu Arg Lys Gln Ser Trp Arg Arg
                180                 185                 190

Ile Gly Asp Met Pro Tyr Cys Val His Tyr Pro Gly Ala Asn Gly Val
            195                 200                 205

Phe Ala Asn Gly Ala Leu His Trp Val Val Gly Glu Asn Pro Glu Ser
        210                 215                 220

Asn Val Ala Asn Ile Val Val Ala Leu Asp Leu Gly Val Glu Asp Tyr
225                 230                 235                 240

Arg Glu Val Leu Gln Pro Glu Tyr Lys Asp Lys Asn Phe Tyr Ile Asp
                245                 250                 255

Leu Gly Val Leu Arg Gly Cys Leu Cys Phe Leu Ala Asn Phe Leu Gly
            260                 265                 270

Glu Arg Val Asp Val Trp Met Met Lys Glu Tyr Gly Val Lys Glu Ser
        275                 280                 285

Trp Thr Lys Leu Phe Ser Val Ala Gln Tyr Glu Val Ile Gly Phe Leu
    290                 295                 300

Arg Ser Leu Lys Pro Leu Ala Tyr Ser Lys Ser Gly Asp Glu Val Leu
305                 310                 315                 320

Ile Glu His Asp Asn Leu Asp Leu Cys Trp Tyr Asp Leu Lys Arg Lys
                325                 330                 335
```

Gln Val Lys Asn Arg Ile Pro Gly Ile Pro Tyr Ser Phe Glu Ala Asp
              340                 345                 350

Thr Phe Val Glu Ser Leu Ile Ser Val Ser Pro Asn Arg His Leu Asp
              355                 360                 365

Gly Arg Thr Gln Asp Asp Glu Asp Ser Lys Asp Arg Asn Lys Arg
              370                 375                 380

Asp Asp Phe Leu Ser Glu Gly Phe Lys Leu Val Leu
385                 390                 395

<210> SEQ ID NO 20
<211> LENGTH: 414
<212> TYPE: PRT
<213> ORGANISM: Oryza sativa
<220> FEATURE:
<223> OTHER INFORMATION: rice Japonica Group cultivar Nipponbare
      OsFBX440 LOC_Os12g06740, alias 13112.m00693 F-box domain
      containing protein, expressed

<400> SEQUENCE: 20

Met Met Ala Lys Arg Cys Thr Asp Ile Leu Leu Ala Pro Arg Pro Arg
1               5                   10                  15

Lys Thr Lys Arg Ile Asp Ile Asn Ser Cys Arg Ser Arg Phe Leu Leu
              20                  25                  30

Pro Tyr Ile Pro Asp Glu Val Met Phe Asp Val Leu Leu Arg Leu Pro
              35                  40                  45

Ser Lys Ser Leu Met Arg Phe Lys Ser Val Cys Lys Ala Trp His Ala
        50                  55                  60

Met Ile Ser Ser Pro Ile Phe Ile Asn Ala His Leu Glu Trp Ser Lys
65                  70                  75                  80

Leu Lys Pro Ser Ser Leu Leu Met Ala Pro Gly Phe Tyr Gln Lys Gln
                85                  90                  95

Lys Asn Gly Gln Asn Ile Ala Phe Leu Met Gly Leu Tyr Lys Tyr Gln
              100                 105                 110

Gly Gly Asn Asn Asn Val Val His Leu His Asp Phe Pro Arg Asp Phe
        115                 120                 125

Pro Gln Val Leu Asp Thr Trp Thr Arg Pro Val His Cys Asp Gly Leu
      130                 135                 140

Leu Leu Val Ser Asn Met Ser Lys Lys Met Ile Ile Tyr Asn Pro Ser
145                 150                 155                 160

Thr Arg Glu Ile Val Ser Leu Pro Lys Gly Ser Arg Asn Leu His Lys
              165                 170                 175

Gly Thr Gly Ile Gly Phe Gly Phe Asp Pro Arg Ser Ser Lys Tyr Lys
              180                 185                 190

Val Ala Arg Val Phe Tyr Gln Arg Asp Asp Lys Thr Ser Met Leu Val
        195                 200                 205

Cys Lys Phe Glu Val Leu Thr Leu Gly Thr Ile Asn Val Trp Arg Gln
      210                 215                 220

Thr Glu Asp Pro Pro Tyr Pro Ile Gly Lys Ser Thr Pro Val His Val
225                 230                 235                 240

Lys Gly Ala Ile Tyr Trp Met Val Ser Arg Thr Ser Leu Cys Pro Asp
              245                 250                 255

Pro Pro Asn Thr Leu Val Arg Phe Cys Leu Thr Asp Glu Lys Phe Ser
              260                 265                 270

Leu Phe Pro Cys Pro Cys Asn Val Lys Pro Ser Cys Leu Thr Gly Leu
        275                 280                 285

```
Gly Asp Glu Leu Tyr Cys Gly Tyr Phe Phe Ser Gln Pro Leu Gln Leu
    290                 295                 300

Glu Ile Trp Gly Cys Ser Val Val Gly Gln Lys Pro Glu Trp Thr Arg
305                 310                 315                 320

Arg Cys Ala Leu Gln Ile Pro Pro Asp Val Ile Lys Arg Pro Val Ala
                325                 330                 335

Ser Pro Leu Val Val Phe His Gly Lys Met Leu Leu Leu Ala Leu Lys
                340                 345                 350

Lys Val Tyr Lys Tyr Asp Ile Gln Ala Cys Lys Leu Glu Lys Ile Pro
                355                 360                 365

Leu Val Val Glu Asp Phe Met Cys Tyr Asp Arg Glu Asn Asn Met Tyr
370                 375                 380

Gln Thr Tyr Ser Lys Lys Glu Val Leu Thr Ser Trp Lys Thr Tyr Ile
385                 390                 395                 400

Cys His Ala Asn Thr Leu Gly His Val Phe Leu Leu Val Asn
                405                 410

<210> SEQ ID NO 21
<211> LENGTH: 410
<212> TYPE: PRT
<213> ORGANISM: Oryza sativa
<220> FEATURE:
<223> OTHER INFORMATION: rice Japonica Group cultivar Nipponbare
      OsFBX440 LOC_Os12g06740, alias 13112.m00694 F-box domain
      containing protein, expressed

<400> SEQUENCE: 21

Met Met Ala Lys Arg Cys Thr Asp Ile Leu Leu Ala Pro Arg Pro Arg
 1               5                  10                  15

Lys Thr Lys Arg Ile Asp Ile Asn Ser Cys Arg Ser Arg Phe Leu Leu
                20                  25                  30

Pro Tyr Ile Pro Asp Glu Val Met Phe Asp Val Leu Leu Arg Leu Pro
                35                  40                  45

Ser Lys Ser Leu Met Arg Phe Lys Ser Val Cys Lys Ala Trp His Ala
 50                  55                  60

Met Ile Ser Ser Pro Ile Phe Ile Asn Ala His Leu Glu Trp Ser Lys
65                  70                  75                  80

Leu Lys Pro Ser Ser Leu Leu Met Ala Pro Gly Phe Tyr Gln Lys Gln
                85                  90                  95

Lys Asn Gly Gln Asn Ile Ala Phe Leu Met Gly Leu Tyr Lys Tyr Gln
                100                 105                 110

Gly Gly Asn Asn Asn Val Val His Leu His Asp Phe Pro Arg Asp Phe
                115                 120                 125

Pro Gln Val Leu Asp Thr Trp Thr Arg Pro Val His Cys Asp Gly Leu
                130                 135                 140

Leu Leu Val Ser Asn Met Ser Lys Lys Met Ile Ile Tyr Asn Pro Ser
145                 150                 155                 160

Thr Arg Glu Ile Val Ser Leu Pro Lys Gly Ser Arg Asn Leu His Lys
                165                 170                 175

Gly Thr Gly Ile Gly Phe Gly Phe Asp Pro Arg Ser Ser Lys Tyr Lys
                180                 185                 190

Val Ala Arg Val Phe Tyr Gln Arg Asp Asp Lys Thr Ser Met Leu Val
                195                 200                 205

Cys Lys Phe Glu Val Leu Thr Leu Gly Thr Ile Asn Val Trp Arg Gln
210                 215                 220

Thr Glu Asp Pro Pro Tyr Pro Ile Gly Lys Ser Thr Pro Val His Val
```

```
                225                 230                 235                 240
Lys Gly Ala Ile Tyr Trp Met Val Ser Arg Thr Ser Leu Cys Pro Asp
                245                 250                 255

Pro Pro Asn Thr Leu Val Arg Phe Cys Leu Thr Asp Glu Lys Phe Ser
            260                 265                 270

Leu Phe Pro Cys Pro Cys Asn Val Lys Pro Ser Cys Leu Thr Gly Leu
        275                 280                 285

Gly Asp Glu Leu Tyr Cys Gly Tyr Phe Phe Ser Gln Pro Leu Gln Leu
    290                 295                 300

Glu Ile Trp Gly Cys Ser Val Val Gly Gln Lys Pro Glu Trp Thr Arg
305                 310                 315                 320

Arg Cys Ala Leu Gln Ile Pro Pro Asp Val Ile Lys Arg Pro Val Ala
                325                 330                 335

Ser Pro Leu Val Val Phe His Gly Lys Met Leu Leu Leu Ala Leu Lys
            340                 345                 350

Lys Val Tyr Lys Tyr Asp Ile Gln Ala Cys Lys Leu Glu Lys Ile Pro
        355                 360                 365

Leu Val Val Glu Asp Phe Met Cys Tyr Asp Arg Glu Asn Asn Met Tyr
    370                 375                 380

Gln Thr Tyr Ser Lys Lys Glu Val Met Asp Phe His Leu Phe Asn Tyr
385                 390                 395                 400

Val Glu Ser Leu Val Ser Ile Arg Glu Phe
                405                 410

<210> SEQ ID NO 22
<211> LENGTH: 391
<212> TYPE: PRT
<213> ORGANISM: Carica papaya
<220> FEATURE:
<223> OTHER INFORMATION: papaya evm.TU.supercontig_42.22 F-box protein

<400> SEQUENCE: 22

Met Asp His Ile Asp Ile Leu Phe Asp Val Leu Ser Arg Leu Pro Thr
1               5                   10                  15

Lys Asn Leu Thr Arg Leu Lys Arg Val Cys Lys Ala Trp Arg Lys Leu
            20                  25                  30

Ile Ser Asp Pro Ser Phe Ile Lys Val His Ser Gly Lys Lys Glu Pro
        35                  40                  45

Ile Ala Gly Phe Phe Leu Gln Trp Arg Tyr Arg Trp Phe Cys Asn Asp
    50                  55                  60

Val Lys Thr Ile Asn Tyr Ile Pro Val Glu Ala Lys Arg Ser Gln Val
65                  70                  75                  80

Lys Gln Met Ile Phe Asp Phe Leu Pro Gln Asp Val Val Leu Met Ala
                85                  90                  95

Ser Cys Asn Gly Leu Val Cys Cys Arg Ser Cys Tyr Pro Phe Lys Asp
            100                 105                 110

Pro Ala Leu Tyr Val Cys Asn Pro Leu Asn Lys Glu Trp Val Thr Leu
        115                 120                 125

Lys Trp Lys Ser Pro Asn Lys Glu Ala Thr Ile Gly Leu Ala Phe Asp
    130                 135                 140

Pro Cys Arg Asp Leu Thr Asp Ser Ser Thr Lys Phe Ser Leu Val Arg
145                 150                 155                 160

Val Glu Gln Tyr Lys Ala Glu Glu Gly Met Phe Cys Tyr Ser Phe Asp
                165                 170                 175

Ile Tyr Ser Ser Asp Ala Gly Ala Trp Lys Lys Ser Ser Glu Val Cys
```

-continued

```
                180               185               190
Gln Cys Asn Asp Ser Leu Tyr Arg Asn Lys Ser Thr Phe Ile Gly Gly
        195                 200                 205

Ser Leu Tyr Trp Leu Thr Asp Asp Glu Lys Ile Leu Ile Phe Asn Leu
    210                 215                 220

Glu Gln Glu Leu Ser Trp Leu Leu Arg Val Pro Val Pro Thr Thr Glu
225                 230                 235                 240

Phe Met Cys Ile Pro Ala Gly Cys Ile Gly Glu Ser Glu Gly Lys Leu
                245                 250                 255

His Tyr Val Ala Ile Ser Ala Gly Gly Ile His Val Trp Val Leu Glu
                260                 265                 270

Asp Ile Leu Glu Ala Lys Trp Glu Ile Lys Gln Thr Thr Ser Leu Asn
        275                 280                 285

Ser Leu Glu Ala Glu Asn Pro Asn Phe Leu Cys Asp Leu Gly Glu Arg
    290                 295                 300

Ala Ala Leu Arg Gly Asn Ser Gln Met Ser Pro Trp Met Asp Pro Met
305                 310                 315                 320

Ala Phe Lys Asp Gly Trp Leu Leu Met Lys Val Ser Gly Arg Ile Leu
                325                 330                 335

Met Tyr His Val Glu Ser Asn Lys Met Lys Gln Val Phe Thr Val Ala
                340                 345                 350

Glu Leu Glu Ser Ser Ser Leu Phe Ala Ala Met Val Val Pro Tyr Ser
        355                 360                 365

Leu Ser Leu Val Pro Leu Lys Gln Leu Arg Arg His Leu Ser Ser His
    370                 375                 380

Phe Phe Ser Lys Lys Glu Lys
385                 390
```

ETP1 AND ETP2 REGULATE PLANT ETHYLENE RESPONSE

The present patent application claims benefit of priority to U.S. Provisional Patent Application No. 61/162,469, filed Mar. 23, 2009, which is incorporated by reference.

BACKGROUND OF THE INVENTION

In plants, ethylene ($C_2H_4$) is a regulator of various physiological and morphological responses, including inhibition of cell expansion, promotion of leaf and flower senescence, induction of fruit ripening and abscission, resistance to pathogen infection, and adaptation to stress conditions (Bleecker, A. B. and Kende, H., *Annu. Rev. Cell. Dev. Biol.*, 16:1-18 (2000); Guo, H. and Ecker, J. R., *Curr. Opin. Plant. Biol.*, 7:40-49 (2004)). The molecular dissection of ethylene signal transduction began with genetic screens based on the well-documented triple response phenotype of ethylene-treated etiolated *Arabidopsis* seedlings. Through these screens, many ethylene mutants have been obtained, including the ethylene insensitive mutants etr1, ein2, ein3, ein5 (Bleecker, A. B. et al., *Science*, 241:1086-1089 (1988); Guzman, P. and Ecker, J. R., *Plant Cell*, 2:513-523 (1990); Roman, G. et al., *Genetics*, 139:1393-1409 (1995)); the ethylene overproducing mutants eto1, eto2, eto3, and the ethylene constitutive response mutant ctr1 (Guzman, P. and Ecker, J. R., *Plant Cell*, 2:513-523 (1990); Kieber, J. J. et al., *Cell*, 72:427-441 (1993)). Initial studies of these mutants have revealed a mostly linear framework for the ethylene-signaling pathway, leading from ethylene perception at the membrane to transcriptional activation in the nucleus (Stepanova, A. N. and Ecker, J. R., *Curr. Opin. Plant. Biol.*, 3:353-360 (2000); Chen, Y. F. et al., *J. Biol. Chem.*, 277:19861-19866 (2002); Guo, H. and Ecker, J. R., *Curr. Opin. Plant. Biol.*, 7:40-49 (2004)).

Ethylene is perceived by a family of membrane bound, endoplasmic reticulum-located receptors ETHYLENE RESPONSE1 (ETR1), ETHYLENE RESPONSE SENSOR1 (ERS1), ETHYLENE RESPONSE2 (ETR2), ETHYLENE INSENSITIVE4 (EIN4), and ETHYLENE RESPONSE SENSOR2 (ERS2), which are similar in sequence and structure to bacterial two-component histidine kinases (Chang, C. et al., *Science*, 262:539-544 (1993); Hua, J. et al., *Plant Cell*, 10:1321-1332 (1998); Kendrick, M. D. and Chang, C., *Curr. Opin. Plant. Biol.*, 11:479-485 (2008)). Each receptor has an N-terminal membrane-spanning domain that binds ethylene with a copper cofactor provided by the RESPONSIVE TO ANTAGONIST1 (RAN1) copper transporter (Hirayama, T. et al., *Cell*, 97:383-393 (1999)). Briefly, in the absence of ethylene gas, the ethylene receptors repress downstream responses through interaction with CONSTITUTIVE TRIPLE RESPONSE1 (CTR1) (Gao, Z. et al., *J. Biol. Chem.*, 278:34725-34732 (2003)), which is a member of Raf kinase family that also acts as a negative regulator of the downstream ethylene signaling pathway (Kieber, J. J. et al., *Cell*, 72:427-441 (1993)). In the presence of ethylene, the receptors stop repressing ethylene response through inactivation of CTR1. Additionally, EIN2 is de-repressed and positively regulates the levels of ETHYLENE INSENSITIVE3 (EIN3) and ETHYLENE INSENSITIVE3-LIKE1 (EIL1) the key transcription factors of ethylene signaling pathway, which results in the activation of transcription of ethylene responsive genes (Chao, Q. et al., *Cell*, 89:1133-1144 (1997); Solano, R. et al., *Genes & Dev.*, 12:3703-3714 (1998)). Recently, numerous studies have expanded the linear view of ethylene signaling pathway. For instance, a new protein, REVERSION-TO-ETHYLENE SENSITIVITY1 (RTE1), which is co-localized with the ethylene receptor ETR1, was identified as a positive regulator of ETR1 function, but the connection between RTE1 and ETR1 is still under investigation (Resnick, J. S. et al., *Proc. Natl. Acad. Sci. U.S.A.*, 103:7917-7922 (2006); Solano, R. et al., *Genes & Dev.*, 12:3703-3714 (1998); Dong, C. H. et al., *Plant J.*, 53:275-286 (2008)). Additionally, a number of groups found that posttranscriptional regulation of protein levels is a key mechanism of modulating EIN3 activity by ethylene. Specifically, they found that ubiquitin/proteasome-mediated degradation negatively regulates ethylene responses by targeting EIN3 for turnover through two F-box proteins EIN3-BINDING F BOX PROTEIN1 (EBF1) and EIN3-BINDING F BOX PROTEIN2 (EBF2) (Guo, H. and Ecker, J. R., *Cell*, 115:667-677 (2003); Potuschak, T. et al., *Cell*, 115:679-689 (2003); Gagne, J. M. et al., *Proc. Natl. Acad. Sci. U.S.A.*, 101:6803-6808 (2004)). Interestingly, negative feedback regulation exists in this step of the ethylene signal-transduction pathway, in that EIN3 targets the promoter of EBF2 to control its expression level likely allowing fine-tuning of ethylene responses (Binder, B. M. et al., *Plant Cell*, 19:509-523 (2007); Konishi, M. and Yanagisawa, S., *Plant J.*, 55:821-831 (2008)). Most recently, an alternative ethylene signaling pathway has been proposed that is based on studies of ethylene responses in *Arabidopsis* protoplasts (Varma Penmetsa, R. et al., *Plant J.*, 55:580-595 (2008); Yoo, S. D. et al., *Nature*, 451:789-795 (2008)). Characterization of these genes/proteins has provided additional insight into the molecular mechanisms that may underlie the response of plants to ethylene gas.

EIN2 is an integral membrane protein with limited similarity in the N-terminus to mammalian NRAMP metal transporters, the <850 amino acid C-terminus of EIN2 is conserved in all the known EIN2 homologs of angiosperms (Varma Penmetsa, R. et al., *Plant J.*, 55:580-595 (2008)). Interestingly, expression of a portion of the C-terminus (EIN2-CEND) is sufficient to constitutively activate ethylene and stress responses both in *Arabidopsis* (Alonso, J. M. et al., *Science*, 284:2148-2152 (1999)) and in *Medicago* (Mt) (Varma Penmetsa, R. et al., *Plant J.*, 55:580-595 (2008)). Phenotypic, epistatic and biochemical analyses place EIN2 in a central position in ethylene signaling pathway (Roman, G. et al., *Genetics*, 139:1393-1409 (1995); Johnson, P. R. and Ecker, J. R., *Annu. Rev. Genet.*, 32:227-254 (1998); Guo, H. and Ecker, J. R., *Cell*, 115:667-677 (2003)).

BRIEF SUMMARY OF THE INVENTION

The present invention provides for transgenic plants with altered ethylene sensitivity. In some embodiments, the plants can have one or more expression cassette that results in ectopic or increased expression of an ETP1 or ETP2 polypeptide comprising an expression cassette. Expression of ETP1 or ETP2 will result in plants with reduced sensitivity to ethylene. Alternatively, in some embodiments, the invention will involve a plant with one or more expression cassettes which express a polynucleotide that reduced expression of an endogenous ETP1 and/or ETP2 polypeptide. For example, the expression cassette can express an siRNA, microRNA, antisense or sense construct, or a combination thereof (e.g., to form a dsRNA), such that endogenous ETP1 and/or ETP2 polypeptide expression is reduced or suppressed.

Accordingly, in some embodiments, the invention provides a plant comprising a heterologous recombinant expression cassette, wherein the plant has altered sensitivity to ethylene compared to a control plant lacking the expression cassette, the expression cassette comprising a promoter operably linked to a polynucleotide, which polynucleotide, when expressed, modulates expression of an ETP1 or ETP2 polypeptide, wherein modulated expression of the ETP1 or ETP2 polypeptide results in altered ethylene sensitivity.

In some embodiments, expression of the ETP1 and/or ETP2 polypeptide is increased compared to a control plant lacking the expression cassette, wherein the plant has reduced ethylene sensitivity compared to the control plant. In some embodiments, the polynucleotide encodes a polypeptide comprising an amino acid sequence substantially identical (e.g., at least 80%, 85%, 90%, 95% or 100% identical) to any of SEQ ID NOS:1-8 or 18-22.

In some embodiments, expression of the ETP1 and/or ETP2 polypeptide is decreased compared to a control plant lacking the expression cassette, wherein the plant has increased ethylene sensitivity compared to the control plant. In some embodiments, the polynucleotide comprises at least 20 (e.g., at least 50, 100, or 200) contiguous nucleotides, or the complement thereof, of a nucleic acid encoding any of SEQ ID NOS:1-8 or 18-22, such that expression of the polynucleotide inhibits expression of an endogenous ETP1 or ETP2 gene. In some embodiments, the polynucleotide comprises a sequence at least 80% identical to at least 100 contiguous nucleotides, or the complement thereof, of a nucleic acid encoding any of SEQ ID NOS:1-8 or 18-22. In some embodiments, the endogenous ETP1 or ETP2 gene encodes a polypeptide at least 80% identical to any of SEQ ID NOS:1-8 or 18-22, respectively. In some embodiments, the sequence is at least 95% identical to at least 100 contiguous nucleotides encoding any of SEQ ID NOS:1-8 or 18-22. In some embodiments, the sequence is 100% identical to at least 100 contiguous nucleotides encoding any of SEQ ID NOS:1-8 or 18-22. In some embodiments, the polynucleotide encodes an siRNA, antisense polynucleotide, a microRNA, or a sense suppression nucleic acid, thereby suppressing expression of an endogenous ETP1 or ETP2 protein. In some embodiments, the plant comprises at least two heterologous expression cassettes wherein expression from one expression cassette inhibits expression of an endogenous ETP1 and expression from a second expression cassette inhibits expression of an endogenous ETP2 gene.

The present invention also provides a method of making a plant as described above or elsewhere herein. In some embodiments, the method comprises introducing the expression cassette into a plurality of plants; and selecting a plant that expresses the polynucleotide from the plurality of plants. In some embodiments, the selecting step comprising selecting a plant that has altered ethylene sensitivity.

The present invention also provides a recombinant expression cassette comprising a promoter operably linked to a polynucleotide, which polynucleotide, when expressed in a plant, modulates expression of an endogenous ETP1 or ETP2 gene.

In some embodiments, expression of ETP1 and/or ETP2 is increased when the expression cassette is introduced into a plant compared to a control plant lacking the expression cassette, and wherein the promoter is heterologous to the polynucleotide. In some embodiments, the polynucleotide encodes a polypeptide substantially identical to any of SEQ ID NOS:1-8 or 18-22.

In some embodiments, expression of ETP1 and/or ETP2 is decreased when the expression cassette is introduced into a plant compared to a control plant lacking the expression cassette, and wherein the promoter is heterologous to the polynucleotide. In some embodiments, the polynucleotide comprises at least 20 (e.g., at least 50, 100, or 200) contiguous nucleotides, or the complement thereof, of a nucleic acid encoding any of SEQ ID NOS:1-8 or 18-22, such that expression of the polynucleotide inhibits expression of an endogenous ETP1 or ETP2 gene. In some embodiments, the endogenous ETP1 or ETP2 gene encodes a polypeptide at least 80% identical to any of SEQ ID NOS:1-8 or 18-22, respectively. In some embodiments, the polynucleotide comprises a sequence at least 80% identical to at least 100 contiguous nucleotides, or the complement thereof, of a nucleic acid encoding any of SEQ ID NOS:1-8 or 18-22. In some embodiments, the sequence is at least 95% identical to at least 100 contiguous nucleotides encoding any of SEQ ID NOS:1-8 or 18-22. In some embodiments, the sequence is 100% identical to at least 100 nucleotides encoding any of SEQ ID NOS:1-8 or 18-22.

The present invention also provides methods of identifying an agent that modulates the interaction of an ETP1 or ETP2-binding fragment of an EIN2 protein to ETP1 or ETP2. In some embodiments, the method comprises contacting a plurality of agents to the fragment in the presence of an ETP1 or ETP2 polypeptide under conditions such that the fragment would bind to the ETP1 or ETP2 polypeptide in the absence of the agents; determining whether the contacting step modulates binding of the fragment to the ETP1 or ETP2 polypeptide compared to the absence of the agents; and selecting an agent that modulates the interaction of an ETP1 or ETP2-binding fragment of an EIN2 protein to ETP1 or ETP2. In some embodiments, the ETP1 or ETP2 polypeptide is at least 80% identical to an of SEQ ID NOS:1-8 or 18-22. In some embodiments, the fragment comprises a polypeptide at least 80% (e.g., at least 95% or 100%) identical to amino acids 1047-1294 of *Arabidopsis* EIN2. In some embodiments, the method further comprises contacting the selected agent to a plant and determining the effect of the agent on an ethylene-effected phenotype. In some embodiments, the contacting step is performed as part of a yeast two-hybrid assay Other inventions provided herein will be clear upon review of the rest of the specification and claims.

DEFINITIONS

The term "promoter" or "regulatory element" refers to a region or sequence determinants located upstream or downstream from the start of transcription and which are involved in recognition and binding of RNA polymerase and other proteins to initiate transcription. Promoters need not be of plant origin, for example, promoters derived from plant viruses, such as the CaMV35S promoter, can be used in the present invention.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition.

An "ETP1 or ETP2 polypeptide" is a polypeptide substantially identical to any of SEQ ID NOs: 1-8 or 18-22, polypeptides encoded by Genbank Accession numbers 02g54240 (rice), E00121008 FBA3 (poplar), G125000065N (poplar), or ABD32500 (*Medicago*), or as otherwise described herein. ETP1 and ETP2 polypeptides are F-box proteins that bind to the C-terminal region of an EIN2 polypeptide, e.g., as described herein in a yeast two-hybrid assay. F-box proteins comprise an approximately 40-50 amino acid conserved F-box motif See, e.g., Kipreos, et al., *Genome Biol.* 1:5 (2000) generally, and FIG. 1 of Kipreos in particular.

An "EIN2 polypeptide" is a polypeptide substantially identical to the *Arabidopsis* EIN2 polypeptide or an ortholog thereof.

The "ethylene response" refers to a plant trait that is mediated by ethylene gas, including but not limited to germination, flower and leaf senescence, fruit ripening, fruit drop, leaf abscission, root nodulation, programmed cell death, responsiveness to stress, responsiveness to pathogen attack, and the "triple response" of etiolated dicotyledoneous seedlings (e.g., inhibition of hypocotyl and root cell elongation, radial swelling of the hypocotyl, and exaggerated curvature of the apical hook). Ethylene causes developmental changes that result in fruit ripening. New enzymes are made because of the ethylene signal. These include hydrolases to facilitate break down of fruit components, amylases to accelerate hydrolysis of starch into sugar, pectinases to catalyze degradation of pectin, and so on. Ethylene increases the transcription of genes that are then transcribed and translated to make these enzymes. The enzymes then catalyze reactions to alter the characteristics of the fruit. Enzymes produced as a result of exposure to ethylene facilitate the ripening responses. Chlorophyll is broken down and sometimes new pigments are made so that the fruit skin changes color from green to red, yellow, or blue. Acids are broken down so that the fruit changes from sour to neutral. The degradation of starch by amylase produces sugar. This reduces the mealy (floury) quality and increases juiciness of the fruit. The breakdown of pectin by pectinase results in a softer fruit. Enzymes also break down large organic molecules into volatile smaller molecules which are detected as an aroma.

Fruit drop is related to fruit ripening. The fruit-ripening process described above, also occurs in a layer of cells in the pedicel near the point of attachment to the stem of the plant. This layer of cells in the pedicel is often called the abscission zone because this layer will eventually separate and the fruit will drop from the plant. The cells in this cross sectional layer in the pedicel receive the ethylene signal from the ripening fruit. Reception of the signal results in the production of new enzymes. The cells "ripen" and pectinases attack the cells of the abscission zone. When the cell connection have been sufficiently weakened, the weight of the fruit will cause it to fall from the plant.

Plant senescence is a genetically programmed process; it is the last phase of plant development and ultimately leads to death. Plant hormones such as ethylene and cytokinins play roles in the regulation of senescence.

One of skill in the art will appreciate that one can test for ethylene sensitivity in a plant in many ways. Increased or decreased ethylene sensitivity is determined in a plant comprising an expression cassette "compared to a control plant lacking the expression cassette." The control plant will be of the same species and will generally be isogenic compared to the plant comprising the expression cassette except for the absence of the expression cassette.

Optimal alignment of sequences for comparison may be conducted by the local homology algorithm of Smith and Waterman *Add. APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polypeptide sequences means that a polypeptide comprises a sequence that has at least 25% sequence identity. Alternatively, percent identity can be any integer from 25% to 100%. Exemplary embodiments include at least: 25%, 30%, 35%, 40%, 45%, 50%, 55%, 60%, 65%, 70%, 75%, 80%, 85%, 90%, 95%, or 99%. compared to a reference sequence using the programs described herein; preferably BLAST using standard parameters, as described below. Accordingly, ETP sequences of the invention include nucleic acid sequences encoding a polypeptide that has substantial identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8. ETP sequences of the invention also include polypeptide sequences having substantial identify to SEQ ID NO:1, SEQ ID NO:2, SEQ ID NO:3, SEQ ID NO:4, SEQ ID NO:5, SEQ ID NO:6, SEQ ID NO:7, SEQ ID NO:8. One of skill will recognize that these values can be appropriately adjusted to determine corresponding identity of proteins encoded by two nucleotide sequences by taking into account codon degeneracy, amino acid similarity, reading frame positioning and the like. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

BRIEF DESCRIPTION OF THE DRAWINGS

FIGS. 9A-C. The alignment of EIN2 from different plant species (SEQ ID NOS:9-15). Alignment of EIN2 amino acid sequences from different species generated with the ClustalW program. The positions of amino acid residues are indicated with numbers; asterisks and dots indicate identical and conserved amino acids, respectively.

DETAILED DESCRIPTION

I. Introduction

Figure 1:
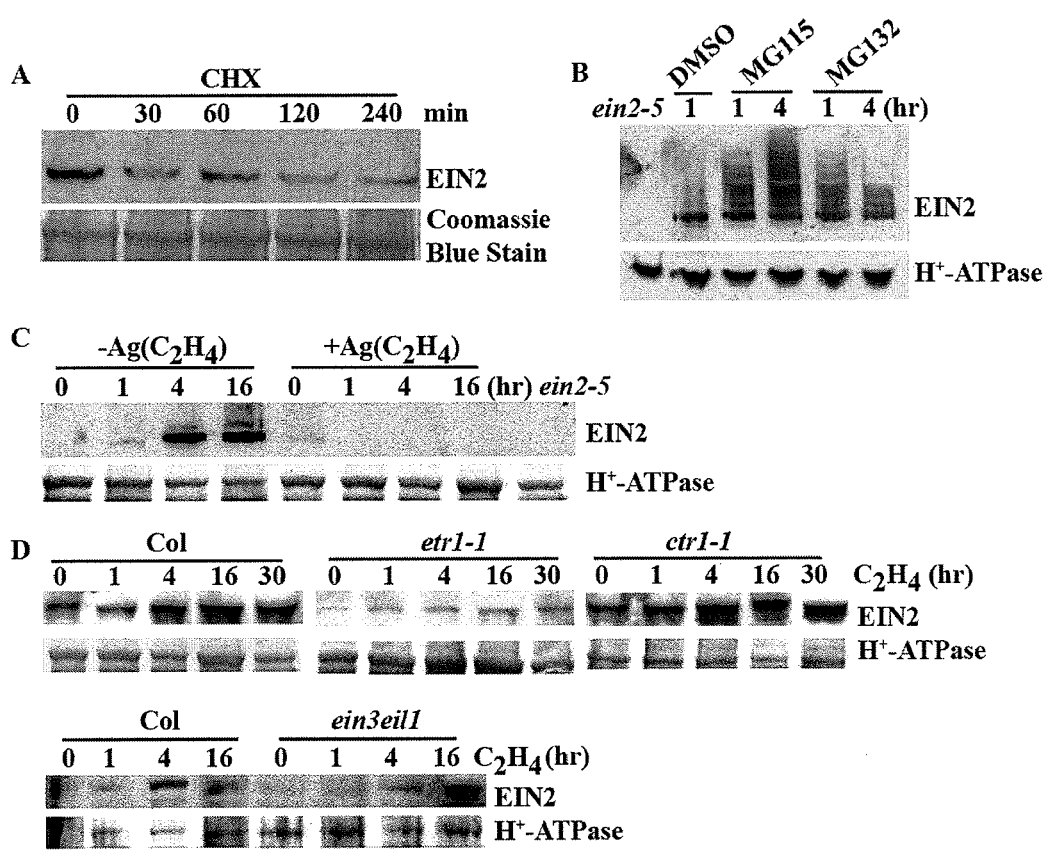
FIG. 1. EIN2 is a short-lived protein whose accumulation is essential for ethylene responses. (A) EIN2 is a short half-life protein. Etiolated wild-type Col-0 seedlings grown in air supplied in the presence of 100 µM cyclohexamide (CHX) for different amounts of time. Total protein lysates were subjected to immunoblotting with EIN2 anti-serum. Coomassie blue staining of total membrane proteins was used as a lane loading control. (B) The protein level of EIN2 is stabilized by specific proteasome inhibitors. Total membrane protein extracts were derived from wild-type Col-0 etiolated seedlings treated with mock (1% DMSO), MG132 (50 µM), MG115 (50 µM) for one hour or 4 hrs, and used for immunoblot assays. (C) EIN2 accumulation is abolished by $Ag^+$ treatment. Etiolated wild-type seedlings were grown on MS media without or with 100 µM $AgNO_3$ for 3 days and treated with air or ethylene for the indicated amount of time. (D) EIN2 protein level is impaired in etr1-1 mutant seedlings and constitutively accumulates in ctr1-1 mutant seedlings. Wild-type Col-0, ctr1-1, etr1-1 and ein3-1eil1-1 mutant etiolated seedlings were grown on MS media in air for 3 days and subsequently treated with ethylene gas for the indicated amount of time. Western blotting using an anti-$H^+$-ATPase antibody was used as a lane loading control.

The present invention is based, in part, on the discovery that certain F-box proteins (ETP1 and ETP2) interact with Ein2 to regulate ethylene responses in plants. As described in the Examples, increased expression of ETP1 or ETP2 results in decreased ethylene sensitivity, whereas suppression of endogenous ETP1 and ETP2 expression results in plants with increased ethylene sensitivity. These discoveries can now be used to generate plants with increased or decreased ethylene sensitivity as desired.

Those of skill in the art are aware of numerous desirable characteristics associated with decreased ethylene sensitivity. For example, decreased ethylene sensitivity is useful to (a) protect flowers and plants from senescence or deterioration, including but not limited to, when shipped in closed containers, (b) increase the yields of plants by preventing flower abortion, fruit drop and abscission of desirable vegetative parts, and (c) improve the quality of turf by maintaining chlorophyll levels, increasing clipping yields, preventing leaf senescence and increasing disease resistance. Furthermore, a decrease in ethylene response can be used to delay disease developments, including but not limited to preventing of lesions and senescence and to reduce diseases in plants in which ethylene causes an increase in disease development, including but not limited to, in barley, citrus, Douglas fir seedlings, grapefruit, plum, rose, carnation, strawberry, tobacco, tomato, wheat, watermelon and ornamental plants. In some embodiments, decreased ethylene sensitivity is useful for inducing enhanced drought tolerance.

Those of skill in the art are also aware of numerous desirable characteristics associated with increased ethylene sensitivity. Notably, increased ethylene sensitivity can include increased fruit ripening. Thus, for example, ripening can be induced upon inducement of ETP1 or ETP2 expression.

Further, the inventors have found that EIN2 and ETP1 and ETP2 interact physically and that this interaction plays a role in ethylene responsiveness. Therefore, the invention provides for methods of identifying agents that increase or decrease this interaction, thereby allowing for agents that decrease or increase, respectively, ethylene sensitivity and ethylene responsiveness.

II. Use of Nucleic Acids of the Invention

A. Use of Nucleic Acids of the Invention to Inhibit or Suppress Gene Expression

The invention provides methods for increasing ethylene sensitivity in a plant by suppressing expression of a nucleic acid molecule encoding an ETP1 and/or ETP2 polypeptide. In a transgenic plant of the invention, a nucleic acid molecule, or antisense, siRNA, microRNA, or dsRNA constructs thereof, encoding an ETP1 and/or ETP2 gene product, or fragment thereof, or encoding an ETP1 or ETP2 mRNA, or fragment thereof can be operatively linked to an exogenous regulatory element, wherein expression of the construct suppresses endogenous ETP1 and/or ETP2 expression. The invention provides, for example, a transgenic plant characterized by increased ethylene sensitivity or ethylene-independent induction of an ethylene triggered phenotype having an expressed nucleic acid molecule encoding an ETP1 and/or ETP2 gene product, or antisense, siRNA, microRNA, or dsRNA construct thereof, that is operatively linked to an exogenous constitutive regulatory element.

The ETP1 and/or ETP2 nucleic acid sequences of the invention can be used to prepare expression cassettes useful in a number of techniques, including inhibiting, suppressing or increasing, expression or for ectopic expression. A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805-8809 (1988); Pnueli et al., *The Plant Cell* 6:175-186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of an ETP1 and/or ETP2-encoding sequence can be useful for producing a plant in which an ETP1 and/or ETP2 expression is suppressed. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. In some embodiments, a sequence of at least, e.g., 15, 20, 25 30, 50, 100, 200, or more continuous nucleotides (up to mRNA full length) substantially identical to an endogenous ETP1 or ETP2 mRNA, or a complement thereof, can be used.

Catalytic RNA molecules or ribozymes can also be used to inhibit expression of ETP1 and/or ETP2 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature*, 334:585-591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Endogenous gene expression may also be suppressed by way of RNA interference (RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementry RNAs or may be a single RNA with internally complementary sequences that form a double-stranded RNA. Although details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959-13964 (1998); Tabara et al. *Science* 282:430-431 (1998)). For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest.

The resulting plants may then be screened for a phenotype associated with the target protein and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases.

Expression vectors that continually express siRNA in transiently- and stably-transfected have been engineered to express small hairpin RNAs, which get processed in vivo into siRNAs molecules capable of carrying out gene-specific silencing (Brummelkamp et al., *Science* 296:550-553 (2002), and Paddison, et al., *Genes & Dev.* 16:948-958 (2002)). Post-transcriptional gene silencing by double-stranded RNA is discussed in further detail by Hammond et al. *Nature Rev Gen* 2: 110-119 (2001), Fire et al. *Nature* 391: 806-811 (1998) and Timmons and Fire *Nature* 395: 854 (1998).

One of skill in the art will recognize that using technology based on specific nucleotide sequences (e.g., antisense or sense suppression, siRNA, microRNA technology, etc.), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variance between family members.

Yet another way to suppress expression of an endogenous plant gene is by recombinant expression of a microRNA that suppresses a target (e.g., an ETP1 or ETP2 gene). Artificial microRNAs are single-stranded RNAs (e.g., between 18-25 mers, generally 21 mers), that are not normally found in plants and that are processed from endogenous miRNA precursors. Their sequences are designed according to the determinants of plant miRNA target selection, such that the artificial microRNA specifically silences its intended target gene(s) and are generally described in Schwab et al, *The Plant Cell* 18:1121-1133 (2006) as well as the internet-based methods of designing such microRNAs as described therein. See also, US Patent Publication No. 2008/0313773.

B. Use of Nucleic Acids of the Invention to Enhance Gene Expression

Nucleic acid sequences encoding all or an active part of an ETP1 or ETP2 polypeptide (including but not limited to polypeptides substantially identical to any of SEQ ID NOS: 1-8 or 18-22, which when expressed decrease ethylene sensitivity) can be used to prepare expression cassettes that enhance, or increase endogenous, an ETP1 or ETP2 gene expression. Where overexpression of a gene is desired, the desired gene from a different species may be used to decrease potential sense suppression effects.

Any of a number of means well known in the art can be used to increase an ETP1 or ETP2 activity in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, one or several an ETP1 or ETP2 genes can be expressed constitutively (e.g., using the CaMV 35S promoter).

One of skill will recognize that the polypeptides encoded by the genes of the invention, like other proteins, have different domains which perform different functions. Thus, the gene sequences need not be full length, so long as the desired functional domain of the protein is expressed.

III. Preparation of Recombinant Vectors

In some embodiments, to use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention can optionally comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

In some embodiments, an ETP1 or ETP2 nucleic acid sequences of the invention are expressed recombinantly in plant cells to enhance and increase levels of an ETP1 or ETP2 polypeptides. Alternatively, antisense or other an ETP1 or ETP2 constructs are used to suppress an ETP1 or ETP2 levels of expression. A variety of different expression constructs, such as expression cassettes and vectors suitable for transformation of plant cells can be prepared. Techniques for transforming a wide variety of higher plant species are well known and described in the technical and scientific literature. See, e.g., Weising et al. *Ann. Rev. Genet.* 22:421-477 (1988). An ETP1 or ETP2 sequence coding for an ETP1 or ETP2 polypeptide, e.g., a cDNA sequence encoding a full length protein, can be combined with cis-acting (promoter) and trans-acting (enhancer) transcriptional regulatory sequences to direct the timing, tissue type and levels of transcription in the intended tissues of the transformed plant. Translational control elements can also be used.

The invention provides an ETP1 or ETP2 nucleic acid operably linked to a promoter that, in some embodiments, is capable of driving the transcription of the ETP1 or ETP2 coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal. In some embodiments, as discussed above, desired promoters are identified by analyzing the 5' sequences of a genomic clone corresponding to an ETP1 or ETP2 gene as described here.

A. Constitutive Promoters

A promoter fragment can be employed that will direct expression of an ETP1 or ETP2 nucleic acid in all transformed cells or tissues, e.g. as those of a regenerated plant. The term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types. Promoters that drive expression continuously under physiological conditions are referred to as "constitutive" promoters and are active under most environmental conditions and states of development or cell differentiation.

A variety of constitutive regulatory elements useful for ectopic expression in a transgenic plant are well known in the art. The cauliflower mosaic virus 35S (CaMV 35S) promoter, for example, is a well-characterized constitutive regulatory element that produces a high level of expression in all plant tissues (Odell et al., *Nature* 313:810-812 (1985)). The CaMV 35S promoter can be particularly useful due to its activity in numerous diverse plant species (Benfey and Chua, *Science* 250:959-966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other useful constitutive regulatory elements include, for example, the cauliflower mosaic virus 19S promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient expression in monocots also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding an ETP1 or ETP2 polynucleotide (Comai et al., *Plant Mol. Biol.* 15:373 (1990)).

Other examples of constitutive promoters include the 1'- or 2'-promoter derived from T-DNA of *Agrobacterium tumefaciens* (see, e.g., Mengiste (1997) supra; O'Grady (1995) *Plant Mol. Biol.* 29:99-108); actin promoters, such as the *Arabidopsis* actin gene promoter (see, e.g., Huang (1997) *Plant Mol. Biol.* 1997 33:125-139); alcohol dehydrogenase (Adh) gene promoters (see, e.g., Millar (1996) *Plant Mol. Biol.* 31:897-904); ACT11 from *Arabidopsis* (Huang et al. *Plant Mol. Biol.* 33:125-139 (1996)), Cat3 from *Arabidopsis* (GenBank No. U43147, Zhong et al., *Mol. Gen. Genet.* 251: 196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Biol.* 208:551-565 (1989)), Gpc2 from maize (GenBank No. U45855, Manjunath et al., *Plant Mol. Biol.* 33:97-112 (1997)), other transcription initiation regions from various plant genes known to those of skill. See also Holtorf *Plant Mol. Biol.* 29:637-646 (1995).

B. Inducible Promoters

Alternatively, a promoter may direct expression of an ETP1 or ETP2 nucleic acid of the invention under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters. For example, the invention incorporates the drought-inducible promoter of maize (Busk (1997) supra); the cold, drought, and high salt inducible promoter from potato (Kirch (1997) *Plant Mol. Biol.* 33:897-909).

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) *Plant Physiol.* 115:397-407); the auxin-responsive *Arabidopsis* GST6 promoter (also responsive to salicylic acid and hydrogen peroxide) (Chen (1996) *Plant J.* 10: 955-966); the auxin-inducible parC promoter from tobacco (Sakai (1996) 37:906-913); a plant biotin response element (Streit (1997) *Mol. Plant Microbe Interact.* 10:933-937); and, the promoter responsive to the stress hormone abscisic acid (Sheen (1996) *Science* 274:1900-1902).

Promoters that are inducible upon exposure to chemicals reagents applied to the plant, such as herbicides or antibiotics, can also be used to express the nucleic acids of the invention. For example, the maize In2-2 promoter, activated by benzenesulfonamide herbicide safeners, can be used (De Veylder (1997) *Plant Cell Physiol.* 38:568-577); application of different herbicide safeners induces distinct gene expression patterns, including expression in the root, hydathodes, and the shoot apical meristem. An ETP1 or ETP2 coding sequence can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465-473); or, a salicylic acid-responsive element (Stange (1997) *Plant J.* 11:1315-1324; Uknes et al., *Plant Cell* 5:159-169 (1993); Bi et al., *Plant J.* 8:235-245 (1995)).

Other inducible regulatory elements include but are not limited to copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992)). An inducible regulatory element useful in the transgenic plants of the invention also can be, for example, a nitrate-inducible promoter derived from the spinach nitrite reductase gene (Back et al., *Plant Mol. Biol.* 17:9 (1991)) or a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)).

C. Tissue-Specific Promoters

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistils, flowers, or any embryonic tissue. Reproductive tissue-specific promoters may be, e.g., ovule-specific, embryo-specific, endosperm-specific, integument-specific, seed and seed coat-specific, pollen-specific, petal-specific, sepal-specific, or some combination thereof.

Other tissue-specific promoters include seed promoters. Suitable seed-specific promoters are derived from the following genes: MAC1 from maize (Sheridan (1996) *Genetics* 142:1009-1020); Cat3 from maize (GenBank No. L05934, Abler (1993) *Plant Mol. Biol.* 22:10131-1038); vivparous-1 from *Arabidopsis* (Genbank No. U93215); atmyc1 from *Arabidopsis* (Urao (1996) *Plant Mol. Biol.* 32:571-57; Conceicao (1994) *Plant* 5:493-505); napA from *Brassica napus* (GenBank No. J02798, Josefsson (1987) *JBL* 26:12196-1301); and the napin gene family from *Brassica napus* (Sjodahl (1995) *Planta* 197:264-271).

A variety of promoters specifically active in vegetative tissues, such as leaves, stems, roots and tubers, can also be used to express the ETP1 or ETP2 nucleic acids of the invention. For example, promoters controlling patatin, the major storage protein of the potato tuber, can be used, see, e.g., Kim (1994) *Plant Mol. Biol.* 26:603-615; Martin (1997) *Plant J.* 11:53-62. The ORF13 promoter from *Agrobacterium rhizogenes* which exhibits high activity in roots can also be used (Hansen (1997) *Mol. Gen. Genet.* 254:337-343. Other useful vegetative tissue-specific promoters include: the tarin promoter of the gene encoding a globulin from a major taro (*Colocasia esculenta* L. Schott) corm protein family, tarin (Bezerra (1995) *Plant Mol. Biol.* 28:137-144); the curculin promoter active during taro corm development (de Castro (1992) *Plant Cell* 4:1549-1559) and the promoter for the tobacco root-specific gene TobRB7, whose expression is localized to root meristem and immature central cylinder regions (Yamamoto (1991) *Plant Cell* 3:371-382).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier (1997) *FEBS Lett.* 415:91-95). A ribulose bisphosphate carboxylase promoters expressed almost exclusively in mesophyll cells in leaf blades and leaf sheaths at high levels, described by Matsuoka (1994) *Plant J.* 6:311-319, can be used. Another leaf-specific promoter is the light harvesting chlorophyll a/b binding protein gene promoter, see, e.g., Shiina (1997) *Plant Physiol.* 115:477-483; Casal (1998) *Plant Physiol.* 116:1533-1538. The *Arabidopsis thaliana* myb-related gene promoter (Atmyb5) described by Li (1996) *FEBS Lett.* 379:117-121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) *Plant J.* 11:1285-1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems and are described by Di Laurenzio (1996) *Cell* 86:423-433; and, Long (1996) *Nature* 379:66-69, can be used. Another promoter is the 3-hydroxy-3-methylglutaryl coenzyme A reductase HMG2 gene promoter, whose expression is restricted to meristematic and floral (secretory zone of the stigma, mature pollen grains, gynoecium vascular tissue, and fertilized ovules) tissues (see, e.g., Enjuto (1995) *Plant Cell.* 7:517-527). Additional promoter examples include the kn1-related gene promoters from maize and other species that show meristem-specific expression, see, e.g., Granger (1996) *Plant Mol. Biol.* 31:373-378; Kerstetter (1994) *Plant Cell* 6:1877-1887; Hake (1995) *Philos. Trans. R. Soc. Lond. B. Biol. Sci.* 350:45-51. One such example is the *Arabidopsis thaliana* KNAT1 promoter. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln (1994) *Plant* Cell 6:1859-1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, an ETP1 or ETP2 nucleic acid is expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai (1995) *Proc. Natl. Acad. Sci. USA* 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) *Plant Mol. Biol.* 31:1129-1139).

V. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983).

Transformed plant cells that are derived from any transformation technique can be cultured to regenerate a whole plant that possesses the transformed genotype and thus the desired phenotype. Such regeneration techniques rely on manipulation of certain phytohormones in a tissue culture growth medium, optionally relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

The nucleic acids of the invention can be used to confer desired traits on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna,* and, *Zea*. Plants having an ethylene response, and thus those that have use in the present invention, include but are not limited to: dicotyledons and monocotyledons including but not limited to rice, maize, wheat, barley, sorghum, millet, grass, oats, tomato, potato, banana, kiwi fruit, avocado, melon, mango, cane, sugar beet, tobacco, papaya, peach, strawberry, raspberry, blackberry, blueberry, lettuce, cabbage, cauliflower, onion, broccoli, brussel sprout, cotton, canola, grape, soybean, oil seed rape, asparagus, beans, carrots, cucumbers, eggplant, melons, okra, parsnips, peanuts, peppers, pineapples, squash, sweet potatoes, rye, cantaloupes, peas, pumpkins, sunflowers, spinach, apples, cherries, plums, cranberries, grapefruit, lemons, limes, nectarines, oranges, peaches, pears, tangelos, tangerines, lily, carnation, chrysanthemum, petunia, rose, geranium, violet, gladioli, orchid, lilac, crabapple, sweetgum tree, maple tree, poinsettia, locust tree, oak tree, ash tree and linden tree.

VI. Screening for Agents that Modulate ETP1 or ETP2 Interaction with EIN2

As explained herein, ETP1 and ETP2 interact with the C-terminus of EIN2 and this interaction affects ethylene sensitivity. Accordingly, the present invention provides for methods of screening for agents that increase or decrease the interaction (e.g., binding) of ETP1 and ETP2 interact with the C-terminus of EIN2. For example, in some embodiments, a plurality of agents (e.g., in combination, separately in parallel, or in series) are contacted to a mixture comprising at least (1) A first member, i.e., the C-terminus (ETP1 and/or ETP2 binding region) of an EIN2 polypeptide, and (2) a second member, i.e., ETP1 and/or ETP2. Depending on the conditions of the assay, one can perform the assay under conditions in which the first and second member bind. In these conditions, one screens for agents that inhibit the binding of the members. Alternatively, the screen can be performed under conditions in which the two members do not bind together and the assay is used to identify agents that increase or induce binding of the members. Binding can be determined as desired in vitro, or in vivo.

Any ETP1 or ETP2 protein binding member can be used as desired and such proteins can optionally be fusion proteins, e.g., having tags, labels, etc. Similarly, any C-terminal region of an EIN2 protein having ETP-1 or ETP2 binding activity can be used, again optionally as a fusion protein, e.g., having tags, labels, etc.

Polypeptide Binding Assays

Optionally, preliminary screens can be conducted by screening for agents capable of binding to an ETP1, and ETP2, or a C-terminal portion of EIN2 capable of binding ETP1 or ETP2, as at least some of the agents so identified are likely to modulate EIN2/ETP1/2 binding.

Binding assays can involve contacting an ETP1, and ETP2, or a C-terminal portion of EIN2 with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to an ETP1, and ETP2, or a C-terminal portion of EIN2 or displacement of labeled substrates. The ETP1, and ETP2, or a C-terminal portion of EIN2 utilized in such assays can be naturally expressed, cloned or synthesized.

In addition, mammalian or yeast two-hybrid approaches (see, e.g., Bartel, P. L. et. al. *Methods Enzymol,* 254:241 (1995)) can be used to identify polypeptides or other molecules that interact or bind when expressed together in a cell. In some embodiments, agents that modulate the interaction of ETP1 and ETP2 with EIN2 are identified in a two-hybrid assay between an ETP1 or ETP2 and at least the C-terminal portion of EIN2, wherein an agent is identified as an agent that activates or enables binding of the two members. Thus, the two polypeptides bind in the presence, but not in the absence of the agent. Alternatively, the assay can be performed to identify agents that inhibit the binding of the two members.

Validation

Agents that are initially identified by any of the foregoing screening methods can be further tested to validate the apparent activity and/or determine other biological effects of the agent. In some cases, the identified agent is tested for the ability to effect plant ethylene sensitivity. A number of such assays and phenotypes are known in the art and can be employed according to the methods of the invention.

Solid Phase and Soluble High Throughput Assays

In the high throughput assays of the invention, it is possible to screen up to several thousand different agents in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 or more different compounds are possible using the integrated systems of the invention. In addition, microfluidic approaches to reagent manipulation can be used.

Agents

Member binding modulators can be any small chemical compound, or a biological entity, such as a protein (including, e.g., an antibody), sugar, nucleic acid or lipid. In some embodiments, the agents are small chemical molecules and/or peptides.

Essentially any chemical compound can be used as a potential modulator in the assays of the invention, although most often compounds that can be dissolved in aqueous or organic (especially DMSO-based) solutions are used. The assays can be designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds.

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

EXAMPLES

The following examples are offered to illustrate, but not to limit the claimed invention.

Example 1

In this study, we demonstrate that EIN2, the key positive regulator of ethylene signal transduction, is a short half-life protein and it undergoes rapid proteasome-mediated turnover. We also identify two F-box proteins, ETP1 and ETP2, as the key regulators of EIN2 protein stability, and through the regulation of EIN2 they negatively effect ethylene signal transduction. Overall, our results suggest ethylene responses are specifically modulated in an EIN2 protein level dependent manner, and reveal a complex interplay between ethylene, the regulation of ETP1/ETP2 F-box proteins, and subsequent targeting and degradation of EIN2 as essential for triggering appropriate ethylene responses in plants.

Results

EIN2 is a Short Half-Life Protein and is Positively Influenced by Ethylene

A previous study demonstrated that EIN2 mRNA is not altered in response to ethylene (Alonso, J. M. et al., Science, 284:2148-2152 (1999)). Here we have examined whether EIN2 may be subject to posttranscriptional regulation. We first tested its stability by western blotting after treatment with cyclohexamide (CHX), which inhibits de novo protein biosynthesis. We found that EIN2 levels dramatically decreased after 30 minutes of CHX treatment and remained barely detectable for the subsequent 2 hours (FIG. 1A). The rapid reduction of EIN2 protein levels indicates that EIN2 is a short-lived protein, with a half-life of ~30 minutes or less. To further test whether the level of EIN2 is regulated by 26S proteasome-mediated protein turnover, we examined EIN2 protein levels from wild-type Col-0 etiolated seedlings treated with specific proteasome inhibitors MG115 or MG132 (Lee, D. H. and Goldberg, A. L., Trends Cell Biol., 8:397-403 (1998)). As shown in FIG. 1B, after 1 hr of MG132 or MG115 treatment, the accumulation of EIN2 protein markedly increased. Interestingly, this analysis also revealed the presence of higher molecular weight forms of the protein, suggesting that EIN2 might be modified, possibly by ubiquitinylation. These results suggested that EIN2 is a short half-life protein whose turnover is mediated by the proteasome.

Figure 7:
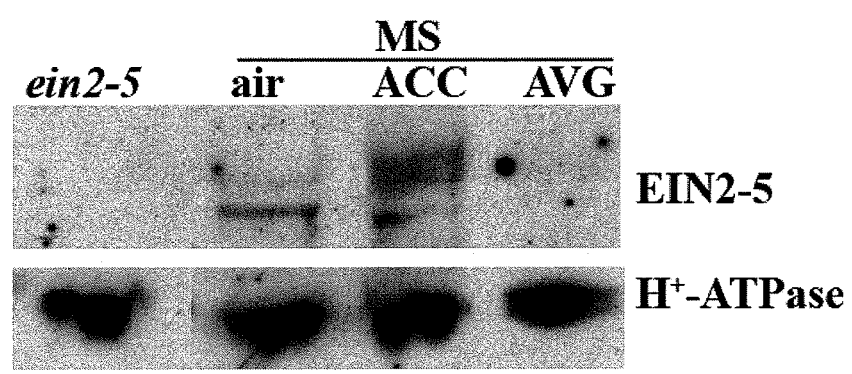
FIG. 7. The effect of ethylene on EIN2 protein accumulation. The abundance of EIN2 protein correlates with the triple response. Etiolated wild-type seedlings (Col-0) were grown on MS medium supplemented with 10 µM ACC or 10 µM AVG for 3 days. Total membrane protein extracts were subjected to immunoblot with EIN2 antiserum. H$^+$-ATPase was used as a lane loading control.

Since EIN2 is a key regulator of the ethylene signaling pathway, we tested the effect of treatment with exogenous ethylene gas on EIN2 protein stability. To do this, we monitored the level of EIN2 protein in plants treated with ethylene (10 ppm) for increasing amounts of time with or without the presence of silver ($Ag^+$), which is a potent inhibitor of ethylene action (Abeles, F. B. et al., Ethylene in plant biology, Academic Press, Inc, New York, N.Y. (2d ed, 1992)). We found that the level of EIN2 protein rapidly increased in response to ethylene treatment, but in the presence of silver ion, EIN2 protein accumulation was completely inhibited (FIG. 1C). In addition, to test the effect of ethylene on EIN2 protein, we monitored EIN2 levels in wild-type Col-0 seedlings grown on MS medium supplemented with either 1-aminocyclopropane-1-carboxylic acid (ACC), an ethylene precursor, or aminoethoxyvinylglycine (AVG), an inhibitor of ethylene biosynthesis. EIN2 protein was not present at detectable levels in the presence of AVG. In contrast, the level of EIN2 was elevated in the presence of ACC (FIG. 7), further suggesting that ethylene stabilizes EIN2 protein. To gain further insight into kinetics of EIN2 protein induction by ethylene, we examined EIN2 levels in different ethylene mutants. In wild-type Col-0 seedlings, the level of EIN2 protein increased in response to ethylene treatment (FIG. 1D). However, in etr1-1 mutant seedlings, EIN2 accumulation was not observed even with 30 hours ethylene treatment. In the contrast, the level of EIN2 was constitutively elevated in ctr1-1 mutant seedlings. Additionally, EIN2 levels were further increased in ctr1-1 mutant seedlings by ethylene treatment. In the ein3eil1 double mutant, EIN2 accumulation was similar to that seen for wild-type Col-0 seedlings (FIG. 1D). These results demonstrated that the accumulation of EIN2 protein is dramatically altered in the different ethylene response mutants. Specifically, the level of EIN2 protein is decreased in ethylene insensitive mutants, but increased in the ethylene constitutive response mutants. Taken together, the results demonstrate that EIN2 protein is stabilized and accumulates by the presence of exogenous ethylene gas. This accumulation of EIN2 is dependent on an intact ethylene signaling pathway upstream of EIN3/EIL1. Overall, these results suggest that EIN2 protein levels are positively correlated with the ethylene response.

Two Novel F-Box Proteins Interact with the C-Terminal End of EIN2

Figure 2:
FIG. 2. Two novel F-box proteins, ETP1 (EIN2 TARGETING PROTEIN1—SEQ ID NO:1) and ETP2 (EIN2 TARGETING PROTEIN2—SEQ ID NO:2) interact with EIN2-CEND (EIN2-C). (A) Alignment of ETP1 and ETP2 amino acid sequences generated with the ClustalW program. The positions of amino acid residues are indicated with numbers; asterisks and dots indicate identical and conserved amino acids, respectively. The putative F-box motif and the FBA_1 (F-box protein associated) domain are indicated by arrow above the sequences (B) EIN2-CEND interact with ETP1 and ETP2 in yeast. Growth on selective plates lacking adenine, histidine, tryptophan with 20 mM 3-AT (-Leu, -Trp, -His, +3AT) and on control plates lacking only tryptophan and leucine (-Trp, -Leu) is shown. (C) EIN2 interacts with ETP1 and ETP2 in vitro. GST-EIN2-CEND (GST-EIN2-C) fusion protein and GST alone protein were purified from *E. coli*. These proteins, as well as GST alone were assayed to pull-down with in vitro translated and HA-tagged ETP1 and ETP2 proteins. The same quantities of the GST fusion proteins (lower panel) and the same amount of HA tagged ETP1 or ETP2 (middle panel) were used as inputs. The HA-tagged ETP1 and ETP2 were detected by anti-HA antibody (upper panel). "+" indicates the addition of protein; "−" indicates the protein was not added. (D) EIN2 highly conserved CEND (EIN2-C5) is sufficient to interact with ETP1 and ETP2 in yeast. The diagrams indicate different deletions of EIN2 CEND. "+" indicates interaction; "−" indicates no interaction. WB: western-blot.

To further understand the posttranscriptional regulation of EIN2 levels, we performed a yeast two-hybrid screen to identify proteins that potentially interact with the EIN2-CEND. As a result, a novel F-box protein ETP1 (At3g18980, GB:Q9LJ68; GB:Q8LB99) was identified. Sequence analysis reveals the presence of a paralogous gene, ETP2 (At3g18910, GB:Q9LJ34), that is 50% identical to ETP1 at the amino acid sequence level (FIG. 2A). Therefore, we tested whether the ETP2 protein might also interact with EIN2-CEND. As shown in FIGS. 2B-C, both directed yeast two hybrid assays and pull down experiments demonstrated that EIN2-CEND was able to interact with both F-box proteins, ETP1 and ETP2.

Figure 8:
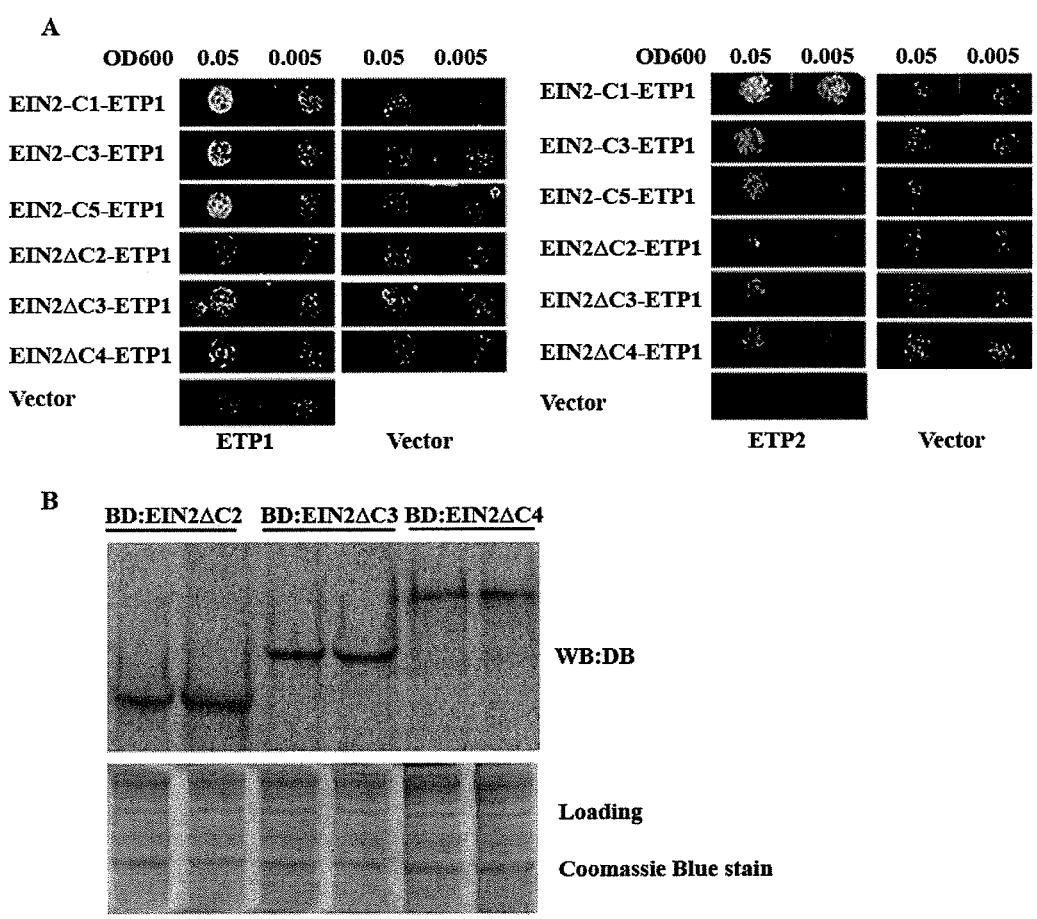
FIG. 8. The most conserved domain of EIN2 is essential for the interaction of EIN2 and ETP1/ETP2. (A) Yeast strains which carried different combination of constructs (as indicated) were grown in SD-Leu/-Trp liquid medium overnight and subjected to SD-leu/-Trp/-His/+3AT (20 mM) selective medium by the indicated start titer (OD600). (B) Expression of truncated forms of EIN2 protein in yeast. Yeast strains which carried different truncations of EIN2 and ETP1 or ETP2 were cultured in SD-Leu/-Trp liquid medium overnight and total protein lysates were separated by PAGE and subjected to blotting using anti-GAL4 DNA-binding domain (DB) antibody. The EIN2:GAL4 fusion proteins tested are indicated, Coomassie blue staining was used as a lane loading control.
Figure 9A:
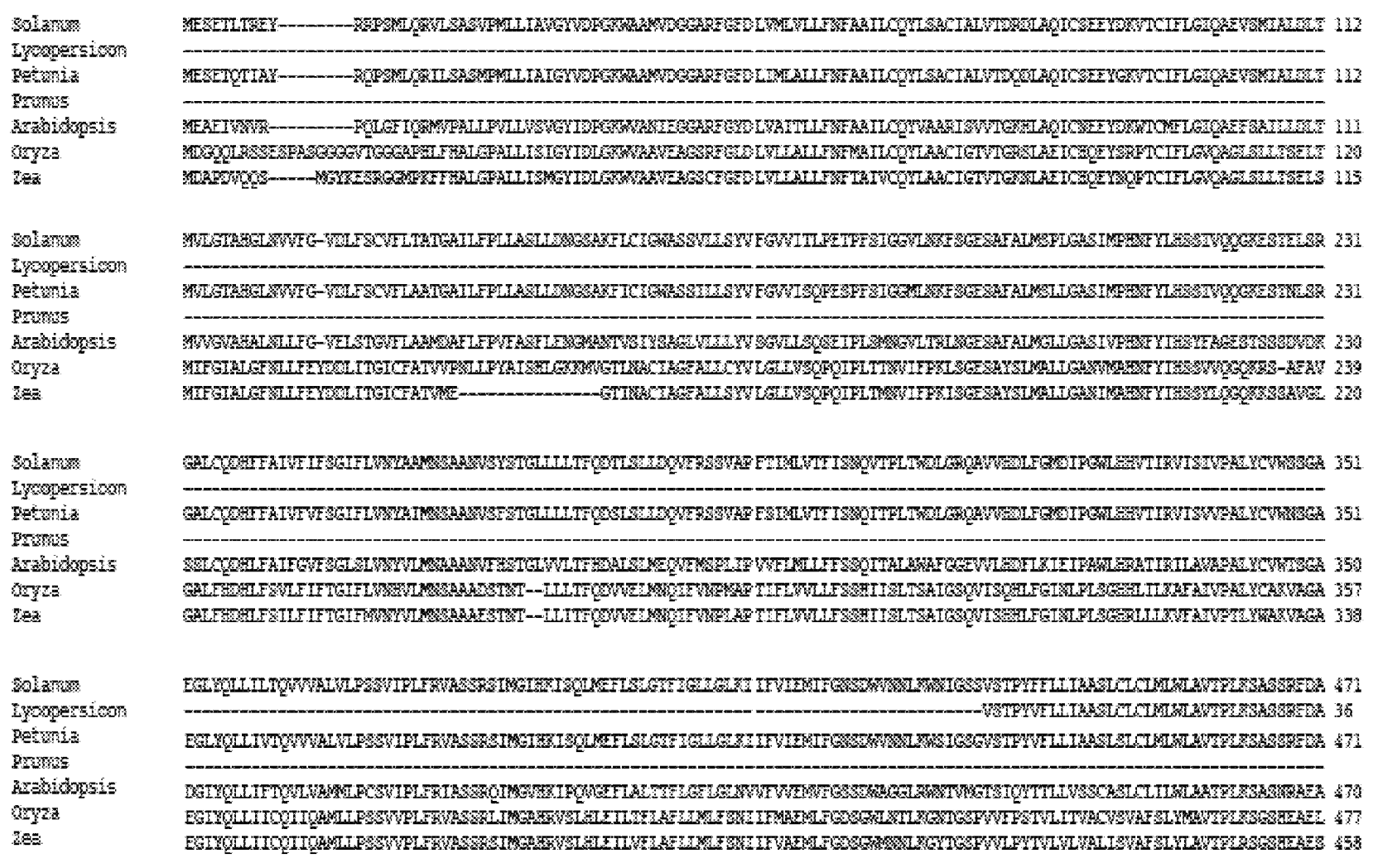

We further characterized the domain of EIN2-CEND that interacts with ETP1 and ETP2. Based on the alignment of EIN2 proteins from different plant species (FIG. 9), a series of deletion mutants of EIN2-CEND was generated to map the region of EIN2 required for interaction with ETP1 and ETP2. As shown in FIG. 2D and FIGS. 8A-B, EIN2-CEND1 (EIN2-C1), EIN2-CEND3 (EIN2-C3), and EIN2-CEND5 (EIN2-C5) interact with both ETP1 and ETP2. In contrast, we found that the EIN2ΔCEND2 (EIN2ΔC2), EIN2ΔCEND3 (EIN2ΔC3) and EIN2ΔCEND4 (EIN2ΔC4) completely lost the ability to interact with EIN2 (FIGS. 8A-B). These results demonstrated that the most highly conserved region of EIN2 (EIN2-C5), the last <250 amino acids (FIG. 9) is both necessary and sufficient for the interaction of EIN2 with ETP1 and ETP2. Additionally, these results suggested that other portions of EIN2-CEND are not essential for these interactions but may enhance them.

ETP1 and ETP2 are the Regulators of EIN2 Stability

Figure 3:
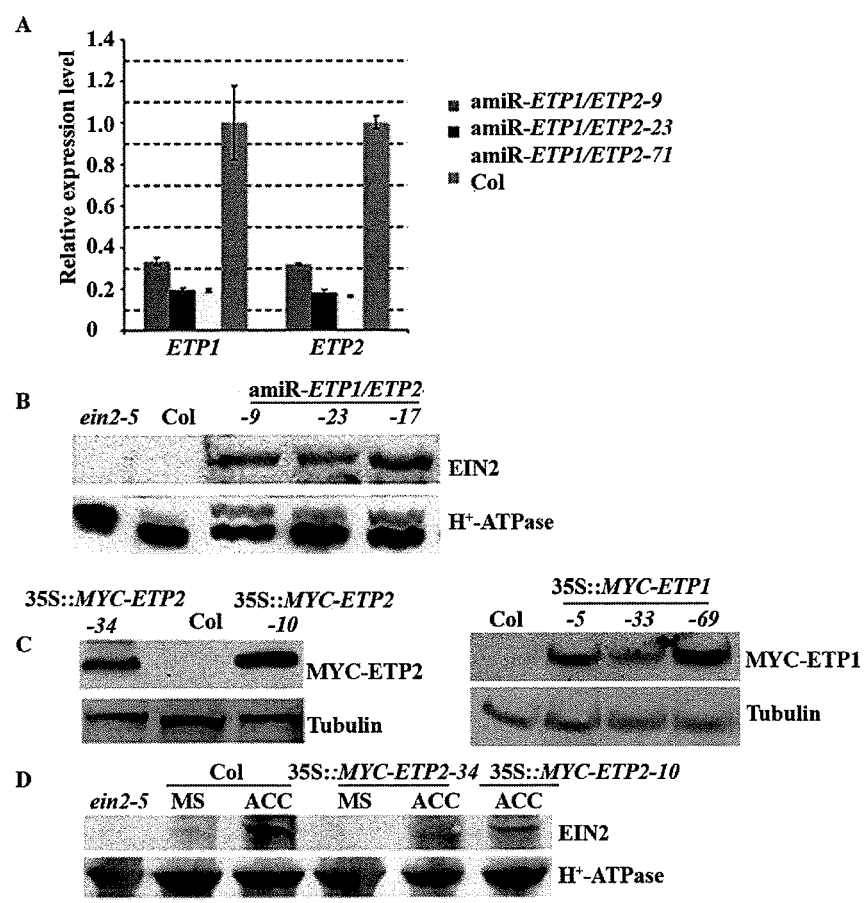
FIG. 3. ETP1 and ETP2 are regulators of EIN2 levels. (A) qPCR analysis of ETP1 and ETP2 transcript levels in amiR-ETP1/ETP2 mutant plants. Total RNA was extracted from the leaves of 3-week-old light-grown plants. The data were normalized to the corresponding actin (input) controls. The data shown are the means±SD of three independent experiments. (B) EIN2 protein accumulates in amiR-ETP1/ETP2 mutant plants. (C) MYC-ETP1 or ETP2 accumulates in 35S::MYC-ETP1 or MYC-ETP2 transgenic plants, respectively. Wild-type Col-0 *Arabidopsis* plants were transformed with a binary vector carrying the MYC tag that fused with ETP1 or ETP2 open reading frame. Total proteins from 35S::MYC-ETP1 or MYC-ETP2 transgenic plants were subjected to immunoblotting with anti-MYC antibody. The same membranes were stripped and subjected to immunoblotting with an anti-tubulin antibody as loading control. (D) Overexpression of ETP2 causes reduction of EIN2 protein. Wild-type Col-0, and ETP2 overexpression plants grown on soil for 3 weeks and the total protein lysates from leaves were subjected to immunoblotting with EIN2 anti-serum. The same membrane was stripped and subjected to immunoblotting with an anti-$H^+$-ATPase antibody as a lane loading control.
Figure 10:
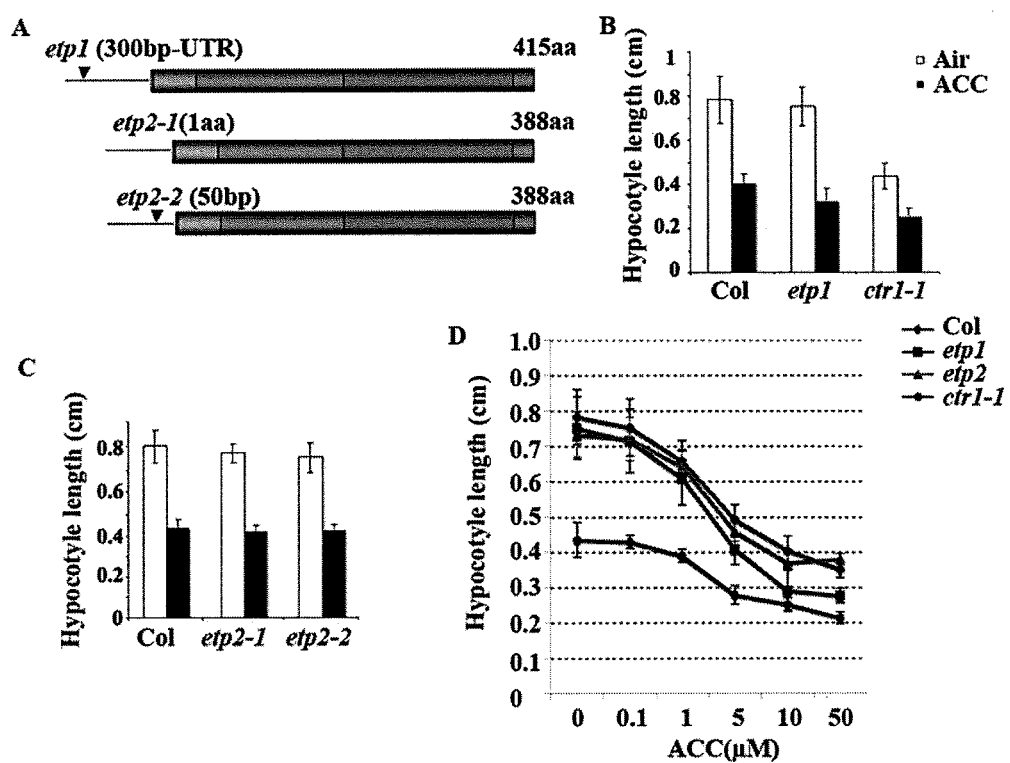
FIG. 10. Mutation of ETP1 Leads to Slightly Hypersensitive to Ethylene Phenotype. (A) Schematic representation of T-DNA insertions in the related F-box genes ETP1 and ETP2, respectively. Coding regions are indicated by boxes and noncoding regions are indicated by lines. A triangle represents a T-DNA insertion event and the positions are indicated. (B-C) Hypocotyl length measurement of etp1 and etp2 mutants. 3-day-old etiolated seedlings were grown on MS medium supplemented with or without 10 µM ACC. Each measurement is the average length (mean±standard error) of >20 hypocotyls. (D) ACC dosage response of etp1 and etp2 mutants. Etiolated seedlings were grown on MS medium supplemented with the indicated amount of ACC. Each measurement is the average length (mean±standard error) of >20 hypocotyls.
Figure 11:
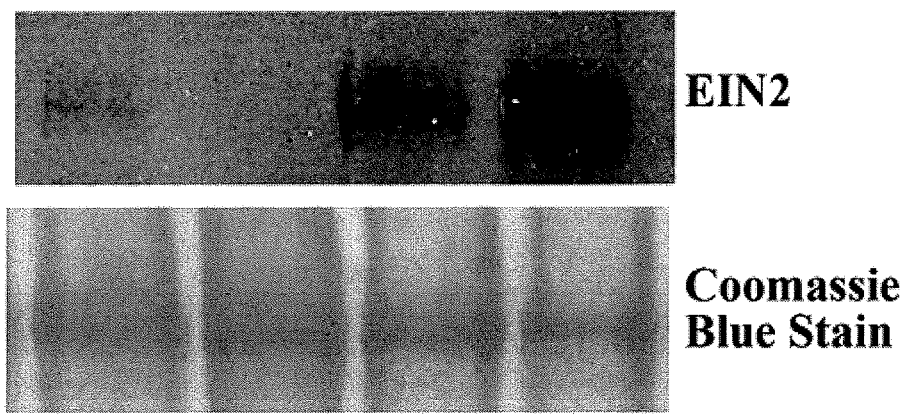
FIG. 11. EIN2 protein accumulates in amiR-ETP1/ETP2 mutant plants. Anti-EIN2 antibody specifically recognizes EIN2 protein in amiR-ETP1/ETP2 mutant plants. Total proteins from wild type (Col), ein2-5 or amiR-ETP1/ETP2 plants were subjected to PAGE, and immunoblotting with anti-EIN2 antibody. Coomassie blue staining was used as a lane loading control.
Figure 13:
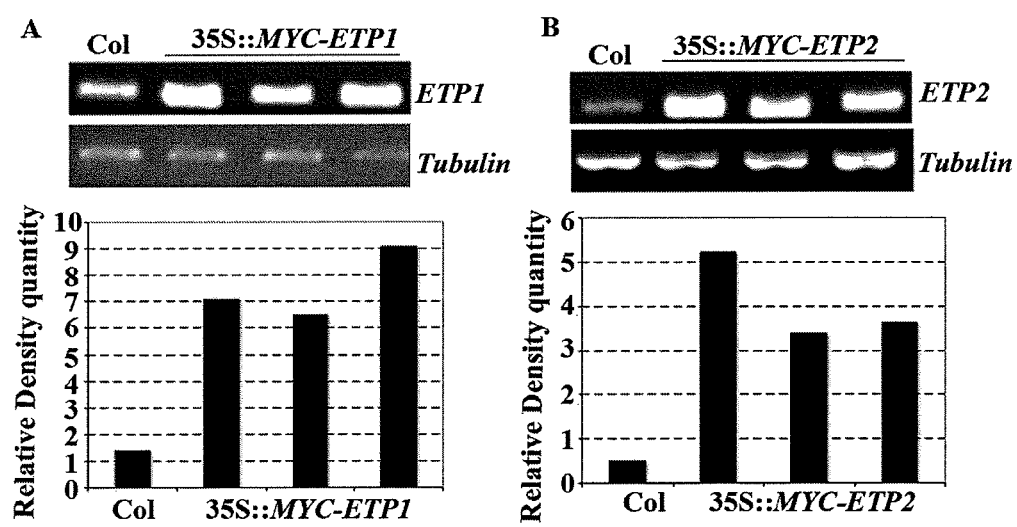
FIG. 13. The mRNA level of ETP1 and ETP2 were accumulated in 35S::MYC-ETP1/ETP2 transgenic plants. mRNA level of ETP1 (A) or ETP2 (B) were detected by RT-PCR using ETP1 or ETP2 specific primers (upper panel), and the relative density was quantified (lower panel). Total RNA was extracted from the leaves of 1-week-old dark-grown plants. The data were normalized to the corresponding tubulin (input) controls. The relative density quantification was done by software ImageGauge.

To test whether ETP1 and ETP2 are involved in the regulation of EIN2 protein turnover, we identified T-DNA insertion lines for mutants in both ETP1 and ETP2, etp1, etp2-1, etp2-2 (FIG. 10A) (Alonso, J. M. et al., Science, 301:653-657 (2003)). The response to ethylene of these mutant seedlings was tested. etp1 mutant seedlings manifested a slight ethylene hypersensitivity (FIG. 10D), while the ethylene response of etp2 mutant seedlings was similar to that of wild-type Col-0 (FIGS. 10B-C). Because of their sequence similarity, it is possible that ETP1 and ETP2 may function redundantly. To test this hypothesis, we utilized an amiRNA (Schwab, R. et al., Plant Cell, 18:1121-1133 (2006)) directed at knocking down the levels of both ETP1 and ETP2 mRNAs. A number of independent ETP1/ETP2 knock down (amiR-ETP1/ETP2) transgenic lines were isolated. As shown in FIG. 3A, the gene expression levels of ETP1 and ETP2 were significantly reduced in these knockdown lines to 15-30% of the level in wild-type Col-0 plants as measured by quantitative PCR (qPCR) analysis. Since we found that ETP1 and ETP2 were able to interact directly with EIN2, we investigated whether ETP1 and ETP2 might be involved in EIN2 regulation. To do this, we examined the level of EIN2 protein in amiR-ETP1/ETP2 plants. We found that EIN2 protein accumulation was greatly increased in amiR-ETP1/ETP2 plants compared to wild-type Col-0 plants (FIG. 3B and FIG. 11), suggesting that deficiency of ETP1 and ETP2 RNAs results in accumulation of EIN2 protein. To further illuminate the functions of ETP1 and ETP2 in the regulation EIN2 protein, we constructed transgenic plants containing either ETP1 or ETP2 under the control of the Cauliflower Mosaic Virus 35S promoter (35S), allowing constitutively high levels of expression for these two genes; the RNA levels of ETP1 and ETP2 were 5- to 10-fold increased in compare to wild type plants (FIG. 13). Compared to wild-type Col-0 plants, EIN2 protein levels were greatly reduced in plants over-expressing ETP1 or ETP2 (FIG. 3C). More interestingly, EIN2 accumulation was barely detectable in the ETP1 or ETP2 overexpressed seedlings even upon ACC treatment (FIG. 3D), suggesting that ethylene-dependent EIN2 accumulation is impaired by overexpression of ETP1 or ETP2. Taken together, these results demonstrate that ETP1 and ETP2 are negative regulators of EIN2 protein stability.

Knockdown of ETP1 and ETP2 Results in Constitutive Ethylene Response

Figure 4:
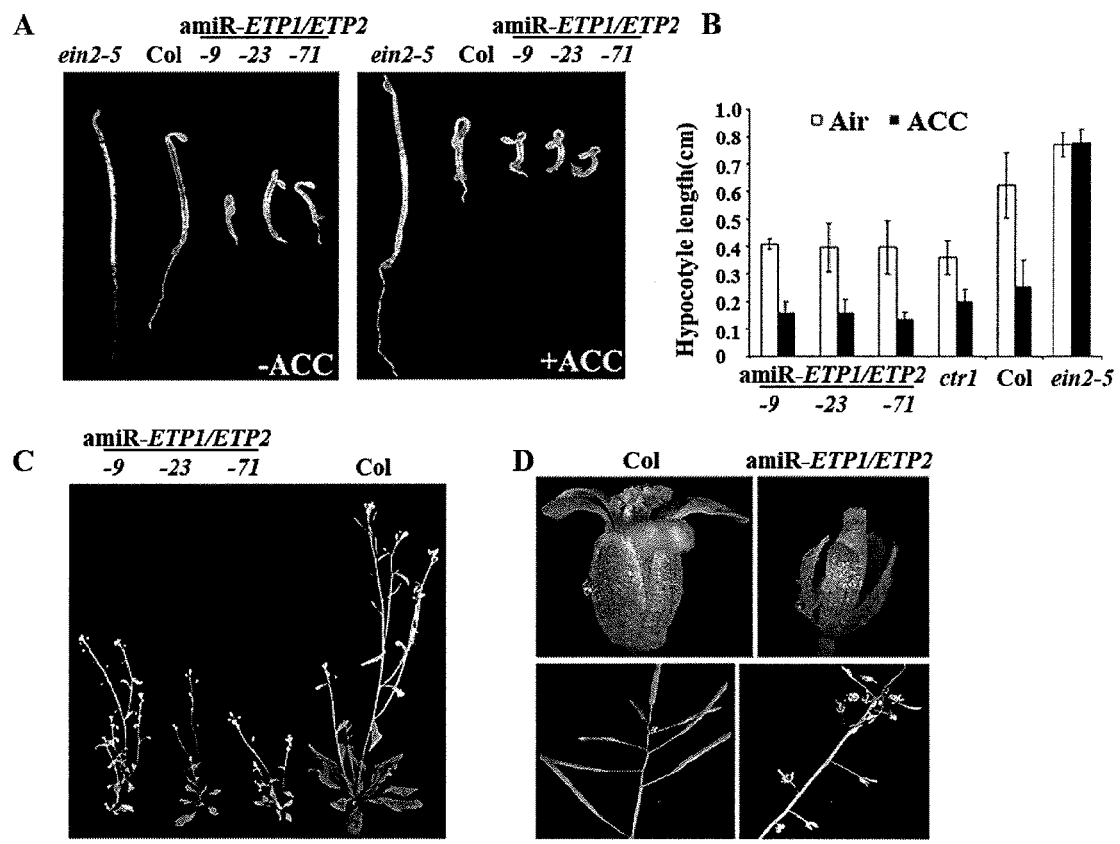
FIG. 4. Constitutive ethylene response phenotypes ETP1 or ETP2 knockdown plants support a function in ethylene signaling. (A) Ethylene response phenotype of 3-day-old etiolated seedlings of amiR-ETP1/ETP2 plants. The plants were grown on MS media supplied with (left panel) or without (right panel) 10 µM ACC in dark for 3 days. (B) Measurement of hypocotyl length of amiR-ETP1/ETP2 3-day-old etiolated seedlings. Each measurement is the average length (mean±standard error) of >10 hypocotyls. (C) Phenotype of five-week-old amiR-ETP1/ETP2 plants grown on soil. (D) amiR-ETP1/ETP2 mutant plants flower and silique morphology. The plants were grown on soil with 16 hours light and 8 hours dark, the flowers and siliques were photographed for 8-week-old plants or 10-week-old plants.
Figure 12:
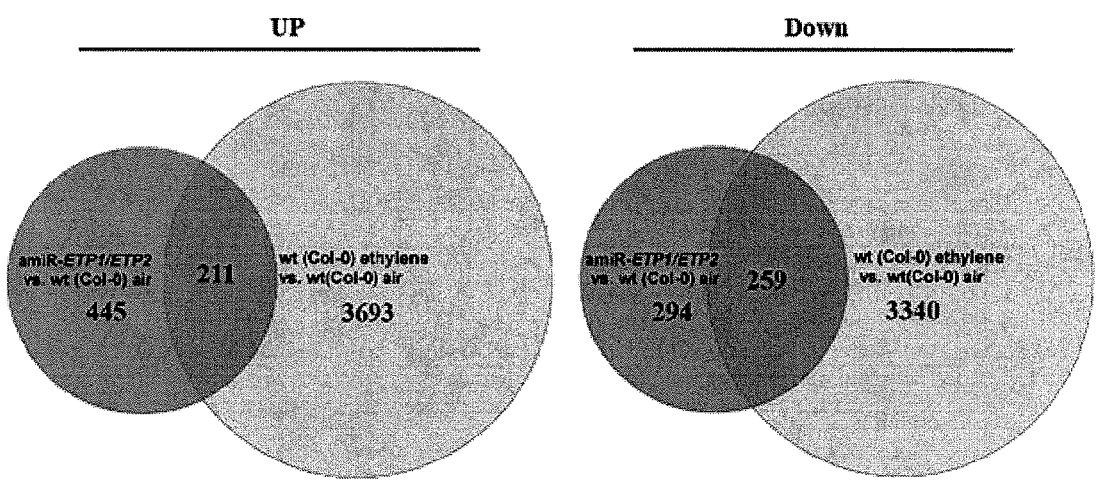
FIG. 12. Venn diagrams showing the overlap of genes up or down regulated in wild-type Col-0 plants treated with ethylene or amiR-ETP1/ETP2 plants. Both wild-type Col-0 ethylene treated and amiR-ETP1/ETP2 plants were first compared to an air treated control.

To better understand the molecular consequences of reduced ETP1/ETP2 RNA levels, we interrogated the transcriptome of wild-type Col-0 and amiR-ETP1/ETP2 plants before and after 4 hours of treatment with ethylene gas using Affymetrix ATH1 arrays. Total RNA was prepared from 3-week-old leaves of wild-type Col-0 and amiR-ETP1/ETP2 plants with or without 4 hours ethylene treatment. The microarray data revealed that about 40% of genes with significant changes in expression of amiR-ETP1/ETP2 knockdown lines compared to wild-type Col-0 plants overlapped with genes whose expression levels change in wild-type Col-0 plants upon ethylene treatment (FIG. 12), suggesting that ETP1 and ETP2 specifically affect numerous ethylene responsive genes. Therefore, we examined the ethylene response of amiR-ETP1/ETP2 three-day-old etiolated seedlings. When grown on MS medium, the amiR-ETP1/ETP2 seedlings manifested a typical constitutive ethylene response phenotype (FIGS. 4A-C). Interestingly, the amiR-ETP1/ETP2 seedlings still showed some response to exogenously added ethylene (FIG. 4B). This residual response may be a consequence of the remaining of ETP1 and ETP2 mRNA present in these knockdown lines or might also be due to redundancy of function for other members of this family of proteins.

As expected for plants that show a constitutive ethylene response phenotype, the adult amiR-ETP1/ETP2 plants had small rosettes and dwarfed growth habit, as well as displayed abnormal flowers whose gynoecium protrude from the unopened floral buds (FIG. 4C). The decreased level of ETP1 and ETP2 RNA in amiR-ETP1/ETP2 plants resulted in severe sterility, a phenotype that was also observed for plants that over-express EIN2-CEND (Alonso, J. M. et al., Science, 284: 2148-2152 (1999)). Under our experimental growth conditions, wild-type plants typically produce about 40 seeds per silique. However, in amiR-ETP1/ETP2 plants most siliques produce no seed although a few siliques do produce 2-3 seeds with an average 20 seeds per plant. Overall, these results demonstrated in the absence of ETP1 or ETP2, plants manifest a constitutive ethylene responsive phenotype, suggesting that that ETP1 and ETP2 negatively regulate ethylene response through the degradation of EIN2.

Overexpression of ETP1 or ETP2 Leads to a Reduction in Sensitivity to Ethylene

Figure 5:
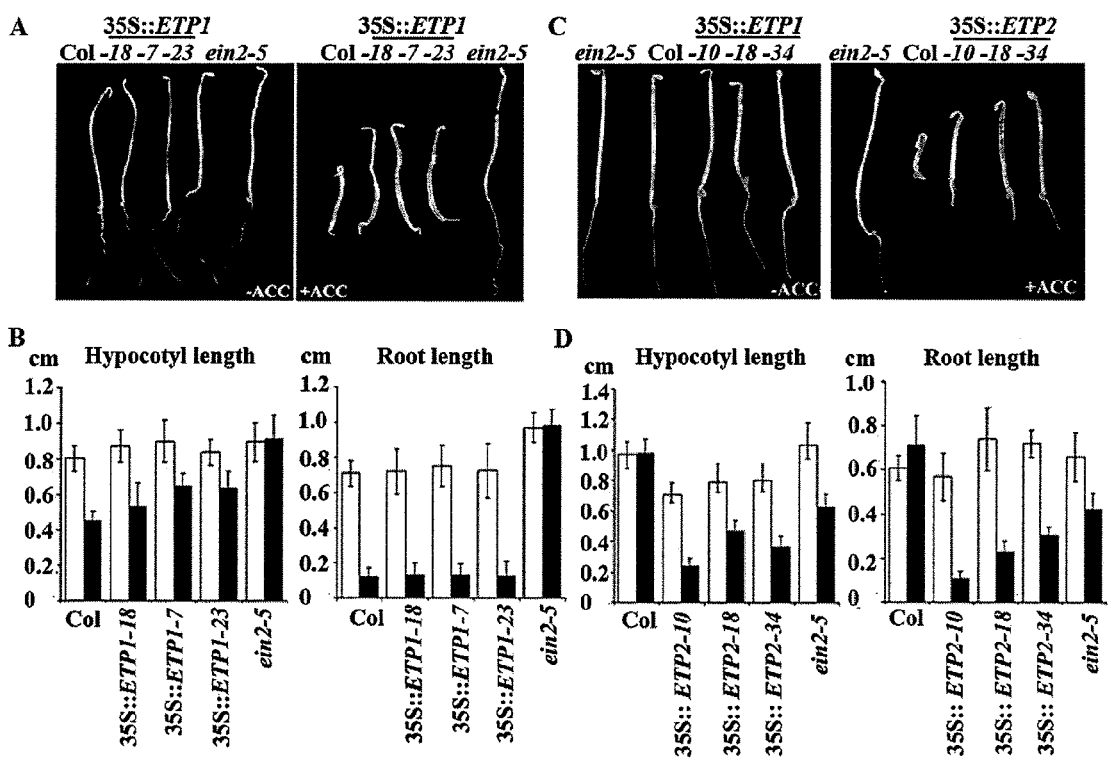
FIG. 5. Ethylene insensitive phenotypes ETP1 or ETP2 overexpression plants suggest a function in ethylene signaling. Phenotypes of 3-day-old etiolated seedlings over-expressing ETP1 (A) or ETP2 (C). Seedlings were grown on MS media supplemented without (upper panel) or with 10 µM ACC (lower panel) in dark for 3 days. Measurement of hypocotyl and root length for etiolated seedlings over-expressing ETP1 (B) or ETP2 (D). 3-day-old etiolated seedlings grown on the MS media supplemented with or without 10 µM ACC. Each measurement is the average length (mean±standard error) of >20 hypocotyls or roots.

To further confirm the function of ETP1 and ETP2 in the ethylene signaling pathway, we examined the ethylene response phenotype of 3-day-old etiolated seedlings over-expressing ETP1 or ETP2. As demonstrated in FIGS. 5A-B, overexpression of ETP1 resulted in a partial ethylene insensitive phenotype of the hypocotyl, while the roots of these plants did not show any difference in ethylene response compared to wild-type Col-0 seedlings. Interestingly, overexpression of ETP2 resulted in a strong ethylene insensitive phenotype both in roots and hypocotyls (FIGS. 5C, E). The ethylene insensitive phenotype displayed by plants over-expressing ETP2 is consistent with a greater reduction in EIN2 protein levels (FIG. 3D). These results demonstrate that over-expressing ETP1 or ETP2 results in significant ethylene insensitive phenotypes, which further suggests that ETP1 and ETP2 negatively regulate ethylene response through their regulation of EIN2 levels.

Ethylene Negatively Regulates ETP1 and ETP2 Protein Levels

Figure 6:
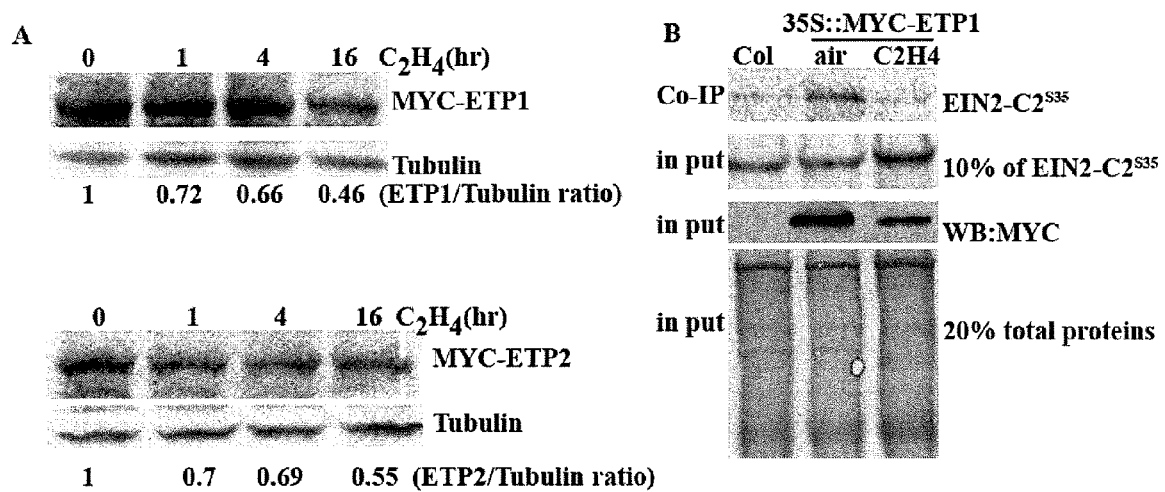
FIG. 6. Ethylene plays a negative role in ETP1 and ETP2 protein expression. (A) Protein levels of MYC-ETP1 (upper panel) and MYC-ETP2 (lower panel) after various times of ethylene treatment. The total protein extracts were subjected to immunoblotting with anti-MYC antibody. The same membranes were stripped and re-probed with an anti-tubulin antibody. (B) The interaction of ETP1 and EIN2 is affected by ethylene. Total protein extracts from 35S::MYC-ETP1 transgenic plants with or without ethylene treatment were incubated with equal excessive amounts of $^{35}$S-methionine labeled EIN2-C2 protein from in vitro transcriptional/translational system, and subsequently immunoprecipitated with an anti-MYC antibody. The EIN2-C2$^{35S}$ was detected by autoradiography. WB: western blot.
Figure 14:
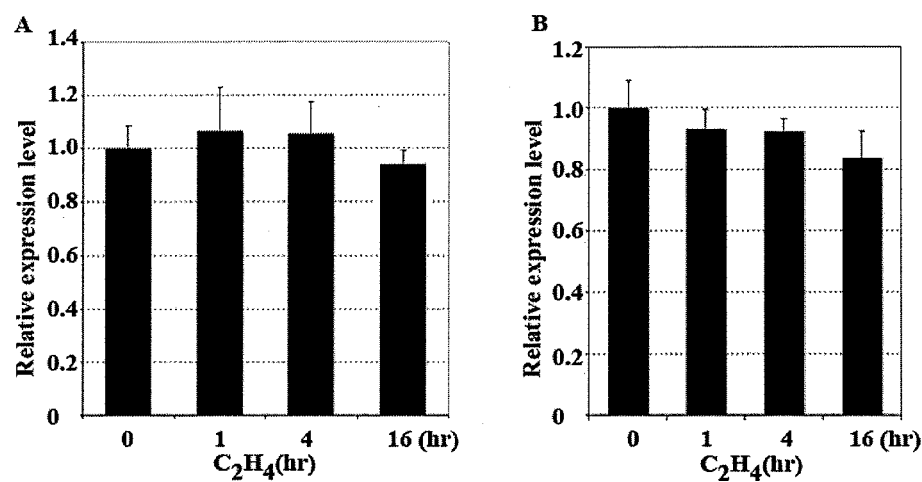
FIG. 14. The level of ETP1 and ETP2 mRNA is not regulated by ethylene. qPCR analysis of ETP1 (A) and ETP2 (B) transcript levels in wild type plants treated with ethylene for different time periods. Total RNA was extracted from the leaves of 1-week-old dark-grown plants. The data were normalized to the corresponding actin (input) controls. The data shown are the mean±SD of three independent experiments.

To better understand how ethylene gas regulates ETP1 and ETP2, the RNA expression of ETP1 and ETP2 was examined after different times of ethylene treatment. We found that the expression of ETP1 and ETP2 RNA was unaffected even with prolonged ethylene treatment (FIG. 14). Therefore, we further examined ETP1 and ETP2 protein levels upon different times of ethylene treatment. As shown in FIG. 6A, the protein levels of both ETP1 and ETP2 were down-regulated upon treatment with exogenous ethylene. In addition, a co-immunoprecipitation assay was used to examine the stability of the interaction between EIN2 and ETP1 upon ethylene treatment. An equivalent amount of $S^{35}$-labeled EIN2-C2 from in vitro transcriptional/translational system was co-immunoprecipitated with anti-MYC antibody in the presence of total protein prepared from 35S::MYC-ETP1 transgenic plants treated with or without ethylene. As shown in FIG. 6B, the level of ETP1 protein was decreased by added ethylene, resulting in less EIN2 co-immunoprecipitating with ETP1. These findings suggest that ethylene may perturb the interaction between EIN2 and ETP1 through down-regulation of ETP1 protein levels, providing an additional layer of complexity of EIN2 regulation.

Discussion

EIN2 Protein Level Plays a Key Role in Ethylene Signaling

Our biochemical and genetic studies described here demonstrate ethylene responses in plants are facilitated by control of EIN2 protein turnover through the 26S proteasome pathway. Notably, the stability of EIN2 protein is decreased drastically in 30 minutes with CHX treatment. In contrast, EIN2 is stabilized and accumulates in the presence of specific proteasome inhibitors MG132 or MG115. The ubiquitin pathway has been shown to be important for degrading membrane proteins but in many cases, the proteasome is not involved. Instead the proteins are shuttled to the lysosome. However, this latter pathway is insensitive to MG132, indicating that EIN2 is a short half-life protein and the protein is subjected to proteasome-mediated protein degradation. In support of these findings, a recent study found that the EIN2 C-terminus was capable of interacting with the COP1/signalsome (Christians, M. J. et al., Plant J., 55(3):467-477 (2008)), however, the biochemical consequence of this interaction was not reported.

The ein2 null mutant completely loses ethylene response (Alonso, J. M. et al., Science, 284:2148-2152 (1999)). In contrast, over expression of EIN2-CEND causes many ethylene responsive phenotypes in adult plants (Alonso, J. M. et al., Science, 284:2148-2152 (1999)). Furthermore, the accumulation of EIN3 protein is completely blocked in the ein2 mutant (Guo, H. and Ecker, J. R., Cell, 115:667-677 (2003)). All of these studies have demonstrated that the EIN2 plays an irreplaceable function in the ethylene response pathway.

Since EIN2 mRNA levels are unaffected by treatment with exogenous ethylene (Alonso, J. M. et al., Science, 284:2148-2152 (1999)), we examined EIN2 protein levels in plants treated with ethylene and in various ethylene response mutants. We found that the constitutive ethylene responsive mutant ctr1 significantly over-accumulated EIN2 protein relative to wild type at all time points tested, while there was no detectable accumulation of EIN2 in the ethylene insensitive mutants etr1. Moreover, protein accumulation of EIN2 in ein3eil1 plants was much reduced compared to wild type plants upon the ethylene treatment. Additionally, we found that the level of EIN2 protein positively correlates with the ethylene response phenotypes, suggesting that plants respond rapidly to exogenous ethylene by adjusting the level of EIN2 protein through its turnover. According to the current model, when plants are grown in air (absence of ethylene), the negative regulator CTR1 actively represses ethylene responses. Genetics evidence demonstrated that EIN2 is the first positive regulatory factor downstream of CTR1 (Ecker, J. R., Science, 268:667-675 (1995); Guo, H. and Ecker, J. R., *Curr. Opin. Plant. Biol.*, 7:40-49 (2004)), and our findings now demonstrate that EIN2 protein dramatically accumulates in the constitutive ethylene response mutant, ctr1, suggesting that of the accumulation of EIN2 results in the constitutive ethylene response phenotype of these plants. However, the connection between CTR1 and EIN2 is unknown. One possibility is that in the absence of ethylene, CTR1 may function in concert with other, yet-to-be identified protein(s) to prevent EIN2 from accumulating. Previous studies have shown that accumulation of EIN3 protein fully depends on the presence of EIN2 protein (Guo, H. and Ecker, J. R., *Cell*, 115:667-677 (2003)). We have found that EIN3 protein also accumulates in the amiR-ETP1/ETP2 knockdown plants where EIN2 accumulates (unpublished data), which offers additional evidence that the protein level of EIN2 is crucial for EIN3 stability and ethylene signaling. Interestingly, we found the protein level of EIN2 does not become saturated until after 4 hours of ethylene treatment, while EIN3 protein level is saturated after 1 hour of ethylene treatment (Guo, H. and Ecker, J. R., *Cell*, 115:667-677 (2003)). The molecular mechanism behind these differences is unclear. However, a question of major biological interest is to uncover the link between EIN2 and EIN3 in the ethylene signaling pathway, which may shed light on the differences in timing for accumulation of protein levels.

EIN2 C-Terminal End is of Crucial Importance to Ethylene Response

EIN2 is a ubiquitous protein and exists in all the plant species examined. Interestingly, an EIN2 homolog is even present in the algae, *Chlamydomonas reinhardtii* (Qiao and Ecker unpublished data). Through most of the plant species, EIN2-CEND is the most highly conserved domain (FIG. 9), suggesting this domain may be of high importance for ethylene signal transduction. Interestingly, one of the ein2 mutant alleles previously isolated carries a single substitution (A to C at 3943) mutation in the CEND of EIN2 still manifests a strong ethylene insensitive phenotype (Alonso, J. M. et al., *Science*, 284:2148-2152 (1999)). This mutant allele of EIN2 suggests that an intact EIN2-CEND is essential for maintaining normal EIN2 function in ethylene signaling.

To identify EIN2 interacting proteins and potentially fill in gaps within the ethylene signaling pathway, we used EIN2-CEND to perform a yeast two-hybrid screen. Among the potential interactors, an F-box protein, ETP1, was identified. Furthermore, both directed yeast two-hybrid and pull down experiments demonstrated that EIN2-CEND interacts with ETP1 and its *Arabidopsis* homolog ETP2. In addition, we demonstrated that the most highly conserved domain of the EIN2-CEND is necessary and sufficient for the interaction of EIN2 with ETP1 and ETP2, and this <250 amino acids of EIN2 may be essential for regulation of the ethylene response. Overall, these results suggest that the interaction between EIN2-CEND and ETP1 and ETP2 is crucial to a proper ethylene response in *Arabidopsis*, and this regulation through C-terminal interaction with F-box proteins mediating protein turnover is important for ethylene response in most if not all plant species.

The Regulation of EIN2 by ETP1 and ETP2 is Integral to Ethylene Signaling

In plants, there are about 700 F-box proteins (Gagne, J. M. et al., *Proc. Natl. Acad. Sci. U.S.A.*, 99:11519-11524 (2002)), and they are involved in a plethora of biological processes, including plant hormone responses (Gray, W. M. et al., *Nature*, 414:271-276 (2001); Dharmasiri, N. et al., *Nature*, 435:441-445 (2005); Kepinski, S, and Leyser, O., *Nature*, 435:446-451 (2005); Xie, D. X. et al., *Science*, 280:1091-1094 (1998); Guo, H. and Ecker, J. R., *Cell*, 115:667-677 (2003); Potuschak, T. et al., *Cell*, 115:679-689 (2003); Fu, X. et al., *Plant Cell*, 16:1406-1418 (2004)), lateral root formation (Coates, J. C. et al., *Proc. Natl. Acad. Sci. U.S.A.*, 103: 1621-1626 (2006)), light signaling and clock control (Mas, P. et al., *Nature*, 426:567-570 (2003); Imaizumi, T. et al., *Nature*, 426:302-306 (2003); Imaizumi, T. et al., *Science*, 309:293-297 (2005)), pollen recognition and rejection (Sijacic, P. et al., *Nature*, 429:302-305 (2004); Qiao, H. et al., *Plant Cell*, 16:2307-2322 (2004); Qiao, H. et al., *Plant Cell*, 16:582-595 (2004)), and plant-pathogen interactions (Kim, H. S. and Delaney, T. P., *Plant Cell*, 14:1469-1482 (2002); Duyvesteijn, R. G. et al., *Mol. Microbiol.*, 57:1051-1063 (2005); Van den Burg, H. A. et al., *Plant Cell*, 20:697-719 (2008)). Based on phylogenetic analysis, the super family of F-box proteins are divided into 20 groups (Gagne, J. M. et al., *Proc. Natl. Acad. Sci. U.S.A.*, 99:11519-11524 (2002)). ETP1 and ETP2 belong to a novel subfamily of F-box protein of which little is known (Gagne, J. M. et al., *Proc. Natl. Acad. Sci. U.S.A.*, 99:11519-11524 (2002)). Specifically, both ETP1 and ETP2 carry the F-box protein associated (FBA_1) motif, which is different from typical protein interaction domains carried by most well known F-box proteins (Lechner, E. et al., *Curr. Opin. Plant. Biol.*, 9:631-638 (2006)). We have found that the non-typical FBA_1 domain interacts directly with EIN2, indicating that this region may play a role in recognition of its substrates, which in our case is EIN2 (data not shown). However, at this point we can not be certain that EIN2 is the only target of ETP1 or ETP2, and if other substrates might be recognized by different portions of the ETP proteins.

Our study provides compelling evidence that ETP1 and ETP2 are negative regulators of EIN2 protein levels, and the EIN2-ETP1/ETP2 interaction is central in controlling ethylene responses. First, ETP1 and ETP2 interact with EIN2 physically. Second, our genetic experiments of knocking-down gene expression of ETP1 and ETP2 simultaneously (amiR-ETP1/ETP2) demonstrates that plants lacking these two proteins manifest constitutive ethylene response phenotypes both in etiolated seedlings and adult plants. This phenotype is extremely strong although the amiR-ETP1/ETP2 plants are slightly larger than their ctr1 counterpart (data not shown). Strikingly, knocking down ETP1 and ETP2 expression also stunted growth and renders the plants partially sterile, which is similar to the phenotypes observed in the etr1/etr2/ein4/ers2 quadruple mutant (Hua, J. et al., *Plant Cell*, 10:1321-1332 (1998)) and the ebf1 ebf2 double mutant (Guo, H. and Ecker, J. R., *Cell*, 115:667-677 (2003); Potuschak, T. et al., *Cell*, 115:679-689 (2003)). In contrast, overexpression of ETP1 and ETP2 results in plants manifesting an ethylene insensitive phenotype. Third, our biochemical data demonstrates that the level of EIN2 is greatly increased in the ETP1/ETP2 knock-down (amiR-ETP1/ETP2) plants, but in ETP1 or ETP2 overexpression plants EIN2 does not accumulate upon treatment with ACC, suggesting that ETP1 and ETP2 suppress EIN2 protein accumulation. Fourth, genome-wide microarray analysis demonstrated that ethylene-inducible genes are significantly induced in amiR-ETP1/ETP2 plants compared to wild-type Col-0 plants. Finally, our study demonstrated that ethylene negatively regulates ETP1 protein level and this impairs the interaction between EIN2 and ETP1, which likely results in accumulation of EIN2 protein. Further biochemical studies of this highly conserved and essential integral membrane protein will be critical to uncover the mechanistic details governing its hormone signaling properties.

Experimental Procedures
Plant Growth Condition, Ethylene and Drug Treatment

The Columbia ecotype (Col-0) was the parent strain for all mutant and transgenic lines used in this study. *Arabidopsis* seeds were surface-sterilized and plate on the MS medium (4.3 g MS salt, 10 g sucrose pH 5.7, 8 g bactoagar per liter). After 3-4 days cold (4° C.) treatment, the plates were wrapped in foil and kept in a 24° C. incubator before the phenotypes of seedlings were analyzed. For propagation, seedlings were transferred from plates to soil (Pro-mix-HP) and grown to maturity at 22° C. under a 16 hr light/8 hr dark cycles. Ethylene treatment of *Arabidopsis* seedlings grown on plates was performed in air-tight containers (AirGas) by flowing hydrocarbon-free air supplied with 10 parts per million (ppm) ethylene or treated with hydrocarbon-free air alone (Kieber, J. J. et al., *Cell*, 72:427-441 (1993)). For drug treatment, *Arabidopsis* etiolated seedlings were incubate with liquid MS medium for 3 hrs in dark in room temperature. Afterward, the seedlings were treated with MG132 (100 µm), MG115 (100 µm) or DMSO (0.1%) for various times prior to harvesting the tissue.

Antibody Preparation and Immunoblot Assays and Pull Down

The coding region corresponding to residues 808 amino acid to 1294 amino acid of EIN2 protein was PCR amplified, purified from *E. coli* and used to raise polyclonal antibodies in rabbits. Immunoblot assays were performed as described (Guo, H. and Ecker, J. R., *Cell*, 115:667-677 (2003)) with minor modifications. Membrane proteins were extracted according to (Chen, Y. F. et al., *J. Biol. Chem.*, 277:19861-19866 (2002)), protein samples were mixed with 2×SDS-PAGE sample buffer, heated at 90° C. for 3 min, cooled on ice for 2 min. The proteins were fractionated by 4-12% gradient Bis-Tris Novex precast gels (Invitrogen), transferred on to nitrocellulose filter and the blot was probed with anti-EIN2 or anti-H$^+$-ATPase antibody (kindly provided by Dr. M. J. Chrispeels).

In vitro transcribed and translated S$^{35}$ labeled EIN2-C2 proteins were generated according to the protocol of TNT Coupled Wheat Germ Extract Systems (Promega). Total protein extracts were prepared from MYC-ETP1 plants treated with or without ethylene. The same amount of S$^{35}$ labeled EIN2-C2 was incubated with total protein extract from MYC-ETP1 plants treated with or without ethylene, anti-MYC antibody and IgG agarose at 4° C. overnight. The IgG agarose beads were washed by PBST for 6 times, and the proteins were eluted by 2×SDS-PAGE sample buffer, heated at 90° C. for 3 min, cooled on ice for 2 min. The proteins were fractionated by 4-12% gradient Bis-Tris Novex precast gels (Invitrogen). The presence of EIN2-C2$^{S35}$ was detected by autoradiography.

Yeast Two-Hybrid Interaction Assay

The cDNA sequences of the EIN2, ETP1 and ETP2 (Yamada, K. et al., *Science*, 302:842-846 (2003)) and their derivatives were cloned into pAS2 LOXP or pACT2 LOXP vector (Clontech; H. Li and J. R. E., unpublished data and http://signal.salk.edu/pHOST.html). Yeast transformation, growth conditions, and interaction assays were performed according to the manufacturer's instructions (Clontech).

Construction of Transgenic *Arabidopsis* Plants

Knockdown of ETP1 and ETP2 using an amiRNA was carried out as described (Schwab, R. et al., *Plant Cell*, 18:1121-1133 (2006)) and (http://wmd.weigelworld.org/cgi-bin/mirnatools.pl). The oligonucleotides used for amiRNA construction are "TCTTTGAATAAACGGTCCCAT" (SEQ ID NO: 16)
and

"TCTTTGAATAAACGGTGCCAT". (SEQ ID NO: 17)

The binary vector used was pCHF3, and contained the artificial microRNA backbone miR 319. The binary vector pKYLX7 was modified by inserting a loxP site and MYC tag in the MCS region (H. Li and J. R. E., unpublished data and http://signal.salk.edu/pHOST.html). The full length ORFs of ETP1 and ETP2 were cloned into pUNI15 vector at the NcoI/SaiI site (a gift from Dr. Stephen Elledge). An in vitro plasmid recombination reaction, catalyzed by Cre recombinase, was carried out between pUNI15 (containing F box cDNA sequence) and the modified pKYLX7 with Myc tag. The resulting plasmids that harbor ETP1 and ETP2 coding regions driven by CaMV 35S promoter were introduced into *Agrobacterium* strain GV3101 and subsequently transformed into *Arabidopsis* plants. Transgenic T1 plants were identified by selection for kanamycin resistance. The triple response phenotype was scored in T2 seedlings originated from individual transgenic T1 plants. Homozygous T3 seedlings were used for phenotype analysis and immunoblotting studies.

Microarray Experiments and Analysis

All RNA extractions were performed using the RNeasy Kit (Qiagen) per manufacturers instructions. cRNA synthesis, labeling, and hybridization to *Arabidopsis* ATH1 gene expression arrays (Affymetrix Inc) were performed according to manufacturer's recommendations except that the labeling reactions were scaled down by 50%. After hybridization, the arrays were scanned and the CEL files were used for further analysis. All normalization and quality controls were performed using the packages from the remote analysis computation for gene expression data (RACE, http://race.unil.ch) (Psarros, M. et al., *Nucleic Acids Res*, 33 (Web Server issue): W638 (2005)). After normalization, present, marginal, and absent flags, together with the intensity values converted from logarithmic to linear scales, were exported to GeneSpring GX (Agilent). Ethylene-regulated genes were selected using a linear model approach (Smyth, G. K., *Stat Appl Genet Mol Biol*, 3:3 (2004)) implemented in the limma package from BioConductor (Smyth, G. K., *Stat Appl Genet Mol Biol*, 3:3 (2004)). This analysis was done using the Remote Analysis Computation for Gene Expression (Psarros, M. et al., *Nucleic Acids Res*, 33 (Web Server issue):W638 (2005)). Genes that had a P value of <0.05 and a fold change between control and treatment or control and mutants experiments greater than 1.5 were selected. Finally, only genes that were present or marginal in both replicates in the treated (when selecting upregulated genes) or in the untreated (when selecting for down regulated genes) samples were further considered.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A plant comprising a heterologous recombinant expression cassette, wherein the plant has altered sensitivity to ethylene compared to a control plant lacking the expression cassette, the expression cassette comprising a promoter operably linked to a polynucleotide, which polynucleotide, when expressed, increases expression of an ETP1 or ETP2 polypeptide compared to a control plant lacking the expression cassette, wherein increased expression of the ETP1 or ETP2 polypeptide results in reduced ethylene sensitivity compared to the control plant, and wherein said polynucleotide encodes a polypeptide, which polypeptide
   is an F-box protein; and
   binds to EIN2.

2. The plant of claim 1, wherein the polynucleotide encodes a polypeptide comprising an amino acid sequence at least 25% identical to any of SEQ ID NOS:1-8 or 18-22.

3. A method of making a plant of claim 1, the method comprising
   introducing the expression cassette into a plurality of plants; and
   selecting a plant that expresses the polynucleotide from the plurality of plants.

4. The method of claim 3, wherein the selecting step comprises selecting a plant that has reduced ethylene sensitivity.

5. The plant of claim 1, wherein said polypeptide is at least 25% identical to SEQ ID NO:1 or at least 25% identical to SEQ ID NO:2.

6. The plant of claim 1, wherein said F-box protein comprises an FBA-1 motif.

7. A plant comprising a heterologous recombinant expression cassette, wherein the plant has altered sensitivity to ethylene compared to a control plant lacking the expression cassette, the expression cassette comprising a promoter operably linked to a polynucleotide, which polynucleotide, when expressed, decreases expression of an ETP1 or ETP2 polypeptide compared to a control plant lacking the expression cassette, wherein decreased expression of the ETP1 or ETP2 polypeptide results in increased ethylene sensitivity compared to the control plant, and wherein said ETP1 or ETP2 polypeptide is an F-box protein and binds to EIN2.

8. The plant of claim 7, wherein the polynucleotide comprises at least 20 contiguous nucleotides, or the complement thereof, of a nucleic acid encoding any of SEQ ID NOS:1-8 or 18-22, such that expression of the polynucleotide inhibits expression of an endogenous ETP1 or ETP2 gene.

9. A method of making a plant of claim 7, the method comprising introducing the expression cassette into a plurality of plants; and selecting a plant that expresses the polynucleotide from the plurality of plants.

10. The method of claim 9, wherein the selecting step comprises selecting a plant that has increased ethylene sensitivity.

* * * * *